United States Patent [19]

Lee et al.

[11] Patent Number: 5,260,262
[45] Date of Patent: Nov. 9, 1993

[54] SUBSTITUTED PYRIDINE COMPOUNDS HAVING HERBICIDAL ACTIVITY

[75] Inventors: Len F. Lee, St. Charles; Yuen-Lung L. Sing, St. Louis; Sai C. Wong, Chesterfield, all of Mo.

[73] Assignee: Monsanto Company, St. Louis, Mo.

[21] Appl. No.: 802,924

[22] Filed: Dec. 6, 1991

[51] Int. Cl.⁵ .................. A01N 43/40; C07D 413/06; C07D 417/06
[52] U.S. Cl. ............................ 504/252; 546/280; 546/275; 546/276; 546/277; 546/278
[58] Field of Search ............. 546/280; 71/94; 504/252

[56] References Cited

U.S. PATENT DOCUMENTS

| | | | |
|---|---|---|---|
| 5,100,461 | 3/1992 | Sing et al. | 546/280 X |
| 5,125,961 | 6/1992 | Avinbauh et al. | 504/252 |
| 5,129,943 | 7/1992 | Hegde et al. | 504/252 X |

*Primary Examiner*—Alan L. Rotman
*Attorney, Agent, or Firm*—Grace L. Bonner; Stanley M. Tarter; Richard H. Shear

[57] ABSTRACT

The present invention provides novel herbicidal pyridines characterized by having in the 3- or 5-position an aliphatic or aromatic 1-ketone.

15 Claims, No Drawings

SUBSTITUTED PYRIDINE COMPOUNDS HAVING HERBICIDAL ACTIVITY

This invention relates to a new class of substituted pyridinecarboxylic acid derivatives having a wide range of activity as herbicides.

Pyridine derivatives have, for many years, been investigated for use in biological sciences. For example, 2,6-bis(trifluoromethyl)-4-pyridinols have been found useful as herbicides and fungicides as disclosed in U.S. Pat. No. 3,748,334. Such compounds are characterized by substitution in the 4-position by a hydroxy radical. In addition to the hydroxy radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

In EPO Patent 44,262 there are disclosed 2,6-dialkyl-3-phenylcarbamyl-5-pyridinecarboxylates and 5-cyano-compounds useful as herbicides. There is no disclosure of the 2-haloalkyl radicals or any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3-and 5-positions while the 2- and 6-positions are occupied by carboxylate groups. The 4-position is open to substitution by a wide range of materials including halogens, hydroxy radicals, alkoxy, and carboxyl groups. Such compounds have found utilization as herbicides, bactericides, and fungicides. When the 4-position is occupied by a silver salt, U.S. Pat. No. 1,944,412 discloses that such compounds have been utilized in the production of X-ray pictures with intravenous injection of such compounds.

Pyridinedicarboxylate compounds useful as herbicides are described in U.S. Pat. No. 4,692,184. These compounds have fluorinated methyl groups at the 2- and 6-positions and carboxylic acid derivative at the 3- and 5-positions.

Other pyridinedicarboxylate compounds including pyrazole amides are disclosed in U.S. Pat. No. 4,698,093. U.S. Pat. Nos. 4,066,438 and 4,180,395 disclose various herbicidal polyhalo substituted pyridyloxy compounds.

Other herbicidal pyridine compounds substituted at the 3- and/or 5-position with a carboxylic acid-derived heterocyclic moiety, as well as herbicidal compositions and use of these compounds are disclosed in U.S. Pat. No. 4,988,384.

BRIEF DESCRIPTION OF THE INVENTION

It is an object of this invention to provide herbicidal methods and compositions utilizing the novel pyridines of this invention.

The novel compounds of this invention are useful as herbicides or intermediates which can be converted to herbicides and ar represented by the generic formula

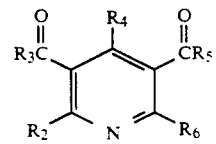

wherein:

$R_2$ and $R_6$ are independently lower alkyl, fluorinated methyl, chlorofluorinated methyl, or chlorinated methyl, provided that one of $R_2$ and $R_6$ is fluorinated methyl or chlorofluorinated methyl;

$R_3$ is alkoxy or alkylthio;

$R_4$ is hydrogen, alkyl, cycloalkyl, or cycloalkylalkyl; and $R_5$ is selected from alkyl, alkenyl, alkynyl, haloalkyl, cycloalkyl, cycloalkenyl, cyanoalkyl, hydroxyalkyl, hydroxyalkenyl, hydroxyiminoalkyl, aminocarbonyl, alkylaminocarbonyl, haloalkylcarbonyl, dialkoxyalkylaminocarbonyl, alkoxycarbonylalkyl, alkylthioalkyl, hydroxycarbonyl, dioxolanylalkyl, and phenyl, optionally substituted with one or more halogens;

or $R_5$ is a heterocyclic radical selected from furanyl, imidazolyl, isoxazolyl, isothiazolyl, 1,3,4-oxadiazolyl, oxazolyl, 4,5-(dihydro)oxazolyl, pyrazinyl, pyrazolyl, pyridazinyl, pyridinyl, pyridinyl N-oxide, pyrimidinyl, pyrrolyl, tetrazolyl, thiazolyl, 4,5-(dihydro)thiazolyl, thienyl, and triazolyl, or is such a heterocyclic radical substituted with one or more radicals selected from halo, amino, aminocarbonyl, cyano, alkoxy, alkyl, alkoxyalkyl, alkoxycarbonyl, alkylamino, and dialkylamino.

Preferably, $R_5$ is 2-thiazolyl or 4-pyrimidinyl, $R_4$ is 2-methylpropyl, and $R_2$ and $R_6$ are independently trifluoromethyl and difluoromethyl.

As used herein throughout the specification and claims, the following terms have the following meanings unless otherwise specifically indicated:

The terms "alkyl" and "lower alkyl" are used interchangeably in this document and mean herein both straight and branched chain saturated hydrocarbon radicals having 1 to 7 carbon atoms, unless a different carbon number range is expressly stated. Examples of such radicals include, but are not limited to, ethyl, methyl, n-propyl, 1-ethylpropyl, 1-methylpropyl, n-butyl, 1,1-dimethylethyl, 2,2-dimethylpropyl, pentyl, and the like.

The term "cycloalkyl" means saturated cyclic radicals having 3 to 7 carbon atoms, such as cyclopropyl, cyclobutyl, cyclopentyl, cyclohexyl, and cycloheptyl.

The terms "alkenyl" and "alkynyl" herein mean alkenyl and alkynyl groups having 2 to 7 carbon atoms. Examples of such alkenyl groups include ethenyl, 1-propenyl, 2-propenyl, 1-butenyl, 2-butenyl, 3-butenyl, 2-methyl, i-propenyl, 2-methyl-2-propenyl, and the like. Examples of such alkynyl groups include ethynyl, 1-propynyl, 2-propynyl, and so forth.

The term "cycloalkylalkyl" is intended to mean alkyl radicals having 1 to 3 carbon atoms which is substituted with a cycloalkyl group having 3 to 7 carbon atoms.

The term "haloalkyl" is intended to mean an alkyl radical (as defined above) substituted with one or more halogen atoms selected from F, Cl, Br, and I. "Haloalkenyl" and "haloalkynyl" refer to alkenyl and alkynyl radicals substituted with one or more halogens.

The term "fluorinated methyl" means herein methyl radicals having one or more fluorine atoms attached thereto, and includes radicals wherein all hydrogen atoms are replaced by fluorine. The term "chlorofluorinated methyl" means herein a methyl radical having at least one hydrogen replaced by fluorine and at least one other hydrogen replaced by chlorine. The term "chlorinated methyl" means herein methyl radicals having one or more chlorine atoms attached thereto, and includes radicals wherein all hydrogen atoms are replaced by chlorine.

DETAILED DESCRIPTION OF THE INVENTION

The novel herbicidal derivative and their compounds of this invention are readily prepared by reaction as illustrated in the following working examples. The present invention is merely illustrated by the following working examples but obviously is not limited thereto. All percentages are given on a weight/weight basis unless otherwise indicated.

The starting materials for preparing the compounds of the present invention are substituted pyridines having at the 3 or 5-position a formyl or chlorocarbonyl radical and having the desired substituents at the other positions. 3- or 5-formylpyridines and 3- or 5-chlorocarbonylpyridines were prepared as disclosed in U.S. Pat. No. 4,692,184 (Lee, Sep. 8, 1987), which is herein incorporated by reference. The 3- or 5-alkylketones of the present invention are also useful as intermediates for further reactions to produce other compounds of the present invention.

As used throughout the specification, including the Examples and claims, the following abbreviations have the following meanings:

| | |
|---|---|
| THF | tetrahydrofuran |
| DMF | N,N-dimethylformamide |
| n-BuLi | n-butyllithium |
| h | hour(s) |
| conc. | concentrated |
| RT | room temperature |

EXAMPLE A

This example illustrates the preparation of Compound 1, an example of the reaction of a pyridine acid chloride and an organometallic reagent. To a flame dried 3-neck flask (with septum, mechanical stirrer, and nitrogen inlet) was added methyl 5-(chlorocarbonyl)-6-(difluoromethyl)-4-(2-methylpropyl)-2-(trifluoromethyl)-3-pyridinecarboxylate (5 g, 0.013 mol) and then anhydrous THF (30 mL). The mixture was cooled in an ice bath and methylmagnesium bromide (12.5 mL, 0.04 mol, 3.2M in ether) was added dropwise. The light red-brown solution was stirred in the ice bath for 10 min and then poured into ice water, acidified with conc. HCl, and extracted with ether. The ether extract was washed with water, dried (MgSO$_4$), and concentrated to yield 4.45 g of a light brown oil, which was Kugelrohr distilled to afford the desired compound as a light yellow solid, an 81% yield. m.p. 46°–48° C.

EXAMPLE B

This example illustrates the preparation of Compound 14, an example of the condensation of a pyridine aldehyde and an organometallic reagent, followed by oxidation of the secondary alcohol. A solution of 2M isopropylmagnesium chloride in ether (40 mL) (Aldrich) was added in a slow stream to a solution of methyl 2-(difluoromethyl)-5-formyl-4-(2-methylpropyl)-6-(trifluoromethyl)-3-pyridinecarboxylate (7 g, 20 mmol) in anhydrous ether (30 mL) at −30° to −20° C. After the mixture was stirred for 3 h at <10° C., it was poured into iced water, acidified with conc. HCl, and extracted with methylene chloride. The organic extract was washed with brine, dried (MgSO$_4$), and conc. to give 3 g of methyl 2-(difluoromethyl)-5-(1-hydroxy-2-methylpropyl)-4-(2-methylpropyl)-6-(trifluoromethyl)-3-pyridinecarboxylate. A solution of this alcohol (3 g) in 20 mL of acetone was cooled to <10° C., and 8N Jones' reagent (4 mL) was added dropwise. The mixture was stirred at RT for 24 h. Ether and water were added and the aqueous layer separated and extracted with ether. The combined ether layers were washed with water and brine, dried (MgSO$_4$), and conc. in vacuo. The residue was purified by flash chromatography on silica gel with 8% ethyl acetate/cyclohexane to give 1.6 g of the desired compound as a light yellow solid, a yield of 21.1%. m.p. 45°–47° C.

EXAMPLE C

This example illustrates the preparation of Compound Numbers 23 and 24, an example of the acylation of a pyridine methyl ketone, followed by further derivation to compounds of the present invention. To methyl 5-acetyl-2-(difluoromethyl)-4-(2-methylpropyl)-6-(trifluoromethyl)-3-pyridinecarboxylate (Compound No. 4, prepared as in Example A) (10.8 g, 30 mmol) in anhydrous ether (100 mL) were added methyl formate (3 g) and 25% sodium methoxide in methanol (10 g) (Aldrich), and the resulting mixture was stirred overnight. It was then poured into iced water, acidified with conc. HCl, and extracted with methylene chloride. The organic extract was washed with water and brine, dried (MgSO$_4$), and conc. in vacuo. The residue was purified by flash chromatography with 20% ethyl acetate/cyclohexane to yield 6 g methyl (Z)-2-(difluoromethyl)-5-(3-hydroxy-1-oxo-2-propenyl)-4-(2-methylpropyl)-6-(trifluoromethyl)-3-pyridinecarboxylate (Compound No. 23) as a viscous red oil, a yield of 52.6%. $n_D^{25}$ 1.4857.

A mixture of this compound (5.1 g), hydroxylamine hydrochloride (1.1 g), and triethylamine (2.4 mL) in dioxane (20 mL) was heated at reflux for 3 h and cooled to RT. The precipitate was filtered off, and water and methylene chloride were added to the filtrate. The organic layer was separated, washed with brine, dried (MgSO$_4$), and conc. The residue was purified by flash chromatography with 10% and then 15% ethyl acetate/cyclohexane to yield 3.7 g of methyl 2-(difluoromethyl)-5-[3-(hydroxyimino)-1-oxopropyl]-4-(2-methylpropyl)-6-(trifluoromethyl)-3-pyridinecarboxylate (Compound No. 24) as a solid.

EXAMPLE D

This example illustrates the preparation of Compound Number 12, an example of the halogenation of a pyridine methyl ketone. A mixture of Compound Number 1, prepared as in Example A (35.5 g, 0.10 mol) and pyrrolidinone hydrotribromide (74.8 g, 0.151 mol) in carbon tetrachloride (400 mL) was refluxed under nitrogen for 7 h and then stirred at RT overnight. Water (200 mL) and 10% NaOH (40 mL) were added, and the layers were separated. The aqueous layer was washed with methylene chloride and the organic layers were combined, dried (MgSO$_4$), and conc. Separation by chromatography, followed by recrystallization from hexanes yielded the desired compound as white crystals, a 79% yield. m.p. 56°–57.5° C.

EXAMPLE E

This example illustrates the preparation of Compound Number 42, an example of the oxidation of a pyridine methyl ketone, followed by further derivatization of the resulting acid. A mixture of Compound Number 4 (70 g), celite (20 g), and selenium dioxide (26 g) in pyridine (160 mL) was heated at 80°–100° C. to 3 h, cooled to RT and filtered through celite. The filtrate was conc. in vacuo to give the α-keto acid. A solution of this acid, potassium carbonate (57 g), and methyl iodide (50 mL) in DMF (200 mL) was stirred at room temperature for 18 h. Water and methylene chloride were added and the layers separated. The organic layer was washed with water and brine, dried (MgSO$_4$), and conc. to yield 60 g of crude pyridine methyl α-keto ester. A solution of this ester (10 g) and NaOH (1 g) in methanol (100 mL) was stirred at room temperature for 2 h. Methanol was removed in vacuo, and the residue partitioned between water and ether. The aqueous layer was acidified with conc. HCl and extracted with methylene chloride. The organic extract was washed with brine, dried (MgSO$_4$), and conc. to yield 7.5 g of the desired compound as a solid, m.p. 114°–121° C.

EXAMPLE F

This example illustrates the preparation of Compound Number 46, an example of the conversion of an ester of pyridinecarboxylic acid to the free acid, from which other compounds of the present invention, for example, other alkyl esters or alkylthioesters, may be readily prepared. A mixture of Compound Number 8, prepared as in Example A, (78.55 g, 0.214 mol), sodium hydroxide (20 g, 0.5 mol) in water (180 mL), and THF (250 mL) was stirred at room temperature overnight. The mixture was then acidified with conc. HCl, diluted with water, and extracted with ether. Evaporation of the ether in vacuo, followed by recrystallization from ether/hexanes gave 30 g of the desired compound as an off-white powder, a 40% yield. m.p. 109°–111° C.

EXAMPLE G

This example illustrates the preparation of Compound Number 53. To a suspension of magnesium (1.4 g, 58 mmol) in anhydrous ether (40 mL) containing several iodine crystals was added dropwise a solution of 2-bromothiophne (10 g, 62 mmol) in anhydrous ether (20 mL). The reaction was exothermic; the mixture was stirred at ambient temperature for 1.5 h. The resulting Grignard reagent was cooled to 0°–5° C. and a solution of methyl 2-(difluoromethyl)-5-formyl-4-(2-methylpropyl)-6-(trifluoromethyl)-3-pyridinecarboxylate (6.8 g, 20 mmol) in anhydrous ether (20 mL) was added. The mixture was stirred for 2 h, poured into iced water, and acidified with conc. HCl. The organic layer was separated, washed with water and brine, dried (MgSO$_4$), and conc. The residue was eluted on a silica gel column with 15% ethyl acetate/cyclohexane to yield 6.6 g of methyl 2-(difluoromethyl)-5-(hydroxy-2-thienylmethyl)-4-(2-methylpropyl)-6-(trifluoromethyl)-3-pyridinecarboxylate, a 77.6% yield. m.p. 78°–88° C.

To a solution of this alcohol (5.8 g, 14 mmol) in acetone (20 mL), cooled in an ice-water bath, was added dropwise 8N Jones reagent (5 mL). The mixture was stirred for 2 h, then poured into iced water and extracted with methylene chloride. The extract was washed with water and brine, dried (MgSO$_4$), and conc. The residue was purified by chromatography with 10% ethyl acetate/cyclohexane to afford 4.4 g of the desired compound, a 75% yield. m.p. 82°–86° C.

EXAMPLE H

This example illustrates the preparation of Compound Number 54, an example of the addition of a heterocycle to a pyridine aldehyde by lithiation of the heterocycle, condensation with the aldehyde, and oxidation of the resulting alcohol to the compound of the present invention.

To 2.5N n-BuLi in hexane (30 mL) cooled to 0° C was added in a slow stream furan (7 g, 0.1 mol) in anhydrous ether (60 mL). The mixture was heated at reflux for 3 h under a nitrogen atmosphere and then cooled to −6° C. A solution of methyl 2-(difluoromethyl)-5-formyl-4-(2-methylpropyl)-6-(trifluoromethyl)-3-pyridinecarboxylate (6 g, 17.6 mmol) in anhydrous ether (20 mL) was added dropwise and stirring was continued for 2 h. The mixture was then poured into iced water, acidified with conc. HCl and extracted with methylene chloride. The extract was washed with water and brine, dried (MgSO$_4$), and conc. The oily residue was purified by chromatography with 10% ethyl acetate/cyclohexane to yield 4.4 g of methyl 2-(difluoromethyl)-5-(2-furanylhydroxymethyl)-4-(2-methylpropyl)-6-(trifluoromethyl)-3-pyridinecarboxylate as an orange oil, a 61% yield. $n_D^{25}$ 1.4863.

This alcohol was oxidized with 8N Jones reagent as described above to yield the desired compound. m.p. 90°–93° C.

EXAMPLE I

This example illustrates the preparation of Compound Number 61, an example of the addition of a heterocycle to a pyridine aldehyde by halogen-metal exchange of the haloheterocycle, condensation of the resulting organometallic reagent with the aldehyde, and oxidation of the resulting alcohol to the compound of the present invention.

To a solution of 3-bromothiophene (4 g 24.5 mmol) in dry THF (80 mL) cooled to −70° C. was added dropwise 2.5M n-BuLi in hexane (11 mL, 27.5 mmol). The mixture was stirred for one-half h. A solution of methyl 2-(difluoromethyl)-5-formyl-4-(2-methylpropyl)-6-(trifluoromethyl)-3-pyridinecarboxylate (6.6 g, 19.5 mmol) in anhydrous THF (20 mL) was added dropwise and stirring was continued for 1 h while the temperature was maintained at −70° C. The mixture was allowed to warm to RT and then poured into iced water, acidified with conc. HCl and extracted with methylene chloride. The extract was washed with water and brine, dried (MgSO$_4$), and conc. The residue was purified by chromatography with 10% ethyl acetate/cyclohexane to yield 5.6 g of methyl 2-(difluoromethyl)-5-(hydroxy-3-thienylmethyl)-4-(2-methylpropyl)-6-(trifluoromethyl)-3-pyridinecarboxylate, a 68.9% yield.

This alcohol (2.2 g, 5.2 mmol) was oxidized with 8N Jones reagent (2.6 mL) as described above to yield 0.8 g of the desired compound as a white solid, a yield of 36 4%. m.p. 97°–100° C.

EXAMPLE J

This example illustrates the preparation of Compound Number 75, an example of the cleavage by acid hydrolysis of a labile group on a heterocyclic pyridine derivative of the present invention.

Compound Number 74, prepared as in Example H (2.4 g, 5.3 mmol) was suspended in 10% HCl (40 mL), heated at reflux for 2.5 h, cooled to RT, and extracted with methylene chloride. The extract was washed with saturated aqueous potassium carbonate solution and brine, dried (MgSO$_4$), and conc. Purification by chromatography with 30% ethyl acetate/cyclohexane afforded 1.4 g of the desired compound as a white solid, a 64.5% yield. m.p. 137°–140° C.

EXAMPLE K

This example illustrates the preparation of Compound Number 55. To a solution of 1-methylimidazole (0.9 g, 11 mmol) in acetonitrile (20 mL), cooled in an ice water bath, were added methyl 5-(chlorocarbonyl)-2-difluoromethyl)-4-(2-methylpropyl)-6-(trifluoromethyl)-3-pyridinecarboxylate (3.8 g, 10 mmol) and a solution of triethylamine (3 mL) in acetonitrile (7 mL). The mixture was stirred at room temperature for 18 h and conc. The residue was partitioned between water and methylene chloride. The organic layer was separated, washed with brine, dried (MgSO$_4$), and conc. The residue was purified by chromatography with 50% ethyl acetate-cyclohexane to yield 2.1 g of the desired compound as a yellow solid, a 50% yield. m.p. 127°–130° C.

EXAMPLE L

This example illustrates the preparation of Compound Number 63, an example of the preparation of compounds of the present invention by cyclization. A mixture of methyl 2-(difluoromethyl)-5-[(2-hydroxyethylamino)oxoacetyl]-4-(2-methylpropyl)-6-(trifluoromethyl)-3-pyridinecarboxylate prepared like Compound 33 as in Example E, (2.2 g, 5.2 mmol), phosphorous pentasulfide (1.5 g), and 1 g of celite in xylene (16 mL) was heated at reflux for 1 h, cooled, and filtered through celite. The celite was thoroughly washed with ether. The combined filtrate was dissolved in methylene chloride, washed with saturated aqueous sodium bicarbonate solution, dried (MgSO$_4$), and conc. The residue was purified by chromatography with 10% and then 20% ethyl acetate/cyclohexane to yield 0.8 g of the desired compound as a brown solid, a 36.4% yield. m.p. 49°–57° C.

EXAMPLE M

This example illustrates the preparation of Compound Number 110, an example of the preparation of compounds of the present invention by chlorine-fluorine exchange. A mixture of Compound Number 105, prepared as in Example H (1 g), potassium fluoride (3 g), and 18-crown-6-ether (0.1 g) was refluxed for 72 h. The solvent was removed in vacuo and the residue dissolved in methylene chloride and water. The aqueous layer was extracted with methylene chloride and the combined organic layers were washed with water and brine, dried (MgSO$_4$), and conc. Purification by chromatography with 20% ethyl acetate/hexanes afforded 0.4 g of the desired compound as an orange oil.

EXAMPLE N

This example illustrates the preparation Compound 28. A solution of Compound 25 (2 g, 4.9 mmol), methyl methanethiolsulfonate (0.8 g, 6.3 mmol), and sodium methoxide (1 g, 18.5 mmol) in 20 mL methanol was refluxed for 5 h, cooled and concentrated in vacuo. The residue was partitioned between 3 N HCl and methylene chloride. The organic layer was separated, washed with brine, dried over MgSO$_4$ and concentrated under reduced pressure. The liquid residue was refluxed in 6N HCl for 18 h, cooled and extracted with methylene chloride. The organic layer was washed with water, brine, dried over MgSO$_4$, and concentrated in vacuo. Flash chromatography of the residue on silica gel first with 3% and then 5% ethyl acetate/cyclohexane as eluent gave 0.9 g (46.4%) of the desired product as a white solid. m.p. 58°–62° C.

EXAMPLE O

This example illustrates the preparation of Compound 30. To a solution of Compound 28 (2.8 g, 7.1 mmol) in 40 mL methylene chloride was added 80% m-chloroperbenzoic acid (1.7 g, 7.9 mmol) in portions at 0°–5° C. and stirring was continued at RT for 18 h. The organic layer was filtered, washed with saturated sodium bicarbonate solution, water, brine, dried over MgSO$_4$, and concentrated in vacuo. Flash chromatography of the residue on silica gel first with 15%, 50% and then 80% ethyl acetate-cyclohexane gave 2 g (67.8%) of 3-pyridinecarboxylic acid, 2-(difluoromethyl)-4-(2-methylpropyl)-5-(methylsulfinyl)acetyl)-6-(trifluoromethyl)-, methyl ester, as yellow oil. $n_D^{25}$1.4903.

A mixture of this compound (1.4 g, 3.4 mmol) and iodine (0.7 g) in 20 mL methanol was refluxed for 3 h and cooled. The excess iodine was destroyed with saturated aqueous sodium bisulfite solution. Methanol was removed in vacuo. Water and methylene chloride were added and the two layers were separated. The organic layer was washed with brine, dried over MgSO$_4$, and concentrated in vacuo. Flash chromatography of the residue on silica gel with 6% ethyl acetate-cyclohexane gave 0.6 g (40%) of the product as pale yellow solid. m.p. 60°–66° C.

EXAMPLE P

This example illustrates the preparation of Compounds 62, 106, 107, and 109, an example of reduction of a α-hydroxyhaloheterocyclomethyl derivative to the α-hydroxyheterocyclomethyl derivative, and oxidation of this derivative to compounds of the present invention. A mixture of methyl 5-[(2-chloro-5-thiazolyl)-hydroxymethyl)-2-(difluoromethyl)-4-(2-methylpropyl)-6-(trifluoromethyl)-3-pyridinecarboxylate (7.2 g, 16 mmol), 6 mL triethylamine, and 5% of palladium on activated carbon catalyst (5 g) in 80 mL methanol was placed in a Parr hydrogenation apparatus at 50 psi and RT for 18 h. The reaction mixture was filtered through celite. The celite was thoroughly washed with methanol. The combined filtrates was concentrated in vacuo. The residual solid was purified by flash chromatography on silica gel with 30% ethyl acetate-cyclohexane to afford 3-pyridinecarboxylic acid, 2-(difluoromethyl)-5-(hydroxy-5-thiazolylmethyl)-4-(2-methylpropyl)-6-(trifluoromethyl)-, methyl ester (5 g, 73.5%) as A light yellow solid. m.p. 140°-150° C.

This alcohol (3.2 g, 7.5 mmol) was treated with Jones reagent (4 mL) to afford the desired compound (2 g, 62.5%) as a white solid. m.p. 87°-90° C.

EXAMPLE Q

This example illustrates the preparation of Compound 101, an example of the formation of the heterocycle by cycloaddition reaction. Sodium (7.87 g, 0.35 mol) was cautiously added in portions to 250 mL methanol under nitrogen. Methyl 5-acetyl-2-(difluoromethyl)-4-(2-methylpropyl)-6-(trifluoromethyl)-3-pyridinecarboxylate (20 g, 0.057 mol) was added at 25° C., followed by dropwise addition of isoamyl nitrite (33.15 g, 0.283 mol). The mixture was stirred overnight at 25° C., then quenched with ice/concentrated HCl slush, and extracted with ether. The combined ether layers were washed with saturated sodium bicarbonate and dried (MgSO$_4$). The solvent was evaporated in vacuo and the residue purified by HPLC with 10% ethyl acetate-hexane to give 22 g (99%) of 3-pyridinecarboxylic acid, 2-(difluoromethyl)-5-((hydroxyimino)acetyl)-4-(2-methylpropyl)-6-(trifluoromethyl)-, methyl ester, as a yellow solid. m.p. 84°-86° C.

A mixture of this compound (4.83 g, 12.63 mmol), and N-chlorosuccinimide (2.03 g, 15.16 mmol) in 30 mL anhydrous DMF was stirred at 25° C. for 1 h, then quenched with water and extracted with ether. The ether portion was washed three times with water and dried (MgSO$_4$). Removal of solvent under reduced pressure gave 5.63 g of crude chlorooxime which was used immediately for further synthesis. To the crude chloro-oxime in 50 mL of anhydrous THF was added ethylvinyl ether (109 g, 15.16 mmol), followed by triethylamine (154 g, 15.16 mmol). After stirring at 25° C. for 1 h, the reaction mixture was quenched with brine and extracted with ether. The ether was dried (MgSO$_4$) and concentrated in vacuo to give 5.1 g of crude ethoxyisoxazoline.

A solution of the crude isoxazoline and p-toluenesulfonic acid (2 g) was refluxed for 36 h. After that the solvent was removed in vacuo and the residue was chromatographed to give 2.86 g of crude isoxazole. Recrystallization of the solid from ether-hexane gave 1.1 g of white powder. m.p. 72°-72.5° C.

EXAMPLE R

This example illustrates the preparation of Compound 92, an example of the preparation of a compound of this invention by conversion of a difluoromethyl group to a dichloromethyl group. To aluminum chloride (5 g) in 30 mL methylene chloride was added 3 g of Compound 56, and the resulting mixture was stirred at RT for 2 h. The content was poured cautiously into ice-water-concentrated HCl and extracted with methylene chloride. The organic solution was washed with water, brine, dried over MgSO$_4$ and concentrated in vacuo. Flash chromatography of the residue on a silica gel column with 7% ethyl acetate/cyclohexane as eluent gave 2.2 g of the desired compound as a white solid. m.p. 114°-118° C.

EXAMPLE S

This example illustrates the preparation of Compound 93, an example of preparation of compound of this invention by chlorination of a dichloromethyl group to a trichloromethyl group. To a solution of Compound 92 (1.4 g) and hexachloroethane (1.1 g) in 10 mL THF at −30° C. was added dropwise 4 mL 1M lithium bis(trimethylsilyl)amide in THF. The resulting solution was stirred at −30° C. for 20 minutes, warmed to RT and poured into ice-3N HCl, and extracted with methylene chloride. The organic layer was washed with water, brine, dried over MgSO$_4$ and concentrated in vacuo. Flash chromatography of the residue on a silica gel column (5% ethyl acetate/cyclohexane) gave 0.4 g of the desired compound as a white solid. m.p. 111°-114° C.

The following is a listing by number and nomenclature of compounds herein. Unless otherwise indicated the physical property is the melting point in °C.

| Comp. No. | Name | Phys. Prop. |
|---|---|---|
| 1 | 3-Pyridinecarboxylic acid, 5-acetyl-6-(difluoromethyl)-4-(2-methylpropyl)-2-(trifluoromethyl)-, methyl ester | 46-48 |
| 2 | 3-Pyridinecarboxylic acid, 6-(difluoromethyl)-4-(2-methylpropyl)-5-(1-oxopropyl)-2-(trifluoromethyl)-, methyl ester | yellow oil |
| 3 | 3-Pyridinecarboxylic acid, 5-acetyl-6-(difluoromethyl)-2-(trifluoromethyl)-, ethyl ester | 1.4825 $n_D^{21}$ |
| 4 | 3-Pyridinecarboxylic acid, 5-acetyl-2-(difluoromethyl)-4-(2-methylpropyl)-6-(trifluoromethyl)-, methyl ester | 65-67 |
| 5 | 3-Pyridinecarboxylic acid, 5-benzoyl-6-(difluoromethyl)-4-(2-methylpropyl)-2-(trifluoromethyl)-, methyl ester | 74-76 |
| 6 | 3-Pyridinecarboxylic acid, 5-benzoyl-6-(difluoromethyl)-2-(trifluoromethyl)-, ethyl ester | 1.5113 $n_D^{25}$ |
| 7 | 3-Pyridinecarboxylic acid, 6-(difluoromethyl)-4-(2-methylpropyl)-5-(1-oxopentyl)-2-(trifluoromethyl)-, methyl ester | 59-60 |
| 8 | 3-Pyridinecarboxylic acid, 2-(difluoromethyl)-4-(2-methylpropyl)-5-(1-oxopropyl)-6-(trifluoromethyl)-, methyl ester | 47-50 |
| 9 | 3-Pyridinecarboxylic acid, 5-acetyl-6-(difluoromethyl)-4-methyl-2-(trifluoromethyl)-, methyl ester | 69-72 |
| 10 | 3-Pyridinecarboxylic acid, 6-(difluoromethyl)-4-(2-methylpropyl)-5-(1-oxobutyl)-2-(trifluoromethyl)-, methyl ester | b.p. 100 °C. @ 0.25 torr |
| 11 | 3-Pyridinecarboxylic acid, 6-(difluoromethyl)-5-(3-methyl-1-oxobutyl)-4-(2-methylpropyl)-2-(trifluoromethyl)-, methyl ester | 72-74 |
| 12 | 3-pyridinecarboxylic acid, 5-(bromoacetyl)-6-(difluoromethyl)-4-(2-methylpropyl)-2-(trifluoromethyl)-, methyl ester | 56-57.5 |
| 13 | 3-Pyridinecarboxylic acid, 2-(difluoromethyl)-4-(2-methylpropyl)-5-(1-oxobutyl)-6-(trifluoromethyl)-, methyl ester | 45-50 |
| 14 | 3-Pyridinecarboxylic acid, 2-(difluoromethyl)-5-(2-methyl-1-oxopropyl)-4-(2-methylpropyl)-6-(trifluoromethyl)-, methyl ester | 45-47 |
| 15 | 3-Pyridinecarboxylic acid, 2-(difluoromethyl)-4-(2-methylpropyl)-5-(1-oxopentyl)-6-(trifluoromethyl)-, methyl ester | 49-51 |
| 16 | 3-Pyridinecarboxylic acid, 6-(difluoromethyl)-5-[3-(1,3-dioxolan-2-yl)-1-oxopropyl]-4-(2-methylpropyl)-2-(trifluoromethyl)-, methyl ester | 1.4595 $n_D^{25}$ |
| 17 | 3-Pyridinecarboxylic acid, 5-(cyclopropylcarbonyl)-2-(difluoromethyl)-4-(2-methylpropyl)-6-(trifluoromethyl)-, methyl ester | 44-48 |

| Comp. No. | Name | Phys. Prop. |
|---|---|---|
| 18 | 3-Pyridinecarboxylic acid, 5-(bromoacetyl)-2-(difluoromethyl)-4-(2-methylpropyl)-6-(trifluoromethyl)-, methyl ester | 59-63 |
| 19 | 3-Pyridinecarboxylic acid, 5-(dibromoacetyl)-2-(difluoromethyl)-4-(2-methylpropyl)-6-(trifluoromethyl)-, methyl ester | 1.4958 $n_D^{25}$ |
| 20 | 3-Pyridinecarboxylic acid, 2-(difluoromethyl)-4-(2-methylpropyl)-5-(1-oxo-2-butenyl)-6-(trifluoromethyl)-, methyl ester | 55-59 |
| 21 | 3-Pyridinecarboxylic acid, 5-(dichloroacetyl)-2-(difluoromethyl)-4-(2-methylpropyl)-6-(trifluoromethyl)-, methyl ester | 52-56 |
| 22 | 3-Pyridinecarboxylic acid, 5-(cyanoacetyl)-2-(difluoromethyl)-4-(2-methylpropyl)-6-(trifluoromethyl)-, methyl ester | 90-93 |
| 23 | 3-Pyridinecarboxylic acid, 2-(difluoromethyl)-5-(3-hydroxy-1-oxo-2-propenyl)-4-(2-methylpropyl)-6-(trifluoromethyl)-, methyl ester (Z)- | 1.4857 $n_D^{25}$ |
| 24 | 3-Pyridinecarboxylic acid, 2-(difluoromethyl)-5-[3-(hydroxyimino)-1-oxopropyl]-4-(2-methylpropyl)-6-(trifluoromethyl)-, methyl ester | 115-119 |
| 25 | 3-Pyridinepropanoic acid, 6-(difluoromethyl)-5-(ethoxycarbonyl)-4-(2-methylpropyl)-beta-oxo-2-(trifluoromethyl)-, methyl ester | 1.4705 $n_D^{25}$ |
| 26 | 3-Pyridinecarboxylic acid, 2-(difluoromethyl)-5-(2,2-dimethyl-1-oxopropyl)-4-(2-methylpropyl)-6-(trifluoromethyl)-, methyl ester | 78-82 |
| 27 | 3-Pyridinecarboxylic acid, 5-(cyclopentylcarbonyl)-2-(difluoromethyl)-4-(2-methylpropyl)-6-(trifluoromethyl)-, methyl ester | 72-75 |
| 28 | 3-Pyridinecarboxylic acid, 2-(difluoromethyl)-4-(2-methylpropyl)-5-[(methylthio)acetyl]-6-(trifluoromethyl)-, methyl ester | 58-62 |
| 29 | 3-Pyridinecarboxylic acid, 2-(difluoromethyl)-5-(1,3-dioxolan-2-ylacetyl)-4-(2-methylpropyl)-6-(trifluoromethyl)-, methyl ester | 68-69 |
| 30 | 3-Pyridinecarboxylic acid, 2-(difluoromethyl)-5-[methoxy(methylthio)acetyl]-4-(2-methylpropyl)-6-(trifluoromethyl)-, methyl ester | 60-66 |
| 31 | 3-Pyridinecarboxylic acid, 2-(difluoromethyl)-4-(2-methylpropyl)-5-(1-oxo-2-propynyl)-6-(trifluoromethyl)-, methyl ester | 1.4660 $n_D^{25}$ |
| 32 | 3-Pyridinecarboxylic acid, 2-(difluoromethyl)-5-(3-methyl-1-oxobutyl)-4-(2-methylpropyl)-6-(trifluoromethyl)-, methyl ester | 75-78 |
| 33 | 3-Pyridinecarboxylic acid, 5-[[(2-chloroethyl)amino]oxoacetyl]-2-(difluoromethyl)-4-(2-methylpropyl)-6-(trifluoromethyl)-, methyl ester | 82-86 |
| 34 | 3-Pyridinecarboxylic acid, 2-(difluoromethyl)-5-[[(2,2-dimethoxyethyl)amino]oxoacetyl]-4-(2-methylpropyl)-6-(trifluoromethyl)-, methyl ester | 123-126 |
| 35 | 3-Pyridinecarboxylic acid, 5-(aminooxoacetyl)-2-(difluoromethyl)-4-(2-methylpropyl)-6-(trifluoromethyl)-, methyl ester | 126-129 |
| 36 | 3-Pyridinecarboxylic acid, 2-(difluoromethyl)-5-[(methylamino)oxoacetyl]-4-(2-methylpropyl)-6-(trifluoromethyl)-, methyl ester | 60-65 |
| 37 | 3-Pyridinecarboxylic acid, 2-(difluoromethyl)-5-(4-fluorobenzoyl)-4-(2-methylpropyl)-6-(trifluoromethyl)-, methyl ester | 133-135 |
| 38 | 3-Pyridinecarboxylic acid, 5-(4-chlorobenzoyl)-2-(difluoromethyl)-4-(2-methylpropyl)-6-(trifluoromethyl)-, methyl ester | 126-128 |
| 39 | 3-Pyridinecarboxylic acid, 5-(2-chlorobenzoyl)-2-(difluoromethyl)-4-(2-methylpropyl)-6-(trifluoromethyl)-, methyl ester | 1.5160 $n_D^{25}$ |
| 40 | 3-Pyridinecarboxylic acid, 5-(3-chlorobenzoyl)-2-(difluoromethyl)-4-(2-methylpropyl)-6-(trifluoromethyl)-, methyl ester | 62-67 |
| 41 | 3-Pyridinecarboxylic acid, 2-(difluoromethyl)-5-(2-fluorobenzoyl)-4-(2-methylpropyl)-6-(trifluoromethyl)-, methyl ester | 1.5232 $n_D^{25}$ |
| 42 | 3-Pyridineacetic acid, 6-(difluoromethyl)-4-(2-methylpropyl)-5-(methoxycarbonyl)-alpha-oxo-2-(trifluoromethyl)- | 114-121 |
| 43 | 3-Pyridinecarboxylic acid, 5-(1-cyclopenten-1-ylcarbonyl)-2-(difluoromethyl)-4-(2-methylpropyl)-6-(trifluoromethyl)-, methyl ester | 83-86 |
| 44 | 3-Pyridinecarboxylic acid, 2-(difluoromethyl)-5-(3-fluorobenzoyl)-4-(2-methylpropyl)-6-(trifluoromethyl)-, methyl ester | 1.4989 $n_D^{25}$ |
| 45 | 3-Pyridinecarboxylic acid, 5-(2,4-difluorobenzoyl)-2-(difluoromethyl)-4-(2-methylpropyl)-6-(trifluoromethyl)-, methyl ester | 1.5125 $n_D^{25}$ |
| 46 | 3-Pyridinecarboxylic acid, 2-(difluoromethyl)-4-(2-methylpropyl)-5-(1-oxopropyl)-6-(trifluoromethyl)-, methyl ester | 109-111 |
| 47 | 3-Pyridinecarbothioic acid, 2-(difluoromethyl)-4-(2-methylpropyl)-5-(1-oxopropyl)-6-(trifluoromethyl)-, S-methyl ester | 63-65 |
| 49 | 3-pyriinecarboxylic acid, 4-(cyclopropylmethyl)-2-(difluoromethyl)-5-(1-oxopropyl)-6-(trifluoromethyl)-, methyl ester | 56-58 |
| 50 | 3-Pyridinecarboxylic acid, 2-(difluoromethyl)-4-(2-methylpropyl)-5-(1-oxopropyl)-6-(trifluoromethyl)-, ethyl ester | 1.4545 $n_D^{25}$ |
| 51 | 3-Pyridinecarbothioic acid, 2-(difluoromethyl)-4-(2-methylpropyl)-5-(1-oxopropyl)-6-(trifluoromethyl)-, S-ethyl ester | 44-46 |
| 52 | 3-Pyridinecarboxylic acid, 4-cyclobutyl-2-(difluoromethyl)-5-(1-oxopropyl)-6-(trifluoromethyl)-, methyl ester | 77-79 |
| 53 | 3-Pyridinecarboxylic acid, 2-(difluoromethyl)-4-(2-methylpropyl)-5-(2-thienylcarbonyl)-6-(trifluoromethyl)-, methyl ester | 82-86 |
| 54 | 3-Pyridinecarboxylic acid, 2-(difluoromethyl)-5-(2-furanylcarbonyl)-4-(2-methylpropyl)-6-(trifluoromethyl)-, methyl ester | 90-93 |
| 55 | 3-Pyridinecarboxylic acid, 2-(difluoromethyl)-5-[(1-methyl-1H-imidazol-2-yl)carbonyl]-4-(2-methylpropyl)-6-(trifluoromethyl)-, methyl ester | 127-130 |
| 56 | 3-Pyridinecarboxylic acid, 2-(difluoromethyl)-4-(2-methylpropyl)-5-(2-thiazolylcarbonyl)-6-(trifluoromethyl)-, methyl ester | 1.5081 $n_D^{25}$ |
| 57 | 3-Pyridinecarboxylic acid, 2-(difluoromethyl)-4-(2-methylpropyl)-5-[(1-methyl-1H-1,2,4-triazol-5-yl)carbonyl]-6-(trifluoromethyl)-, methyl ester | 1.4868 $n_D^{25}$ |
| 58 | 3-Pyridinecarboxylic acid, 5-[(2-chloro-5-thiazolyl)carbonyl]- | 110-113 |

-continued

| Comp. No. | Name | Phys. Prop. |
|---|---|---|
| | 2-(difluoromethyl)-4-(2-methylpropyl)-6-(trifluoromethyl)-, methyl ester | |
| 59 | 3-Pyridinecarboxylic acid, 2-(difluoromethyl)-4-(2-methylpropyl)-5-[(4-methyl-2-thiazolyl)carbonyl]-6-(trifluoromethyl)-, methyl ester | 1.5091 $n_D^{25}$ |
| 60 | 3-Pyridinecarboxylic acid, 2-(difluoromethyl)-4-(2-methylpropyl)-5-[(1-methyl-1H-pyrazol-5-yl)carbonyl]-6-(trifluoromethyl)-, methyl ester | 58-64 |
| 61 | 3-Pyridinecarboxylic acid, 2-(difluoromethyl)-4-(2-methylpropyl)-5-(3-thienylcarbonyl)-6-(trifluoromethyl)-, methyl ester | 97-100 |
| 62 | 3-Pyridinecarboxylic acid, 2-(difluoromethyl)-4-(2-methylpropyl)-5-(5-thiazolylcarbonyl)-6-(trifluoromethyl)-, methyl ester | 87-90 |
| 63 | 3-Pyridinecarboxylic acid, 2-(difluoromethyl)-4-(2-methylpropyl)-5-[(4,5-dihydro-2-thiazolyl)carbonyl]-6-(trifluoromethyl)-, methyl ester | 49-57 |
| 64 | 3-Pyridinecarboxylic acid, 2-(difluoromethyl)-5-[(4,5-dihydro-2-oxazolyl)carbonyl]-4-(2-methylpropyl)-6-(trifluoromethyl)-, methyl ester | 65-70 |
| 65 | 3-Pyridinecarboxylic acid, 2-(difluoromethyl)-4-(2-methylpropyl)-5-(2-oxazolylcarbonyl)-6-(trifluoromethyl)-, methyl ester | 1.4868 $n_D^{25}$ |
| 66 | 3-Pyridinecarboxylic acid, 2-(difluoromethyl)-5-[(5-methyl-1,3,4-oxadiazol-2-yl)carbonyl]-4-(2-methylpropyl)-6-(trifluoromethyl)-, methyl ester | 62-68 |
| 67 | 3-Pyridinecarboxylic acid, 2-(difluoromethyl)-4-(2-methylpropyl)-5-(1,3,4-oxadiazol-2-ylcarbonyl)-6-(trifluoromethyl)-, methyl ester | 83-87 |
| 68 | 3-Pyridinecarboxylic acid, 6-(chlorodifluoromethyl)-2-methyl-4-(2-methylpropyl)-5-(2-thiazolylcarbonyl)-, methyl ester | 82-88 |
| 69 | 3-Pyridinecarboxylic acid, 4-(cyclopropylmethyl)-2-(difluoromethyl)-5-(2-thiazolylcarbonyl)-6-(trifluoromethyl)-, methyl ester | 66-69 |
| 70 | 3-Pyridinecarboxylic acid, 6-(difluoromethyl)-4-(2-methylpropyl)-5-(2-thiazolylcarbonyl)-2-(trifluoromethyl)-, methyl ester | 67-69 |
| 71 | 3-Pyridinecarboxylic acid, 2-(difluoromethyl)-4-(2-methylpropyl)-5-[(5-methyl-2-thiazolyl)carbonyl]-6-(trifluoromethyl)-, methyl ester | 1.5121 $n_D^{25}$ |
| 72 | Pyridinecarboxylic acid, 2-(difluoromethyl)-4-(2-methylpropyl)-5-(2-pyridinylcarbonyl)-6-(trifluoromethyl)-, methyl ester | 67-70 |
| 73 | 3-Pyridinecarboxylic acid, 2-(difluoromethyl)-4-(2-methylpropyl)-5-(3-pyridinylcarbonyl)-6-(trifluoromethyl)-, methyl ester | 86-88 |
| 74 | 3-Pyridinecarboxylic acid, 2-(difluoromethyl)-5-[[1-(methoxymethyl)-1H-imidazol-2-yl]-carbonyl]-4-(2-methylpropyl)-6-(trifluoromethyl)-, methyl ester | 94-97 |
| 75 | 3-Pyridinecarboxylic acid, 2-(difluoromethyl)-5-(1H-imidazol-2-ylcarbonyl)-4-(2-methylpropyl)-6-(trifluoromethyl)-, methyl ester | 137-140 |
| 76 | 3-Pyridinecarboxylic acid, 2-(difluoromethyl)-5-[[1-(dimethylamino)-1H-pyrrol-2-yl]-carbonyl]-4-(2-methylpropyl)-6-(trifluoromethyl)-, methyl ester | 1.5054 $n_D^{25}$ |
| 77 | 3-Pyridinecarboxylic acid, 2-(difluoromethyl)-4-(2-methylpropyl)-5-[(1-methyl-1H-tetrazole-5-yl)carbonyl]-6-(trifluoromethyl)-, methyl ester | 95-98 |
| 78 | 3-Pyridinecarboxylic acid, 2-(difluoromethyl)-5-(5-isothiazolylcarbonyl)-4-(2-methylpropyl)-6-(trifluoromethyl)-, methyl ester | 77-80 |
| 79 | 3-Pyridinecarboxylic acid, 5-[(4-bromo-2-thiazolyl)carbonyl]-2-(difluoromethyl)-4-(2-methylpropyl)-6-(trifluoromethyl)-, methyl ester | 1.5296 $n_D^{25}$ |
| 80 | 3-Pyridinecarboxylic acid, 2-(chlorodifluoromethyl)-6-(1-methylethyl)-4-(2-methylpropyl)-5-(2-thiazolylcarbonyl)-, methyl ester | 1.5289 $n_D^{25}$ |
| 81 | 3-Pyridinecarbothioic acid, 2-(difluoromethyl)-4-(2-methylpropyl)-5-(2-thiazolylcarbonyl)-6-(trifluoromethyl)-, S-methyl ester | 87-90 |
| 82 | 3-Pyridinecarboxylic acid, 2-(difluoromethyl)-4-(2-methylpropyl)-5-(2-thiazolylcarbonyl)-6-(trifluoromethyl)-, ethyl ester | 64-66 |
| 83 | 3-Pyridinecarboxylic acid, 2-(difluoromethyl)-4-(2-methylpropyl)-5-[(5-methyl-2-thienyl)carbonyl]-6-(trifluoromethyl)-, methyl ester | 95-97 |
| 84 | 3-Pyridinecarboxylic acid, 2-(difluoromethyl)-5-[[3-(methoxycarbonyl)-2-furanyl]-carbonyl]-4-(2-methylpropyl)-6-(trifluoromethyl)-, methyl ester | 1.4935 $n_D^{25}$ |
| 85 | 3-Pyridinecarboxylic acid, 5-[[3-(aminocarbonyl)-2-furanyl]carbonyl]-2-(difluoromethyl)-4-(2-methylpropyl)-6-(trifluoromethyl)-, methyl ester | 1.4990 $n_D^{25}$ |
| 86 | 3-Pyridinecarboxylic acid, 4-cyclobutyl-2-(difluoromethyl)-5-(2-thiazolylcarbonyl)-6-(trifluoromethyl)-, methyl ester | 115-117 |
| 87 | 3-Pyridinecarboxylic acid, 5-[(3-cyano-2-furanyl)carbonyl]-2-(difluoromethyl)-4-(2-methylpropyl)-6-(trifluoromethyl)-, methyl ester | 1.5013 $n_D^{25}$ |
| 88 | 3-Pyridinecarboxylic acid, 2-(difluoromethyl)-4-(2-methylpropyl)-5-(4-pyrimidinylcarbonyl)-6-(trifluoromethyl)-, methyl ester | 68-71 |
| 89 | 3-Pyridinecarboxylic acid, 5-[(3-chloro-4-pyridinyl)carbonyl]-2-(difluoromethyl)-4-(2-methylpropyl)-6-(trifluoromethyl)-, methyl ester | 1.5057 $n_D^{25}$ |
| 90 | 3-pyridinecarbothioic acid, 2-(difluoromethyl)-4-(2-methylpropyl)-5-(2-thiazolylcarbonyl)-6-(trifluoromethyl)-, S-ethyl ester | 49-52 |
| 91 | 3-Pyridinecarboxylic acid, 2-(difluoromethyl)-4-(2-methylpropyl)-5-(1H-pyrrol-2-ylcarbonyl)-6-(trifluoromethyl)-, methyl ester | 91-96 |
| 92 | 3-Pyridinecarboxylic acid, 2-(dichloromethyl)-4-(2-methylpropyl)-5-(2-thiazolylcarbonyl)-6-(trifluoromethyl)-, methyl ester | 114-118 |
| 93 | 3-Pyridinecarboxylic acid, 5-[(5-chloro-2-thiazolyl)carbonyl]-4-(2-methylpropyl)-2-(trichloromethyl)-6-(trifluoromethyl)-, methyl ester | 111-114 |
| 94 | 3-Pyridinecarboxylic acid, 2-(difluoromethyl)-5-(3,5-dimethyl-4-isoxazolylcarbonyl)-4-(2-methylpropyl)-6-(trifluoromethyl)-, methyl ester | 1.4852 $n_D^{25}$ |
| 95 | 3-Pyridinecarboxylic acid, 2-(difluoromethyl)-4-(2-methylpropyl)-5-(4-pyridinylcarbonyl)-6-(trifluoromethyl)-, methyl ester | 107-109 |
| 96 | 3-Pyridinecarboxylic acid, 2-(difluoromethyl)-5-[(5-fluoro-2- | 1.5155 $n_D^{25}$ |

-continued

| Comp. No. | Name | Phys. Prop. |
|---|---|---|
|  | pyridinyl)carbonyl]-4-(2-methylpropyl)-6-(trifluoromethyl)-, methyl ester, N-oxide |  |
| 97 | 3-Pyridinecarboxylic acid, 2-(difluoromethyl)-5-[(3-fluoro-2-pyridinyl)carbonyl]-6-(trifluoromethyl)-, methyl ester, N-oxide | 1.5213 $n_D^{25}$ |
| 98 | 3-Pyridinecarboxylic acid, 2-(difluoromethyl)-5-[(3-fluoro-2-pyridinyl)carbonyl]-4-(2-methylpropyl)-6-(trifluoromethyl)-, methyl ester | 1.4950 $n_D^{25}$ |
| 99 | 3-Pyridinecarboxylic acid, 2-(difluoromethyl)-5-[(5-fluoro-2-pyridinyl)carbonyl]-4-(2-methylpropyl)-6-(trifluoromethyl)-, methyl ester | 103–105 |
| 100 | 3-Pyridinecarboxylic acid, 5-[(5-bromo-2-thiazolyl)carbonyl]-2-(difluoromethyl)-4-(2-methylpropyl)-6-(trifluoromethyl)-, methyl ester | 109–111 |
| 101 | 3-Pyridinecarboxylic acid, 2-(difluoromethyl)-5-(3-isoxazolylcarbonyl)-4-(2-methylpropyl)-6-(trifluoromethyl)-, methyl ester | 72–72.5 |
| 102 | 3-Pyridinecarboxylic acid, 2-(difluoromethyl)-5-[(3-fluoro-1-methyl-1H-1,2,4-triazol-5-yl)carbonyl]-4-(2-methylpropyl)-6-(trifluoromethyl)-, methyl ester | 1.4797 $n_D^{25}$ |
| 103 | 3-Pyridinecarboxylic acid, 2-(difluoromethyl)-5-[(4-fluoro-2-thiazolyl)carbonyl]-4-(2-methylpropyl)-6-(trifluoromethyl)-, methyl ester | 76–77 |
| 104 | 3-Pyridinecarboxylic acid, 5-[(5-bromo-2-thienyl)carbonyl]-2-(difluoromethyl)-4-(2-methylpropyl)-6-(trifluoromethyl)-, methyl ester | 88–94 |
| 105 | 3-Pyridinecarboxylic acid, 5-(3-chloro-2-pyrazinylcarbonyl)-2-(difluoromethyl)-4-(2-methylpropyl)-6-(trifluoromethyl)-, methyl ester | 104–112 |
| 106 | 3-Pyridinecarboxylic acid, 2-(difluoromethyl)-4-(2-methylpropyl)-5-(pyrazinylcarbonyl)-6-(trifluoromethyl)-, methyl ester | 66–73 |
| 107 | 3-Pyridinecarboxylic acid, 2-(difluoromethyl)-4-(2-methylpropyl)-5-(3-pyridazinylcarbonyl)-6-(trifluoromethyl)-, methyl ester | 104–109 |
| 108 | 3-Pyridinecarboxylic acid, 5-[(3,6-dichloro-4-pyridazinyl)carbonyl]-2-(difluoromethyl)-4-(2-methylpropyl)-6-(trifluoromethyl)-, methyl ester | 76–83 |
| 109 | 3-Pyridinecarboxylic acid, 2-(difluoromethyl)-4-(2-methylpropyl)-5-(4-pyridazinylcarbonyl)-6-(trifluoromethyl)-, methyl ester | 1.5017 $n_D^{25}$ |
| 110 | 3-Pyridinecarboxylic acid, 2-(difluoromethyl)-5-[(3-fluoro-2-pyrazinyl)carbonyl]-4-(2-methylpropyl)-6-(trifluoromethyl)-, methyl ester | 1.4956 $n_D^{25}$ |

PRE-EMERGENT ACTIVITY ON PLANTS

As noted above, compounds of this invention have been found to be effective as herbicides, particularly pre-emergent herbicides. Tables A and B summarize results of tests conducted to determine the pre-emergent herbicidal activity of the compounds of this invention. The herbicidal activity data in Tables A and B are based on the percent inhibition of each tested plant species. The term "C" designates complete control of the plant species.

One set of pre-emergent tests was conducted as follows:

Topsoil was placed in a pan and compacted to a depth of 0.95 to 1.27 cm. from the top of the pan. A predetermined number of seeds of each of several monocotyledonous and dicotyledonous annual plant species and/or vegetative propagules of various perennial plant species were placed on top of the soil. The soil required to level fill a pan after seeding or adding vegetative propagules was weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amounts of active ingredient were all equivalent to an application rate of 11.21 kilograms/hectare (kg/ha). After treatment, the pans were moved to a greenhouse bench where they were watered as needed to give adequate moisture for germination and growth.

Approximately 10–14 days (usually 11 days) after planting and treating, the plants were observed and the results recorded.

The treated plant species are identified by letter headings printed vertically above the columns according to the following legend:
ANBG—Annual Bluegrass
BARZ—Barley
BLGR—Blackgrass
BYGR—Barnyardgrass
COBU—Cocklebur
COCW—Common Chickweed
COLQ—Common Lambsquarters
CORN—Corn
COTZ—Cotton
CWBS—Catchweed Bedstraw
DOBR—Downy Brome
GRFT—Green Foxtail
GRSO—Grain Sorghum
HESE—Hemp Sesbania
JIWE—Jimson Weed
LACG—Large Crabgrass
MOGL—Morningglory
PRMI—Proso Millet
PESW—Pennsylvania Smartweed
RAPE—Oilseed Rape
RICE—Rice
RUTH—Russian Thistle
SEJG—Seedling Johnsongrass
SOBE—Soybean
SUBE—Sugarbeet
VELE—Velvetleaf
WHEZ—Wheat
WIBW—Wild Buckwheat
WIOA—Wild Oats

TABLE A

| Ex. No. | Rate kg/ha | Herbicide Primary Preemergence |||||||||||||
|---|---|---|---|---|---|---|---|---|---|---|---|---|---|---|
|  |  | Yens | Anbg | Sejg | Dobr | Bygr | Mogl | Cobu | Vele | Inmu | Wibw | Cath | Colq | Pesw | Rhqg | Rhjg |
| 1 | 11.2100 | 1 | — | — | 3 | 3 | 3 | 0 | 3 | — | — | — | 3 | 3 | 3 | 3 |
| 2 | 11.2100 | 3 | — | — | 3 | 3 | 3 | 2 | 3 | — | — | — | 3 | 3 | 3 | 3 |
| 3 | 11.2100 | 0 | — | — | 0 | 3 | 0 | 0 | 1 | — | — | — | 0 | 0 | 1 | 0 |
| 4 | 11.2100 | 3 | — | — | 3 | 3 | 3 | 1 | 3 | — | — | — | 3 | 3 | 3 | 3 |

TABLE A-continued

Herbicide Primary Preemergence

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 5 | 11.2100 | 0 | — | — | 3 | 3 | 3 | 1 | 3 | — | — | — | 3 | 3 | 2 | 3 |
| 6 | 11.2100 | 1 | — | — | 3 | 3 | 1 | 0 | 1 | — | — | — | 3 | 1 | 0 | 0 |
| 7 | 11.2100 | 0 | — | — | 3 | 3 | 2 | 0 | 1 | — | — | 0 | 2 | 2 | 0 | 0 |
| 8 | 11.2100 | 3 | — | — | 3 | 3 | 3 | 3 | 3 | — | — | 3 | 3 | 3 | 3 | 3 |
| 9 | 11.2100 | 0 | — | — | 0 | 0 | 0 | 0 | 0 | — | — | 0 | 1 | 0 | 0 | N |
| 10 | 11.2100 | 1 | — | — | 3 | 3 | 3 | 2 | 3 | — | — | 3 | 3 | 3 | 3 | 3 |
| 11 | 11.2100 | 0 | — | — | 3 | 3 | 1 | 0 | 0 | — | — | 0 | 3 | 1 | 0 | 0 |
| 12 | 11.2100 | 1 | 3 | 3 | 3 | 3 | 3 | 0 | 2 | 3 | 2 | — | — | — | — | — |
| 13 | 11.2100 | 3 | 3 | 3 | 3 | 3 | 3 | 3 | 3 | 3 | 3 | — | — | — | — | — |
| 14 | 11.2100 | 3 | 3 | 3 | 3 | 3 | 3 | 3 | 3 | 3 | 3 | — | — | — | — | — |
| 15 | 11.2100 | 3 | 3 | 3 | 3 | 3 | 3 | 0 | 3 | 3 | 3 | — | — | — | — | — |
| 16 | 11.2100 | 0 | 3 | 3 | 3 | 3 | 1 | 0 | 0 | 0 | 1 | — | — | — | — | — |
| 17 | 11.2100 | 3 | 3 | 3 | 3 | 3 | 3 | 2 | 3 | 3 | 3 | — | — | — | — | — |
| 18 | 11.2100 | 3 | 3 | 3 | 3 | 3 | 3 | 0 | 3 | 3 | 3 | — | — | — | — | — |
| 19 | 11.2100 | 0 | 3 | 3 | 3 | 3 | 0 | 0 | 1 | 1 | 1 | — | — | — | — | — |
| 20 | 11.2100 | 0 | 3 | 3 | 1 | 3 | 0 | 0 | 2 | 3 | 2 | — | — | — | — | — |
| 21 | 11.2100 | 0 | 3 | 3 | 1 | 3 | 1 | 0 | 0 | 0 | 0 | — | — | — | — | — |
| 22 | 11.2100 | 0 | 0 | 0 | 0 | 2 | 0 | 0 | 1 | 0 | 2 | — | — | — | — | — |
| 23 | 11.2100 | 0 | 3 | 3 | 0 | 3 | 0 | 0 | 0 | 0 | 0 | — | — | — | — | — |
| 24 | 11.2100 | 0 | 3 | 3 | 1 | 3 | 3 | 0 | 2 | 2 | 1 | — | — | — | — | — |
| 25 | 11.2100 | 3 | 3 | 3 | 3 | 3 | 3 | 0 | 3 | 3 | 3 | — | — | — | — | — |
| 26 | 11.2100 | 1 | 3 | 3 | 3 | 3 | 3 | 1 | 3 | 3 | 3 | — | — | — | — | — |
| 27 | 11.2100 | 2 | 3 | 3 | 3 | 3 | 3 | 1 | 3 | 3 | 2 | — | — | — | — | — |
| 28 | 11.2100 | 0 | 3 | 3 | 3 | 3 | 3 | 0 | 2 | 3 | 3 | — | 2 | — | — | — |
| 29 | 11.2100 | 0 | 3 | 2 | 2 | 3 | 0 | 1 | 0 | 0 | 2 | — | — | — | — | — |
| 30 | 11.2100 | 0 | 2 | 2 | 1 | 2 | 0 | 0 | 0 | 0 | 0 | — | — | — | — | — |
| 31 | 11.2100 | 1 | 3 | 3 | 0 | 3 | 0 | 0 | 0 | 0 | 0 | — | — | — | — | — |
| 32 | 11.2100 | 2 | 3 | 3 | 3 | 3 | 3 | 0 | 3 | 3 | 3 | — | — | — | — | — |
| 33 | 11.2100 | 0 | 3 | 3 | 3 | 3 | 3 | 0 | 3 | 3 | 2 | — | — | — | — | — |
| 34 | 11.2100 | 2 | 3 | 3 | 3 | 3 | 3 | 0 | 3 | 3 | 3 | — | — | — | — | — |
| 35 | 11.2100 | 2 | 3 | 3 | 3 | 3 | 3 | 0 | 3 | 3 | 3 | — | — | — | — | — |
| 36 | 11.2100 | 3 | 3 | 3 | 3 | 3 | 3 | 1 | 3 | 3 | 3 | — | — | — | — | — |
| 37 | 11.2100 | 0 | 3 | 2 | 3 | 3 | 0 | 0 | 1 | 2 | 1 | — | — | — | — | — |
| 38 | 11.2100 | 0 | 3 | 0 | 0 | 2 | 0 | 0 | 0 | 0 | 0 | — | — | — | — | — |
| 39 | 11.2100 | 0 | 3 | 3 | 3 | 3 | 2 | 0 | 1 | 3 | 2 | — | — | — | — | — |
| 40 | 11.2100 | 0 | 3 | 3 | 3 | 3 | 2 | 0 | 2 | 3 | 3 | — | — | — | — | — |
| 41 | 11.2100 | 0 | 3 | 3 | 3 | 3 | 2 | 1 | 2 | 3 | 3 | — | — | — | — | — |
| 42 | 11.2100 | 0 | 0 | 3 | 0 | 0 | 0 | 0 | 0 | 0 | 2 | — | — | — | — | — |
| 43 | 11.2100 | 3 | 3 | 3 | 3 | 3 | 3 | 1 | 3 | 3 | 3 | — | — | — | — | — |
| 44 | 11.2100 | 0 | 3 | 3 | 3 | 3 | 2 | 1 | 2 | 3 | 3 | — | — | — | — | — |
| 45 | 11.2100 | 0 | 3 | 3 | 2 | 3 | 1 | 0 | 0 | 3 | 0 | — | — | — | — | — |
| 46 | 11.2100 | 0 | 0 | 0 | 0 | 0 | 0 | 1 | 0 | 0 | 0 | — | — | — | — | — |
| 47 | 11.2100 | 3 | 3 | 3 | 3 | 3 | 3 | 3 | 3 | 3 | 3 | — | — | — | — | — |
| 49 | 11.2100 | 3 | 3 | 3 | 3 | 3 | 3 | 2 | 3 | 3 | 3 | — | — | — | — | — |
| 50 | 11.2100 | 3 | 3 | 3 | 3 | 3 | 3 | 2 | 3 | 3 | 3 | — | — | — | — | — |
| 51 | 11.2100 | 3 | 3 | 3 | 3 | 3 | 3 | 1 | 3 | 3 | 3 | — | — | — | — | — |
| 52 | 11.2100 | 3 | 3 | 3 | 3 | 3 | 3 | 1 | 3 | 3 | 3 | — | — | — | — | — |
| 53 | 11.2100 | 80 | C | C | C | C | 90 | 50 | 90 | C | C | — | — | — | — | — |
| 54 | 11.2100 | 40 | C | C | 90 | C | 80 | 30 | 90 | C | 90 | — | — | — | — | — |
| 55 | 11.2100 | 0 | C | 90 | 60 | C | 50 | 0 | 30 | 90 | 60 | — | — | — | — | — |
| 56 | 11.2100 | C | C | C | C | C | 90 | 70 | C | C | C | — | — | — | — | — |
| 57 | 11.2100 | 90 | C | C | C | C | C | 90 | 90 | C | C | — | — | — | — | — |
| 58 | 11.2100 | 0 | 90 | 0 | 0 | 90 | 10 | 0 | 50 | 40 | 0 | — | — | — | — | — |
| 59 | 11.2100 | C | C | C | C | C | C | 90 | 80 | 90 | C | — | — | — | — | — |
| 60 | 11.2100 | C | C | C | C | C | 90 | 80 | 90 | C | C | — | — | — | — | — |
| 61 | 11.2100 | 30 | C | C | 90 | C | 80 | 50 | 90 | C | C | — | — | — | — | — |
| 62 | 11.2100 | 90 | C | C | 90 | C | 90 | 50 | C | C | C | — | — | — | — | — |
| 63 | 11.2100 | C | C | C | C | C | 90 | 80 | 90 | C | C | — | — | — | — | — |
| 64 | 11.2100 | 70 | C | C | 90 | C | C | 60 | C | C | 90 | — | — | — | — | — |
| 65 | 11.2100 | C | C | C | C | C | C | 90 | C | C | C | — | — | — | — | — |
| 66 | 11.2100 | C | C | 90 | 90 | C | 90 | 0 | 90 | C | 90 | — | — | — | — | — |
| 67 | 11.2100 | 90 | 90 | C | 90 | C | C | 70 | C | C | C | — | — | — | — | — |
| 68 | 11.2100 | 70 | C | 90 | 90 | C | 90 | 0 | 90 | C | 90 | — | — | — | — | — |
| 69 | 11.2100 | 90 | C | C | C | C | 90 | 80 | C | C | C | — | — | — | — | — |
| 70 | 11.2100 | 80 | C | C | 90 | C | 90 | 60 | 90 | C | 90 | — | — | — | — | — |
| 71 | 11.2100 | 50 | 90 | 90 | 80 | C | 80 | 70 | C | C | 90 | — | — | — | — | — |
| 72 | 11.2100 | 90 | C | C | C | C | 90 | 70 | 90 | C | C | — | — | — | — | — |
| 73 | 11.2100 | 30 | C | C | 90 | C | 80 | 30 | 80 | C | 90 | — | — | — | — | — |
| 74 | 22.4200 | 10 | C | C | C | C | C | 60 | C | C | 90 | — | — | — | — | — |
| 75 | 11.2100 | 40 | C | C | 50 | C | 80 | 20 | 90 | C | 70 | — | — | — | — | — |
| 76 | 11.2100 | C | C | C | 80 | C | 80 | 20 | 90 | C | 90 | — | — | — | — | — |
| 77 | 11.2100 | C | C | C | C | C | C | 60 | 80 | C | C | — | — | — | — | — |
| 78 | 11.2100 | 90 | C | C | 90 | C | 80 | 50 | 80 | C | 90 | — | — | — | — | — |
| 79 | 11.2100 | 50 | C | C | 80 | C | 70 | 40 | 80 | C | 90 | — | — | — | — | — |
| 80 | 11.2100 | 20 | C | C | 80 | C | 80 | 0 | 60 | C | 90 | — | — | — | — | — |
| 81 | 11.2100 | 80 | C | C | 90 | C | 90 | 90 | 90 | C | 90 | — | — | — | — | — |
| 82 | 11.2100 | 70 | C | C | 90 | C | 90 | 80 | 90 | C | 90 | — | — | — | — | — |
| 83 | 11.2100 | 0 | C | 80 | 20 | C | 50 | 30 | 50 | 90 | 30 | — | — | — | — | — |
| 84 | 11.2100 | 30 | C | C | 80 | C | 60 | 0 | 0 | 90 | 30 | — | — | — | — | — |

TABLE A-continued

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 85 | 11.2100 | 0 | 90 | 80 | 50 | C | 20 | 0 | 0 | 30 | 10 | — | — | — | — | — |
| 86 | 11.2100 | 90 | C | C | 90 | C | 90 | 60 | C | C | 90 | — | — | — | — | — |
| 87 | 11.2100 | 30 | C | C | 80 | C | 70 | 0 | 80 | C | 90 | — | — | — | — | — |
| 88 | 11.2100 | C | C | C | C | C | C | 40 | 90 | C | 90 | — | — | — | — | — |
| 89 | 11.2100 | 40 | C | 90 | 60 | C | 80 | 0 | 30 | C | 90 | — | — | — | — | — |
| 90 | 11.2100 | 90 | C | C | 90 | C | 60 | 10 | 80 | C | 80 | — | — | — | — | — |
| 91 | 11.2100 | 70 | C | C | 80 | C | 80 | 20 | 80 | C | 80 | — | — | — | — | — |
| 92 | 11.2100 | 60 | C | C | 90 | C | 80 | 60 | 80 | C | 90 | — | — | — | — | — |
| 93 | 11.2100 | 0 | 90 | 20 | 0 | 50 | 0 | 10 | 0 | 0 | 0 | — | — | — | — | — |
| 94 | 11.2100 | 0 | C | C | 30 | C | 60 | 0 | 60 | 60 | 70 | — | — | — | — | — |
| 95 | 11.2100 | 90 | C | C | 40 | C | 80 | 0 | 90 | C | 90 | — | — | — | — | — |
| 96 | 11.2100 | 0 | C | 90 | 0 | 90 | 30 | 0 | 50 | 90 | 0 | — | — | — | — | — |
| 97 | 11.2100 | 0 | C | 90 | 0 | C | 40 | 0 | 60 | 90 | 40 | — | — | — | — | — |
| 98 | 11.2100 | 90 | C | C | 60 | C | 90 | 40 | 90 | C | 90 | — | — | — | — | — |
| 99 | 11.2100 | 90 | C | 70 | C | C | 70 | 30 | 80 | C | 90 | — | — | — | — | — |
| 100 | 11.2100 | 10 | C | 50 | 40 | C | 20 | 0 | 30 | C | 90 | — | — | — | — | — |
| 101 | 11.2100 | C | C | C | C | C | C | 70 | 90 | C | C | — | — | — | — | — |
| 102 | 11.2100 | C | C | C | C | C | 90 | 80 | 90 | C | C | — | — | — | — | — |
| 103 | 11.2100 | C | C | C | C | C | 80 | 60 | 80 | C | C | — | — | — | — | — |
| 104 | 11.2100 | 0 | C | C | 80 | C | 40 | 0 | 20 | 60 | 40 | — | — | — | — | — |
| 105 | 11.2100 | 0 | 80 | 60 | 20 | 80 | 50 | 0 | 30 | 40 | 60 | — | — | — | — | — |
| 106 | 11.2100 | C | C | C | C | C | 90 | 70 | 90 | C | C | — | — | — | — | — |
| 107 | 11.2100 | C | C | C | C | C | 90 | 60 | 90 | C | C | — | — | — | — | — |
| 108 | 11.2100 | 0 | 90 | 0 | 0 | 0 | 0 | 0 | 0 | 0 | 0 | — | — | — | — | — |
| 109 | 11.2100 | 80 | C | C | 90 | C | 90 | 10 | 70 | C | 90 | — | — | — | — | — |
| 110 | 11.2100 | 0 | C | 90 | 0 | 90 | 20 | 0 | 0 | 60 | 0 | — | — | — | — | — |

C = Complete control
ND = No data
— = No test

In another set of tests, the pre-emergence activity of compounds of this invention was tested on weeds in the presence of crop plants. In these tests the following procedure was used:

Topsoil was sieved to pass through a 1.27 cm screen. Fertilizer was added to the topsoil in some of the tests, while in testing other compounds the fertilizer was omitted. The mixture was then sterilized by exposure to methyl bromide or by heating.

The topsoil mixture was placed in individual aluminum pans and compacted to a depth of about 1.27 cm. from the top of the pan. A predetermined number of seeds of each of several monocotyledonous and dicotyledonous plant species and, where noted, vegetative propagules of various perennial plant species were planted in the pans. The soil required to level fill a pan after seeding or adding vegetative propagules was weighed into another pan. A known amount of the test compound was dissolved or suspended in acetone or a suitable organic solvent as a 1% solution or suspension and applied to the cover soil using a sprayer at the desired predetermined rate. The spray was thoroughly mixed with this cover soil, and the herbicide/soil mixture was used as a cover layer for the previously prepared pan. Untreated soil was used as a cover layer for control pans. In Table B below the amount of active ingredient applied is shown. After treatment, the pans were moved to a greenhouse bench. Moisture was supplied to each pan as needed for germination and growth. Growth of each species was observed and corrective measures (greenhouse fumigation, insecticide treatment, and the like) were applied as needed. Approximately 10–14 days (usually 11 days) after planting and treating, the plants were observed and the results recorded.

The pre-emergence data for weeds in the presence of crop plants are shown in the following Table B.

TABLE B

Herbicide Secondary Preemergence
(C = 100% control)

| Ex. No. | Rate kg/ha | Sobe | Cotz | Rape | Cobu | Wibw | Mogl | Hese | Jiwe | Vele | Whez | Rice | Grso | Corn | Dobr |
|---|---|---|---|---|---|---|---|---|---|---|---|---|---|---|---|
| 1 | 5.61 | 2 | — | — | 1 | 3 | 3 | 2 | — | 2 | 3 | 3 | 3 | — | 3 |
|  | 1.12 | 0 | — | — | 0 | 1 | 2 | 0 | — | 0 | 2 | 2 | 3 | — | 3 |
|  | 0.28 | 0 | — | — | 0 | 3 | 0 | 0 | — | 0 | 0 | 0 | 0 | — | 2 |
|  | 0.06 | 0 | — | — | 0 | 0 | 0 | 0 | — | 0 | 0 | 0 | 0 | — | 0 |
|  | 0.01 | 0 | — | — | 0 | 0 | 0 | 0 | — | 0 | 0 | 0 | 0 | — | 0 |
| 2 | 5.61 | 3 | — | — | 1 | 3 | 3 | 3 | — | 3 | 3 | 3 | 3 | — | 3 |
|  | 1.12 | 2 | — | — | 0 | 3 | 2 | 1 | — | 2 | 3 | 3 | 3 | — | 3 |
|  | 0.28 | 0 | — | — | 0 | 0 | 1 | 0 | — | 0 | 3 | 2 | 2 | — | 2 |
|  | 0.06 | 0 | — | — | 0 | 0 | 0 | 0 | — | 0 | 1 | 1 | 2 | — | 2 |
|  | 0.01 | 0 | — | — | 0 | 0 | 1 | 0 | — | 0 | 0 | 1 | 0 | — | 0 |
| 3 | 5.61 | 0 | — | — | 0 | 3 | 0 | 0 | — | 0 | 0 | 0 | 0 | — | 0 |
|  | 1.12 | 0 | — | — | 0 | 1 | 0 | 0 | — | 0 | 0 | 0 | 0 | — | 0 |
| 4 | 5.61 | 3 | — | — | 1 | 3 | 3 | 3 | — | 3 | 3 | 3 | 3 | — | 3 |
|  | 1.12 | 2 | — | — | 0 | 1 | 2 | 2 | — | 1 | 3 | 3 | 3 | — | 3 |
|  | 0.28 | 0 | — | — | 0 | 1 | 2 | 2 | — | 0 | 1 | 2 | 2 | — | 1 |
|  | 0.06 | 0 | — | — | 0 | 0 | 1 | 0 | — | 0 | 0 | 0 | 0 | — | 0 |
|  | 0.01 | 0 | — | — | 0 | 0 | 0 | 0 | — | 0 | 0 | 1 | 0 | — | 0 |
| 5 | 5.61 | 2 | — | — | 0 | 2 | 1 | 2 | — | 1 | 2 | 3 | 3 | — | 2 |

TABLE B-continued

Herbicide Secondary Preemergence
(C = 100% control)

|   | Rate | 1 | 2 | 3 | 4 | 5 | 6 | 7 | 8 | 9 | 10 | 11 | 12 | 13 | 14 |
|---|------|---|---|---|---|---|---|---|---|---|----|----|----|----|----|
|   | 1.12 | 0 | — | — | 0 | 1 | 1 | 1 | — | 0 | 0  | 1  | 2  | —  | 2  |
|   | 0.28 | 0 | — | — | 0 | 0 | 0 | 0 | — | 0 | 0  | 0  | 0  | —  | 0  |
|   | 0.06 | 0 | — | — | 0 | 1 | 0 | 0 | — | 0 | 0  | 0  | 0  | —  | 0  |
| 6 | 5.61 | N | — | — | N | N | N | N | — | N | N  | N  | N  | —  | N  |
|   | 5.61 | 0 | — | — | N | 0 | 0 | 1 | — | 0 | 0  | 0  | 0  | —  | 1  |
|   | 1.12 | 0 | — | — | 0 | 0 | 0 | 0 | — | 0 | 0  | 0  | 0  | —  | 0  |
|   | 1.12 | N | — | — | N | N | N | N | — | N | N  | N  | N  | —  | N  |
|   | 0.28 | 0 | — | — | 0 | 0 | 0 | 0 | — | 0 | 0  | 0  | 0  | —  | 0  |
|   | 0.28 | N | — | — | N | N | N | N | — | N | N  | N  | N  | —  | N  |
| 7 | 1.12 | 0 | — | — | 0 | 3 | 0 | 0 | — | 0 | 0  | 0  | 1  | —  | 1  |
|   | 0.28 | 0 | — | — | 0 | 0 | 0 | 0 | — | 0 | 0  | 0  | 0  | —  | 0  |
| 8 | 5.61 | 3 | — | — | 2 | 3 | 3 | 3 | — | 3 | 3  | 3  | 3  | 3  | 3  |
|   | 1.12 | 2 | — | — | 1 | 3 | 3 | 3 | — | 3 | 3  | 3  | 3  | 3  | 3  |
|   | 0.56 | 3 | — | — | 0 | 3 | 2 | 3 | — | 3 | 3  | 3  | 3  | 3  | 3  |
|   | 0.28 | 0 | — | — | 0 | 0 | 2 | 3 | — | 3 | 3  | 3  | 3  | 3  | 3  |
|   | 0.14 | 0 | — | — | 1 | 1 | 1 | 0 | — | 2 | 3  | 3  | 3  | 1  | 3  |
|   | 0.07 | 0 | — | — | 0 | 0 | 0 | 0 | — | 1 | 2  | 3  | 3  | 0  | 3  |
|   | 0.03 | 0 | — | — | 0 | 0 | 0 | 0 | — | 0 | 1  | 2  | 3  | 0  | 3  |
|   | 0.02 | 0 | — | — | 0 | 0 | 0 | 0 | — | 0 | 0  | 0  | 2  | 0  | 3  |
|   | 0.01 | 0 | — | — | 0 | 0 | 0 | 0 | — | 0 | 0  | 0  | 0  | 0  | 2  |
| 10| 5.61 | 3 | — | — | 2 | 3 | 3 | 3 | — | 3 | 3  | 3  | 3  | 3  | 3  |
|   | 1.12 | 3 | — | — | 0 | 0 | 3 | 1 | — | 1 | 3  | 3  | 3  | 1  | 3  |
|   | 0.56 | 1 | — | — | 0 | 0 | 1 | 1 | — | 1 | 3  | 3  | 3  | 2  | 3  |
|   | 0.28 | 0 | — | — | 0 | 0 | 1 | 1 | — | 0 | 3  | 2  | 3  | 1  | 3  |
|   | 0.14 | 0 | — | — | 1 | 0 | 1 | 0 | — | 0 | 2  | 3  | 3  | 1  | 3  |
|   | 0.07 | 0 | — | — | 0 | 0 | 0 | 0 | — | 0 | 1  | 2  | 2  | 1  | 1  |
|   | 0.03 | 0 | — | — | 1 | 0 | 0 | 0 | — | 0 | 0  | 0  | 1  | 0  | 2  |
|   | 0.02 | 0 | — | — | 0 | 0 | 0 | 0 | — | 0 | 0  | 0  | 0  | 0  | 0  |
|   | 0.01 | 0 | — | — | N | 1 | 1 | 0 | — | 0 | 0  | 1  | 0  | 0  | N  |
| 11| 5.61 | 0 | — | — | 0 | 0 | 1 | 0 | — | 0 | 3  | 3  | 3  | 2  | 3  |
|   | 1.12 | 0 | — | — | 0 | 0 | 0 | N | — | 1 | 3  | 3  | 3  | 0  | 3  |
|   | 0.56 | 0 | — | — | 0 | 0 | 0 | 0 | — | 0 | 3  | 3  | 3  | 0  | 0  |
| 12| 5.61 | 3 | 0 | 0 | 0 | 0 | 3 | 0 | 0 | 2 | 3  | 3  | 3  | 3  | 3  |
|   | 1.12 | 1 | 0 | 0 | 0 | 0 | 0 | 0 | 0 | 0 | 1  | 0  | 0  | 0  | 0  |
|   | 0.28 | 0 | 0 | 0 | 0 | 0 | 0 | 0 | 0 | 0 | 1  | 0  | 0  | 0  | 0  |
|   | 0.07 | N | N | 0 | 0 | N | 0 | 0 | N | 0 | N  | N  | N  | N  | 1  |
|   | 0.02 | 0 | N | 0 | 0 | 0 | 0 | 0 | 0 | 0 | 1  | 0  | 1  | 0  | 0  |
| 13| 5.61 | 3 | 2 | 3 | 0 | 3 | 3 | 3 | 3 | 3 | 3  | 3  | 3  | 3  | 3  |
|   | 1.12 | 3 | 0 | 3 | 0 | 3 | 3 | 3 | 3 | 3 | 3  | 3  | 3  | 3  | 3  |
|   | 0.28 | 2 | 0 | 1 | 0 | 3 | 0 | 2 | 1 | 2 | 3  | 3  | 3  | 3  | 3  |
|   | 0.07 | 0 | 0 | 0 | 0 | 0 | 0 | 0 | 0 | 0 | 1  | 0  | 1  | 0  | 3  |
|   | 0.02 | 0 | N | 0 | 0 | 0 | 0 | 0 | 0 | 2 | 0  | 0  | 1  | 0  | 3  |
|   | 0.01 | 1 | 0 | 0 | 0 | 0 | 0 | 0 | 0 | 0 | 1  | 0  | 1  | 0  | 0  |
| 14| 5.61 | 3 | 3 | 3 | 3 | 3 | 3 | 3 | 3 | 3 | 3  | 3  | 3  | 3  | 3  |
|   | 1.12 | 3 | 2 | 3 | 1 | 3 | 3 | 3 | 3 | 3 | 3  | 3  | 3  | 3  | 3  |
|   | 0.28 | 3 | 0 | 2 | N | 3 | 2 | 1 | 2 | 1 | 3  | 3  | 3  | 3  | 3  |
|   | 0.07 | 1 | 0 | 2 | 0 | 1 | 2 | 1 | 1 | 0 | 3  | 3  | 3  | 3  | 3  |
|   | 0.02 | 1 | 1 | 0 | N | 0 | 0 | 0 | 0 | N | 0  | 3  | 2  | 1  | 3  |
|   | 0.01 | 0 | 0 | 0 | 0 | 0 | 0 | 0 | 0 | 0 | 0  | 2  | 0  | 0  | 0  |
| 15| 5.61 | 3 | 2 | 3 | 1 | 3 | 3 | 1 | 3 | 3 | 3  | 3  | 3  | 3  | 3  |
|   | 1.12 | 3 | 1 | 2 | 0 | 3 | 2 | 0 | 2 | 1 | 3  | 3  | 3  | 3  | 3  |
|   | 0.28 | 3 | N | 0 | 1 | 0 | 1 | 0 | 0 | 0 | 2  | 3  | 3  | 2  | 3  |
|   | 0.07 | 0 | 1 | 0 | 0 | N | 0 | 0 | N | 0 | 0  | 2  | 2  | 1  | 0  |
|   | 0.02 | 0 | 0 | 0 | 0 | 0 | 0 | 0 | 0 | 0 | 0  | 0  | 0  | 0  | 0  |
|   | 0.01 | 0 | N | 0 | 0 | 0 | 0 | 0 | N | 0 | 0  | 0  | 0  | 0  | 0  |
| 16| 5.61 | 0 | 1 | 0 | 0 | 1 | 0 | 2 | 1 | 1 | 2  | 2  | 3  | 0  | 3  |
|   | 1.12 | 1 | 0 | 0 | 0 | 1 | 0 | 1 | 0 | 0 | 0  | 1  | 1  | 1  | 0  |
|   | 0.28 | 0 | 0 | 0 | 0 | 0 | 0 | 0 | 0 | 0 | 0  | 0  | 0  | 0  | 0  |
|   | 0.07 | 0 | 0 | 1 | N | 0 | 0 | N | 0 | 0 | 0  | 1  | 0  | 0  | 0  |
| 17| 5.61 | 3 | 2 | 3 | 2 | 3 | 3 | 3 | 3 | 3 | 3  | 3  | 3  | 3  | 3  |
|   | 1.12 | 3 | 0 | 3 | 0 | 3 | 3 | 3 | 3 | 3 | 3  | 3  | 3  | 3  | 3  |
|   | 0.28 | 3 | N | 1 | 0 | 3 | 1 | 1 | 3 | 1 | 3  | 3  | 3  | 3  | 3  |
|   | 0.07 | 1 | 0 | 1 | 0 | 3 | 0 | 1 | 3 | 1 | 3  | 3  | 3  | 1  | 3  |
|   | 0.02 | 0 | 0 | 1 | 0 | 0 | 0 | 0 | 0 | 0 | 0  | 1  | 2  | 1  | 2  |
|   | 0.01 | N | 0 | 0 | 0 | 0 | 0 | 0 | 0 | 0 | 0  | 1  | 1  | 0  | 0  |
| 18| 5.61 | 1 | 0 | 3 | 0 | 3 | 2 | 3 | 3 | 3 | 3  | 3  | 3  | 3  | 3  |
|   | 5.61 | 3 | 1 | 3 | 0 | 3 | 3 | 3 | 3 | 3 | 3  | 3  | 3  | 3  | 3  |
|   | 1.12 | 3 | 1 | 1 | 0 | 3 | 3 | 2 | 3 | 3 | 3  | 3  | 3  | 3  | 3  |
|   | 1.12 | 1 | 1 | 0 | 0 | 3 | 0 | 1 | 1 | 1 | 3  | 3  | 3  | 3  | 3  |
|   | 0.28 | 0 | 1 | 0 | 0 | 3 | 0 | 1 | 3 | 3 | 1  | 3  | 3  | 3  | 3  |
|   | 0.28 | 0 | 0 | 0 | 0 | 0 | 0 | 0 | 0 | 1 | 1  | 0  | 3  | 0  | 1  |
|   | 0.07 | 0 | 0 | 0 | 0 | 0 | 0 | 0 | 0 | 0 | 0  | 0  | 0  | 0  | 0  |
|   | 0.07 | 0 | 0 | 0 | 0 | 0 | 0 | 0 | 0 | 0 | 0  | 1  | 0  | 1  | 0  |
|   | 0.02 | 0 | 0 | 0 | 0 | 0 | 0 | 0 | 0 | 0 | 0  | 0  | 1  | 1  | 0  |
|   | 0.02 | N | N | N | N | N | N | N | N | N | N  | N  | N  | N  | N  |
|   | 0.01 | N | N | N | N | N | N | N | N | N | N  | N  | N  | N  | N  |
|   | 0.01 | 0 | 0 | 0 | 0 | 0 | 0 | 2 | 0 | 1 | 0  | 0  | 0  | 0  | 0  |
| 19| 5.61 | 0 | 0 | 1 | 0 | 0 | 1 | 0 | 0 | 0 | 0  | 0  | 2  | 1  | 0  |
|   | 1.12 | 0 | 0 | 2 | 0 | 0 | 0 | 0 | 0 | 0 | 0  | 0  | 0  | 1  | 0  |
|   | 0.28 | 0 | 0 | 0 | 0 | 0 | 0 | 0 | 0 | 0 | 0  | 0  | 0  | 0  | 0  |

TABLE B-continued

Herbicide Secondary Preemergence
(C = 100% control)

| | | | | | | | | | | | | | | | |
|---|---|---|---|---|---|---|---|---|---|---|---|---|---|---|---|
| | 0.07 | 0 | 0 | 0 | 0 | 0 | 0 | 0 | 0 | 0 | 0 | 0 | 0 | 0 | 0 |
| 20 | 5.61 | 2 | 0 | 3 | 0 | 2 | 2 | 3 | 3 | 3 | 1 | 3 | 3 | 0 | 3 |
| | 1.12 | 1 | 0 | 1 | 0 | 2 | 1 | 2 | 2 | 0 | 0 | 1 | 3 | 0 | 1 |
| | 0.28 | 0 | 0 | 0 | 0 | 0 | 0 | 0 | 0 | 1 | 0 | 0 | 0 | 0 | 0 |
| | 0.07 | 0 | 0 | 0 | 0 | 0 | 0 | 0 | 0 | 0 | 0 | 0 | 0 | 0 | 0 |
| 21 | 5.61 | 0 | 0 | 0 | 0 | 0 | 0 | 0 | 0 | 0 | 0 | 0 | 0 | 0 | 0 |
| | 1.12 | 0 | 0 | 0 | 0 | 0 | 0 | N | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 |
| 23 | 5.61 | 0 | 1 | 0 | 0 | 1 | 1 | 0 | 2 | 3 | 1 | 3 | 1 | 0 | 1 |
| | 1.12 | 0 | 0 | 0 | 0 | 0 | 0 | 0 | 1 | 0 | 0 | 1 | 0 | 0 | 0 |
| | 0.28 | N | 0 | 0 | 0 | 0 | 0 | 0 | 0 | 0 | 0 | 2 | 0 | 0 | 0 |
| 24 | 5.61 | 1 | 1 | 0 | 0 | 2 | 2 | 0 | 2 | 1 | 1 | 2 | 3 | 1 | 2 |
| | 1.12 | 1 | 0 | 0 | 0 | 1 | 1 | 0 | 1 | 0 | 0 | 0 | 1 | 2 | 0 |
| | 0.28 | 0 | 0 | 1 | 0 | 1 | 0 | 0 | 0 | 0 | 0 | 1 | 0 | 0 | 0 |
| | 0.07 | 1 | 0 | N | 0 | N | 2 | 0 | 2 | N | 0 | 1 | 0 | 0 | 0 |
| 25 | 5.61 | 3 | 2 | 3 | 0 | 3 | 3 | 3 | 3 | 3 | 3 | 3 | 3 | 3 | 3 |
| | 1.12 | 2 | 0 | 3 | 0 | 2 | 3 | 1 | 2 | 2 | 3 | 3 | 3 | 3 | 3 |
| | 0.28 | 1 | 1 | 0 | 0 | 1 | 0 | 0 | 1 | 0 | 3 | 3 | 3 | 3 | 3 |
| | 0.07 | 2 | 0 | 0 | 0 | 0 | 0 | 0 | 0 | 0 | 0 | 1 | 1 | 0 | 0 |
| | 0.02 | 0 | 0 | 0 | 0 | 0 | 0 | 0 | 0 | 0 | 0 | 0 | 0 | 0 | 0 |
| | 0.01 | 0 | 0 | 0 | 0 | 0 | 0 | 0 | 0 | 0 | 0 | 0 | 0 | 0 | 0 |
| 26 | 5.61 | 3 | 3 | 3 | 1 | 3 | 3 | 3 | 3 | 3 | 3 | 3 | 3 | 3 | 3 |
| | 1.12 | 3 | 2 | 3 | 1 | 3 | 3 | 3 | 3 | 3 | 3 | 3 | 3 | 3 | 3 |
| | 0.28 | 1 | 1 | 2 | 0 | 2 | 2 | 1 | 2 | 1 | 3 | 3 | 3 | 3 | 3 |
| | 0.07 | 0 | 1 | 0 | 0 | 1 | 1 | 1 | 2 | 0 | 2 | 2 | 2 | 1 | 3 |
| | 0.02 | 0 | 0 | 0 | 0 | 0 | 0 | 0 | 1 | 0 | 2 | 1 | 1 | 0 | 2 |
| 27 | 5.61 | 3 | 2 | 3 | 1 | 3 | 3 | 3 | 3 | 3 | 3 | 3 | 3 | 3 | 3 |
| | 1.12 | 1 | 2 | 3 | 1 | 3 | 2 | 3 | 2 | 3 | 3 | 3 | 3 | 3 | 3 |
| | 0.28 | 0 | 1 | 2 | 0 | 0 | 1 | 1 | 0 | 0 | 3 | 1 | 3 | 0 | 3 |
| | 0.07 | 0 | N | 0 | 0 | 0 | 0 | 0 | 0 | 0 | 0 | 0 | 0 | 0 | 0 |
| | 0.02 | 0 | N | 0 | 0 | 0 | 0 | 0 | 0 | 0 | 0 | N | 0 | 0 | 0 |
| | 0.01 | 0 | 0 | 0 | 0 | 0 | 0 | 0 | 0 | 0 | 0 | 0 | 0 | 0 | 0 |
| 28 | 5.61 | 1 | 2 | 2 | 0 | 2 | 1 | 1 | 1 | 2 | 3 | 3 | 3 | 2 | 3 |
| | 1.12 | 0 | 1 | 0 | 0 | 0 | 0 | 0 | 0 | 0 | 0 | 0 | 1 | 0 | 0 |
| | 0.28 | 0 | 0 | 0 | 0 | 0 | 0 | 0 | 0 | 0 | 0 | 1 | 0 | 0 | 0 |
| | 0.07 | 0 | 0 | 0 | 0 | 0 | 0 | 0 | 0 | 0 | 0 | 0 | 0 | 0 | 0 |
| | 0.02 | 0 | 0 | 0 | 0 | 0 | 0 | 0 | 0 | 0 | 0 | 0 | 0 | 0 | 0 |
| 29 | 5.61 | 1 | 1 | 0 | 0 | 1 | 3 | 2 | — | 2 | 3 | 1 | 3 | 1 | 3 |
| | 1.12 | 0 | 1 | 0 | 0 | 0 | 0 | 1 | — | 1 | 0 | 0 | 1 | 0 | 0 |
| | 0.28 | N | 0 | 0 | 0 | 0 | 0 | 0 | — | 0 | 0 | 0 | 0 | 0 | 0 |
| | 0.14 | 0 | 0 | 0 | 0 | 0 | 0 | 0 | — | 0 | 0 | 0 | 0 | 0 | 0 |
| | 0.07 | 1 | 0 | 0 | 0 | 3 | 1 | 0 | — | 0 | 3 | 2 | 0 | 0 | 2 |
| 31 | 5.61 | 1 | 0 | 0 | 0 | 3 | 1 | 0 | — | 0 | 3 | 2 | 0 | 0 | 2 |
| | 1.12 | 0 | 0 | 0 | 0 | 0 | 0 | 0 | — | 0 | 1 | 2 | 0 | 0 | 0 |
| | 0.28 | 0 | 0 | 0 | 0 | 0 | 0 | 0 | — | 0 | 0 | 0 | 0 | 0 | 0 |
| | 0.07 | 0 | 0 | 0 | 0 | 0 | 0 | 0 | — | 0 | 0 | 0 | 0 | 0 | 0 |
| 32 | 5.61 | 3 | 2 | 3 | 3 | 3 | 3 | 3 | — | 3 | 3 | 3 | 3 | 3 | 3 |
| | 1.12 | 3 | 0 | 3 | 1 | 3 | 3 | 2 | — | 2 | 3 | 3 | 3 | 3 | 3 |
| | 0.28 | 1 | 0 | 1 | 0 | 2 | 0 | 0 | — | 0 | 3 | 3 | 3 | 1 | 3 |
| | 0.07 | 0 | 1 | 0 | 2 | 1 | 1 | 0 | — | 0 | 1 | 1 | 2 | 2 | 2 |
| | 0.02 | 1 | 0 | 0 | 0 | 0 | 0 | 0 | — | 0 | 0 | N | 0 | 0 | 0 |
| | 0.01 | 0 | 0 | 0 | 0 | 0 | 0 | 0 | — | 0 | 0 | 0 | 0 | 0 | 0 |
| 33 | 5.61 | 3 | 1 | 3 | 0 | 3 | 3 | 3 | — | 3 | 3 | 3 | 3 | 2 | 3 |
| | 1.12 | 1 | 0 | 3 | 0 | 3 | 2 | 2 | — | 1 | 3 | 3 | 3 | 2 | 2 |
| | 0.28 | 1 | N | 1 | 1 | 2 | 2 | 2 | — | 1 | 0 | 3 | 1 | 0 | 1 |
| | 0.07 | 1 | 0 | 1 | 0 | 0 | 0 | 0 | — | 0 | 0 | 1 | 1 | 0 | 0 |
| 34 | 5.61 | 3 | 3 | 3 | 1 | 3 | 3 | 3 | — | 3 | 3 | 3 | 3 | 3 | 3 |
| | 1.12 | 0 | 1 | 2 | 1 | 3 | 2 | 2 | — | 2 | 1 | 3 | 1 | 1 | 0 |
| | 0.28 | N | 1 | 0 | 0 | 1 | 1 | 1 | — | 0 | 0 | 0 | 0 | 0 | 0 |
| | 0.07 | 0 | 1 | 0 | 0 | 0 | 0 | 1 | — | 0 | 0 | 0 | 0 | 0 | 0 |
| | 0.02 | 1 | N | 0 | 0 | 0 | 0 | 0 | — | 0 | 0 | 0 | 0 | 0 | 0 |
| | 0.01 | N | N | 0 | 0 | 0 | 0 | 0 | — | 0 | 0 | N | 0 | 0 | 0 |
| 35 | 5.61 | 3 | 3 | 3 | 1 | 3 | 3 | 3 | — | 3 | 3 | 3 | 3 | 3 | 3 |
| | 1.12 | 3 | 3 | 3 | 0 | 3 | 3 | 3 | — | 3 | 3 | 3 | 3 | 3 | 3 |
| | 0.28 | 1 | 1 | 0 | 0 | 3 | 2 | 2 | — | 1 | 2 | 2 | 3 | 2 | 2 |
| | 0.07 | 1 | 0 | 0 | 0 | 2 | 0 | 0 | — | 0 | 0 | 0 | 1 | 0 | 0 |
| | 0.02 | 0 | 1 | 0 | 0 | 1 | N | 0 | — | 0 | 0 | 1 | 2 | 0 | 0 |
| | 0.01 | 0 | 0 | 0 | 0 | 0 | 0 | 0 | — | 0 | 0 | 0 | 0 | 0 | 0 |
| 36 | 5.61 | 3 | 3 | 3 | 1 | 3 | 3 | 3 | — | 3 | 3 | 3 | 3 | 3 | 3 |
| | 1.12 | 3 | 2 | 3 | 1 | 3 | 3 | 3 | — | 3 | 3 | 3 | 3 | 3 | 3 |
| | 0.28 | 3 | 2 | 2 | 1 | 3 | 1 | 3 | — | 3 | 2 | 3 | 3 | 2 | 3 |
| | 0.07 | 2 | 0 | 0 | 0 | 3 | 0 | 1 | — | 0 | 1 | 3 | 3 | 1 | 0 |
| | 0.02 | 0 | N | 0 | 0 | 1 | 0 | 0 | — | 0 | 0 | 3 | 3 | 1 | 0 |
| | 0.01 | 1 | 0 | 0 | 0 | 1 | 0 | 0 | — | 0 | 0 | 0 | 1 | 0 | 0 |
| 37 | 1.12 | 0 | 0 | — | N | — | 0 | — | — | 1 | — | 1 | — | 1 | — |
| | 1.21 | 0 | 0 | — | 0 | — | 0 | — | — | 1 | — | 1 | — | 1 | — |
| | 1.21 | — | — | 2 | — | 0 | — | — | — | — | 3 | — | — | — | 3 |
| | 11.21 | — | — | 3 | — | 1 | — | — | — | — | 2 | — | — | — | 3 |
| | 10.20 | 0 | 0 | — | 0 | — | 1 | — | — | 0 | — | 1 | — | 1 | — |
| | 10.20 | — | — | 3 | — | 0 | — | — | — | — | 2 | — | — | — | 2 |

TABLE B-continued

Herbicide Secondary Preemergence
(C = 100% control)

| # | Rate | 1 | 2 | 3 | 4 | 5 | 6 | 7 | 8 | 9 | 10 | 11 | 12 | 13 |
|---|------|---|---|---|---|---|---|---|---|---|----|----|----|----|
|   | 5.61 | — | — | 2 | — | 0 | — | — | — | — | 2  | —  | —  | 3 |
|   | 5.61 | — | — | 2 | — | 2 | — | — | — | — | 3  | —  | —  | 3 |
|   | 5.61 | 0 | 0 | — | 0 | — | 0 | — | — | 0 | —  | 0  | —  | 0 |
|   | 5.61 | 0 | 0 | — | 0 | — | 0 | — | — | 0 | —  | 0  | —  | 1 |
|   | 5.61 | — | — | 2 | — | 0 | — | — | — | — | 3  | —  | —  | 3 |
|   | 5.61 | — | — | 3 | — | 0 | — | — | — | — | 2  | —  | —  | 2 |
|   | 5.61 | 0 | 0 | — | 0 | — | 0 | — | — | 1 | —  | 1  | —  | 1 |
|   | 5.61 | 0 | 0 | — | 0 | — | 0 | — | — | 0 | —  | 2  | —  | 1 |
|   | 1.12 | 0 | 0 | — | 0 | — | 0 | — | — | 1 | —  | 2  | —  | 1 |
|   | 1.12 | 0 | 0 | — | 0 | — | 0 | — | — | 0 | —  | 2  | —  | 2 |
|   | 1.12 | — | — | 3 | — | 0 | — | — | — | — | N  | —  | —  | 3 |
|   | 1.12 | 0 | 0 | — | 0 | — | 0 | — | — | 0 | —  | 2  | —  | 0 |
|   | 1.12 | — | — | 2 | — | 3 | — | — | — | — | 3  | —  | —  | 3 |
|   | 1.12 | 0 | 0 | — | 0 | — | 0 | — | — | 1 | —  | 2  | —  | 1 |
|   | 1.12 | — | — | 3 | — | 2 | — | — | — | — | 3  | —  | —  | 3 |
|   | 1.12 | — | — | 3 | — | 1 | — | — | — | — | 3  | —  | —  | 3 |
|   | 0.28 | — | — | 0 | — | 0 | — | — | — | — | 2  | —  | —  | 2 |
|   | 0.28 | — | — | 2 | — | 0 | — | — | — | — | 1  | —  | —  | 1 |
|   | 0.28 | — | — | N | — | 0 | — | — | — | — | 1  | —  | —  | 3 |
|   | 0.28 | 0 | 0 | — | 0 | — | 0 | — | — | 0 | —  | 0  | —  | 0 |
|   | 0.28 | 0 | 0 | — | 0 | — | 0 | — | — | 0 | —  | 0  | —  | 0 |
|   | 0.28 | — | — | 1 | — | 0 | — | — | — | — | 2  | —  | —  | 0 |
|   | 0.28 | 0 | 0 | — | 0 | — | 0 | — | — | 0 | —  | 1  | —  | 0 |
|   | 0.28 | 0 | 0 | — | 0 | — | 0 | — | — | 0 | —  | 1  | —  | 1 |
|   | 0.07 | 0 | 0 | — | N | — | 0 | — | — | 0 | —  | 0  | —  | 0 |
|   | 0.07 | 0 | 0 | — | 0 | — | 0 | — | — | 0 | —  | 1  | —  | 0 |
|   | 0.07 | — | — | 0 | — | 0 | — | — | — | — | 0  | —  | —  | 0 |
|   | 0.07 | 0 | 0 | — | 0 | — | 0 | — | — | 0 | —  | 0  | —  | 0 |
|   | 0.07 | — | — | 0 | — | 0 | — | — | — | — | 0  | —  | —  | 0 |
|   | 0.07 | 0 | 0 | — | 0 | — | 0 | — | — | 0 | —  | 0  | —  | 0 |
|   | 0.07 | — | — | 0 | — | 0 | — | — | — | — | 0  | —  | —  | 0 |
|   | 0.07 | — | — | 1 | — | 0 | — | — | — | — | 0  | —  | —  | 0 |
|   | 0.02 | 0 | 0 | — | 0 | — | 0 | — | — | 0 | —  | 0  | —  | 0 |
|   | 0.02 | — | — | 0 | — | 0 | — | — | — | — | 0  | —  | —  | 0 |
|   | 0.02 | — | — | 0 | — | 0 | — | — | — | — | 0  | —  | —  | 0 |
|   | 0.02 | 0 | 0 | — | 0 | — | 0 | — | — | 0 | —  | 0  | —  | 0 |
| 38 | 11.21 | 0 | 0 | — | 0 | — | 0 | — | — | 0 | —  | 1  | —  | 0 |
|   | 11.21 | — | — | 0 | — | 0 | — | — | — | — | 1  | —  | —  | 0 |
|   | 5.61 | — | — | 0 | — | 0 | — | — | — | — | 0  | —  | —  | 0 |
|   | 5.61 | 0 | 0 | — | 0 | — | 0 | — | — | 0 | —  | 0  | —  | 0 |
|   | 1.12 | 0 | 0 | — | 0 | — | 0 | — | — | 0 | —  | 0  | —  | 0 |
|   | 1.12 | — | — | 0 | — | 0 | — | — | — | — | 0  | —  | —  | 0 |
| 39 | 5.61 | — | — | 2 | — | 3 | — | — | — | — | 3  | —  | —  | 2 |
|   | 5.61 | 0 | 0 | — | 0 | — | 2 | — | — | 3 | —  | 3  | —  | 3 |
|   | 1.12 | 0 | 0 | — | 0 | — | 0 | — | — | 0 | —  | 2  | —  | 1 |
|   | 1.12 | — | — | 2 | — | 3 | — | — | — | — | 3  | —  | —  | 2 |
|   | 0.28 | — | — | 0 | — | 0 | — | — | — | — | 1  | —  | —  | 1 |
|   | 0.28 | 0 | 0 | — | 0 | — | 0 | — | — | 0 | —  | 1  | —  | 0 |
|   | 0.07 | 0 | 0 | — | 0 | — | 0 | — | — | 0 | —  | 0  | —  | 0 |
|   | 0.07 | — | — | 0 | — | 0 | — | — | — | — | 0  | —  | —  | 0 |
| 40 | 5.61 | — | — | 2 | — | 3 | — | — | — | — | 3  | —  | —  | 3 |
|   | 5.61 | 2 | 0 | — | 0 | — | 2 | — | — | 3 | —  | 3  | —  | 2 |
|   | 1.12 | 0 | 0 | — | 0 | — | 0 | — | — | 2 | —  | 3  | —  | 1 |
|   | 1.12 | — | — | 2 | — | 3 | — | — | — | — | 3  | —  | —  | 2 |
|   | 0.28 | — | — | 0 | — | 3 | — | — | — | — | 1  | —  | —  | 1 |
|   | 0.28 | 0 | 0 | — | 0 | — | 0 | — | — | 0 | —  | 0  | —  | 0 |
|   | 0.07 | 0 | 0 | — | 0 | — | 0 | — | — | 0 | —  | 0  | —  | 0 |
|   | 0.07 | — | — | 0 | — | 0 | — | — | — | — | 0  | —  | —  | 0 |
| 41 | 11.21 | 3 | 1 | — | 1 | — | 3 | — | — | 3 | —  | 3  | —  | 3 |
|   | 11.21 | — | — | 3 | — | 3 | — | — | — | — | 3  | —  | —  | 3 |
|   | 5.61 | — | — | 3 | — | 3 | — | — | — | — | 3  | —  | —  | 3 |
|   | 5.61 | — | — | 3 | — | 3 | — | — | — | — | 3  | —  | —  | 3 |
|   | 5.61 | 2 | 1 | — | 0 | — | 2 | — | — | 3 | —  | 3  | —  | 2 |
|   | 5.61 | 2 | 0 | — | 0 | — | 2 | — | — | 3 | —  | 3  | —  | 3 |
|   | 1.12 | 0 | 0 | — | 0 | — | 0 | — | — | 2 | —  | 2  | —  | 1 |
|   | 1.12 | 1 | 0 | — | N | — | 0 | — | — | 1 | —  | 3  | —  | 1 |
|   | 1.12 | — | — | 2 | — | 3 | — | — | — | — | 3  | —  | —  | 1 |
|   | 1.12 | — | — | 3 | — | 3 | — | — | — | — | 3  | —  | —  | 3 |
|   | 0.28 | — | — | 1 | — | 1 | — | — | — | — | 1  | —  | —  | 0 |
|   | 0.28 | — | — | 1 | — | 0 | — | — | — | — | 1  | —  | —  | 0 |
|   | 0.28 | 0 | 0 | — | 0 | — | 0 | — | — | 0 | —  | 0  | —  | 0 |
|   | 0.28 | 1 | 0 | — | N | — | 0 | — | — | 0 | —  | 2  | —  | 1 |
|   | 0.07 | 0 | 0 | — | 0 | — | 0 | — | — | 0 | —  | 0  | —  | 0 |
|   | 0.07 | 0 | 0 | — | N | — | 0 | — | — | 0 | —  | 3  | —  | 0 |
|   | 0.07 | — | — | 2 | — | 0 | — | — | — | — | 0  | —  | —  | 0 |
|   | 0.07 | — | — | 0 | — | 1 | — | — | — | — | 0  | —  | —  | 0 |
|   | 0.02 | — | — | 0 | — | 0 | — | — | — | — | 0  | —  | —  | 0 |
|   | 0.02 | 0 | 0 | — | N | — | 1 | — | — | 0 | —  | 1  | —  | 0 |
| 42 | 11.21 | 0 | 0 | 0 | 0 | 0 | 0 | 0 | — | 0 | 0  | 0  | 0  | 0 |
|   | 5.61 | 0 | 0 | 0 | 0 | 0 | 0 | 0 | — | 0 | 0  | 0  | 0  | 0 |

TABLE B-continued

Herbicide Secondary Preemergence  
(C = 100% control)

| # | Rate | C1 | C2 | C3 | C4 | C5 | C6 | C7 | C8 | C9 | C10 | C11 | C12 | C13 | C14 |
|---|------|----|----|----|----|----|----|----|----|----|-----|-----|-----|-----|-----|
| 43 | 1.12 | 0 | 0 | 0 | 0 | 0 | 0 | 0 | — | 0 | 0 | 0 | 0 | 0 | 0 |
|  | 5.61 | — | — | 3 | — | 3 | — | — | — | — | 3 | — | — | — | 3 |
|  | 5.61 | 3 | 2 | — | 1 | — | 3 | — | — | 3 | — | 3 | — | 3 | — |
|  | 1.12 | 3 | 1 | — | 0 | — | 3 | — | — | 3 | — | 3 | — | 3 | — |
|  | 1.12 | — | — | 3 | — | 3 | — | — | — | — | 3 | — | — | — | 3 |
|  | 0.28 | — | — | 3 | — | 3 | — | — | — | — | 3 | — | — | — | 3 |
|  | 0.28 | 0 | 0 | — | 1 | — | 3 | — | — | 3 | — | 3 | — | 2 | — |
|  | 0.07 | 0 | 0 | — | 0 | — | 1 | — | — | 1 | — | 2 | — | 0 | — |
|  | 0.07 | — | — | 2 | — | 2 | — | — | — | — | 2 | — | — | — | 2 |
|  | 0.02 | — | — | 0 | — | 0 | — | — | — | — | 0 | — | — | — | 0 |
|  | 0.02 | 0 | 0 | — | 0 | — | 0 | — | — | 0 | — | 1 | — | 0 | — |
|  | 0.00 | 0 | 0 | — | 0 | — | 0 | — | — | 0 | — | 0 | — | 0 | — |
|  | 0.00 | — | — | 0 | — | 0 | — | — | — | — | 0 | — | — | — | 0 |
| 44 | 5.61 | — | — | 3 | — | 3 | — | — | — | — | 3 | — | — | — | 3 |
|  | 5.61 | 3 | 3 | — | 1 | — | 3 | — | — | 3 | — | 3 | — | 3 | — |
|  | 1.12 | 0 | 0 | — | 0 | — | 0 | — | — | 2 | — | 2 | — | 1 | — |
|  | 1.12 | — | — | 2 | — | 1 | — | — | — | — | 3 | — | — | — | 3 |
|  | 0.28 | — | — | 2 | — | N | — | — | — | — | 3 | — | — | — | 0 |
|  | 0.28 | 0 | 0 | — | 0 | — | 0 | — | — | 2 | — | 2 | — | 2 | — |
|  | 0.07 | 0 | 0 | — | 0 | — | 0 | — | — | 0 | — | 0 | — | 0 | — |
|  | 0.07 | — | — | 1 | — | 0 | — | — | — | — | 1 | — | — | — | 0 |
|  | 0.02 | — | — | 0 | — | 0 | — | — | — | — | 0 | — | — | — | 0 |
|  | 0.02 | 0 | 0 | — | 0 | — | 0 | — | — | 0 | — | 0 | — | 0 | — |
| 45 | 5.61 | 0 | 0 | — | 0 | — | 0 | — | — | 2 | — | 3 | — | 1 | — |
|  | 5.61 | — | — | 2 | — | 3 | — | — | — | — | 2 | — | — | — | 3 |
|  | 1.12 | — | — | 0 | — | 1 | — | — | — | — | 0 | — | — | — | 0 |
|  | 1.12 | 0 | 0 | — | 0 | — | 0 | — | — | 0 | — | 1 | — | 0 | — |
|  | 0.28 | 0 | 0 | — | 0 | — | 0 | — | — | 0 | — | 0 | — | 0 | — |
|  | 0.28 | — | — | 0 | — | 0 | — | — | — | — | 0 | — | — | — | 0 |
|  | 0.07 | — | — | 0 | — | 0 | — | — | — | — | 0 | — | — | — | 0 |
|  | 0.07 | 0 | 0 | — | 0 | — | 0 | — | — | 0 | — | 0 | — | 0 | — |
| 47 | 5.61 | 3 | 3 | — | N | — | 3 | — | — | 3 | — | 3 | — | 3 | — |
|  | 5.61 | — | — | 3 | — | 3 | — | — | — | — | 3 | — | — | — | 3 |
|  | 1.12 | — | — | 3 | — | 3 | — | — | — | — | 3 | — | — | — | 3 |
|  | 1.12 | 3 | 2 | — | N | — | 3 | — | — | 3 | — | 3 | — | 3 | — |
|  | 0.28 | 2 | 0 | — | N | — | 1 | — | — | 2 | — | 3 | — | 2 | — |
|  | 0.28 | — | — | 3 | — | 3 | — | — | — | — | 3 | — | — | — | 3 |
|  | 0.07 | — | — | 2 | — | 0 | — | — | — | — | 2 | — | — | — | 3 |
|  | 0.07 | 0 | 0 | — | N | — | 0 | — | — | 0 | — | 3 | — | 1 | — |
|  | 0.02 | 0 | 0 | — | N | — | 0 | — | — | 0 | — | 1 | — | 0 | — |
|  | 0.02 | — | — | 0 | — | 2 | — | — | — | — | 0 | — | — | — | 2 |
|  | 0.00 | — | — | 0 | — | 0 | — | — | — | — | 0 | — | — | — | 0 |
|  | 0.00 | 0 | 0 | — | N | — | 0 | — | — | 0 | — | 0 | — | 0 | — |
| 49 | 5.61 | — | — | 3 | — | 3 | — | — | — | — | 3 | — | — | — | 3 |
|  | 5.61 | 3 | 3 | — | 2 | — | 3 | — | — | 3 | — | 3 | — | 3 | — |
|  | 1.12 | 3 | 1 | — | 0 | — | 3 | — | — | 3 | — | 3 | — | 3 | — |
|  | 1.12 | — | — | 3 | — | 3 | — | — | — | — | 3 | — | — | — | 3 |
|  | 0.28 | — | — | 3 | — | 3 | — | — | — | — | 3 | — | — | — | 3 |
|  | 0.28 | 3 | 0 | — | 0 | — | 2 | — | — | 3 | — | 3 | — | 3 | — |
|  | 0.07 | 2 | 0 | — | 0 | — | 1 | — | — | 3 | — | 2 | — | 3 | — |
|  | 0.07 | — | — | 3 | — | 3 | — | — | — | — | 3 | — | — | — | 3 |
|  | 0.02 | — | — | 0 | — | 3 | — | — | — | — | 2 | — | — | — | 3 |
|  | 0.02 | 0 | 0 | — | 0 | — | 0 | — | — | 2 | — | 0 | — | 1 | — |
|  | 0.00 | 0 | 0 | — | 0 | — | 0 | — | — | 0 | — | 0 | — | 0 | — |
|  | 0.00 | — | — | 0 | — | 2 | — | — | — | — | 0 | — | — | — | 0 |
| 50 | 5.61 | — | — | 3 | — | 3 | — | — | — | — | 3 | — | — | — | 3 |
|  | 5.61 | 3 | 3 | — | 1 | — | 3 | — | — | 3 | — | 3 | — | 3 | — |
|  | 1.12 | 3 | 0 | — | 0 | — | 3 | — | — | 3 | — | 3 | — | 3 | — |
|  | 1.12 | — | — | 3 | — | 3 | — | — | — | — | 3 | — | — | — | 3 |
|  | 0.28 | — | — | 3 | — | 3 | — | — | — | — | 3 | — | — | — | 3 |
|  | 0.28 | 0 | 0 | — | 0 | — | 2 | — | — | 3 | — | 3 | — | 3 | — |
|  | 0.07 | 0 | 0 | — | 0 | — | 1 | — | — | 1 | — | 1 | — | 2 | — |
|  | 0.07 | — | — | 1 | — | 1 | — | — | — | — | 3 | — | — | — | 2 |
|  | 0.02 | — | — | 0 | — | 1 | — | — | — | — | 0 | — | — | — | 0 |
|  | 0.02 | 0 | 0 | — | 0 | — | 0 | — | — | 0 | — | 0 | — | 0 | — |
|  | 0.00 | 0 | 0 | — | 0 | — | 0 | — | — | 0 | — | 0 | — | 0 | — |
|  | 0.00 | — | — | 0 | — | 0 | — | — | — | — | 0 | — | — | — | 0 |
| 51 | 5.61 | — | — | 3 | — | 3 | — | — | — | — | 3 | — | — | — | 3 |
|  | 5.61 | 3 | 1 | — | 0 | — | 3 | — | — | 3 | — | 3 | — | 3 | — |
|  | 1.12 | 1 | 0 | — | 0 | — | 3 | — | — | 3 | — | 3 | — | 3 | — |
|  | 1.12 | — | — | 3 | — | 3 | — | — | — | — | 3 | — | — | — | 3 |
|  | 0.28 | — | — | 2 | — | 2 | — | — | — | — | 3 | — | — | — | 3 |
|  | 0.28 | 0 | 0 | — | 0 | — | 0 | — | — | 1 | — | 2 | — | 1 | — |
|  | 0.07 | 0 | 0 | — | 0 | — | 0 | — | — | 0 | — | 0 | — | 0 | — |
|  | 0.07 | — | — | 0 | — | 2 | — | — | — | — | 0 | — | — | — | 0 |
|  | 0.02 | — | — | 0 | — | 2 | — | — | — | — | 0 | — | — | — | 0 |
|  | 0.02 | 0 | 0 | — | 0 | — | 0 | — | — | 0 | — | 0 | — | 0 | — |
|  | 0.00 | 0 | 0 | — | 0 | — | 0 | — | — | 0 | — | 0 | — | 0 | — |
|  | 0.00 | — | — | 0 | — | 2 | — | — | — | — | 0 | — | — | — | 0 |
| 52 | 5.61 | — | — | 3 | — | 3 | — | — | — | — | 3 | — | — | — | 3 |

TABLE B-continued

Herbicide Secondary Preemergence
(C = 100% control)

| | | | | | | | | | | | | | | | |
|---|---|---|---|---|---|---|---|---|---|---|---|---|---|---|---|
| | 5.61 | 3 | 3 | — | 2 | — | 3 | — | — | 3 | — | 3 | — | 3 | — |
| | 1.12 | 3 | 1 | — | 0 | — | 3 | — | — | 3 | — | 3 | — | 3 | — |
| | 1.12 | — | — | 3 | — | 3 | — | — | — | — | 3 | — | — | — | 3 |
| | 0.28 | — | — | 3 | — | 3 | — | — | — | — | 3 | — | — | — | 3 |
| | 0.28 | 3 | 0 | — | 0 | — | 2 | — | — | 3 | — | 3 | — | 3 | — |
| | 0.07 | 0 | 0 | — | 0 | — | 0 | — | — | 3 | — | 3 | — | 0 | — |
| | 0.07 | — | — | 2 | — | 3 | — | — | — | — | 2 | — | — | — | 3 |
| | 0.02 | — | — | 0 | — | 2 | — | — | — | — | 0 | — | — | — | 2 |
| | 0.02 | 0 | 0 | — | 0 | — | 0 | — | — | 0 | — | 1 | — | 0 | — |
| | 0.00 | 0 | 0 | — | 0 | — | 0 | — | — | 0 | — | 0 | — | 0 | — |
| | 0.00 | — | — | 0 | — | 0 | — | — | — | — | 0 | — | — | — | 0 |
| 53 | 5.61 | 3 | 3 | 3 | N | 3 | 3 | 3 | 3 | 3 | 3 | 3 | 3 | 3 | 3 |
| | 1.12 | 3 | 2 | 3 | N | 3 | 3 | 3 | 3 | 3 | 3 | 3 | 3 | 2 | 3 |
| | 0.28 | 3 | 1 | 3 | N | 3 | 2 | 2 | 3 | 3 | 3 | 3 | 3 | 2 | 3 |
| | 0.07 | 1 | 0 | 2 | N | 2 | 0 | 2 | 1 | 0 | 2 | 3 | 1 | 0 | 1 |
| | 0.02 | N | 0 | 0 | N | 0 | 0 | 0 | 1 | 1 | 0 | 2 | 0 | 0 | 0 |
| | 0.01 | N | N | 0 | N | N | 0 | 0 | 0 | 0 | 0 | N | 0 | 0 | N |
| 54 | 5.61 | 3 | 3 | 3 | 0 | 3 | 3 | 3 | 3 | 3 | 3 | 3 | 3 | 3 | 3 |
| | 1.12 | 3 | 2 | 3 | 0 | 3 | 3 | 3 | 3 | 3 | 3 | 3 | 3 | 3 | 3 |
| | 0.28 | 2 | 2 | 3 | 0 | 3 | 3 | 2 | 2 | 1 | 3 | 3 | 3 | 2 | 3 |
| | 0.07 | 2 | 1 | 1 | 0 | 1 | 2 | 1 | 1 | 0 | 2 | 2 | 2 | 1 | 3 |
| | 0.02 | 1 | 0 | 0 | 0 | 1 | 0 | 0 | 1 | 0 | 1 | 1 | 1 | 0 | 2 |
| | 0.01 | 1 | 0 | 0 | 0 | 0 | 0 | 0 | 0 | 0 | 1 | 0 | 0 | 0 | 0 |
| 55 | 5.61 | 3 | 1 | 3 | 0 | 3 | 3 | 3 | — | 3 | 3 | 3 | 3 | 3 | 3 |
| | 1.12 | 3 | 0 | 2 | 0 | 2 | 3 | 2 | — | 3 | 2 | 1 | 1 | 0 | 2 |
| | 0.28 | 0 | 0 | 0 | 0 | 1 | 1 | 2 | — | 1 | 0 | 0 | 0 | 0 | 1 |
| | 0.07 | 0 | 0 | 0 | 0 | 0 | 0 | 0 | — | 0 | 0 | 0 | 0 | 0 | 0 |
| 56 | 5.61 | 3 | 3 | 3 | 3 | 3 | 3 | 3 | — | 3 | 3 | 3 | 3 | 3 | 3 |
| | 1.12 | 3 | 3 | 3 | 3 | 3 | 3 | 3 | — | 3 | 3 | 3 | 3 | 3 | 3 |
| | 0.28 | 3 | 3 | 3 | 1 | 3 | 3 | 3 | — | 3 | 3 | 3 | 3 | 3 | 3 |
| | 0.07 | 3 | 2 | 3 | 1 | 3 | 3 | 3 | — | 3 | 2 | 3 | 3 | 2 | 3 |
| | 0.02 | 3 | 0 | 3 | 0 | 3 | 3 | 3 | — | 3 | 2 | 1 | 3 | 1 | 3 |
| | 0.01 | 2 | 0 | 3 | 0 | 3 | 1 | 2 | — | 2 | 1 | 0 | 1 | 0 | 3 |
| 57 | 5.61 | 3 | 2 | 3 | 3 | 3 | 3 | 3 | — | 3 | 3 | 3 | 3 | 3 | 3 |
| | 1.12 | 3 | 0 | 3 | 0 | 3 | 3 | 2 | — | 3 | 3 | 3 | 3 | 3 | 3 |
| | 0.28 | 3 | 0 | 3 | 0 | 3 | 3 | 2 | — | 3 | 3 | 2 | 3 | 3 | 3 |
| | 0.07 | 3 | 0 | 3 | 0 | 3 | 3 | 3 | — | 3 | 3 | 2 | 3 | 2 | 3 |
| | 0.02 | 1 | 0 | 2 | 0 | 2 | 1 | 3 | — | 2 | 1 | 2 | 3 | 0 | 3 |
| | 0.01 | 0 | 0 | 0 | 0 | 1 | 1 | 0 | — | 1 | 2 | 1 | 3 | 0 | 1 |
| 58 | 11.21 | 1 | 1 | 3 | 0 | 2 | 0 | 0 | — | 0 | 0 | 1 | 0 | 0 | 0 |
| | 5.61 | 1 | 0 | 3 | 0 | 2 | 0 | 0 | — | 1 | 0 | 0 | 1 | 0 | 0 |
| | 1.12 | N | 0 | 3 | 0 | 1 | 0 | 0 | — | 0 | 0 | 1 | 1 | 1 | 0 |
| 59 | 5.61 | 3 | 3 | 3 | 3 | 3 | 3 | 3 | — | 3 | 3 | 3 | 3 | 3 | 3 |
| | 1.12 | 3 | 2 | 3 | 2 | 3 | 3 | 3 | — | 3 | 3 | 3 | 3 | 3 | 3 |
| | 0.28 | 1 | 1 | 3 | 1 | 3 | 0 | 3 | — | 3 | 3 | 2 | 3 | 1 | 3 |
| | 0.07 | 0 | 1 | 3 | 0 | 3 | N | 2 | — | 2 | 2 | 0 | 2 | 1 | 3 |
| | 0.02 | 0 | 0 | 0 | 0 | 1 | 0 | 0 | — | 0 | 2 | N | 2 | 0 | 1 |
| | 0.00 | 0 | 0 | 0 | 0 | 0 | 0 | 0 | — | 0 | 0 | 0 | 0 | 0 | 0 |
| 60 | 5.61 | 3 | 3 | 3 | 2 | 3 | 3 | 3 | — | 3 | 3 | 3 | 3 | 3 | 3 |
| | 1.12 | 2 | 0 | 3 | 0 | 3 | 3 | 3 | — | 3 | 3 | 3 | 3 | 3 | 3 |
| | 0.28 | 0 | 0 | 0 | N | 3 | 0 | 3 | — | 2 | 2 | 3 | 3 | 0 | 2 |
| | 0.07 | 0 | 1 | 0 | 0 | 1 | 0 | 0 | — | 0 | 0 | 0 | 3 | 0 | 0 |
| | 0.02 | N | 0 | 0 | 0 | 0 | 0 | 0 | — | 0 | 0 | 1 | 0 | 0 | 0 |
| | 0.00 | 0 | 0 | 0 | 0 | N | 0 | 0 | — | 0 | 0 | 0 | 0 | 0 | 0 |
| 61 | 5.61 | 3 | 2 | 3 | 2 | 3 | 3 | 3 | — | 3 | 3 | 3 | 3 | 3 | 3 |
| | 1.12 | 2 | 1 | 3 | 2 | 3 | 3 | 3 | — | 3 | 3 | 3 | 3 | 2 | 3 |
| | 0.28 | 1 | 1 | 3 | 0 | 3 | 1 | 2 | — | 2 | 3 | 2 | 2 | 1 | 3 |
| | 0.07 | 0 | 0 | 0 | 1 | 0 | 0 | 0 | — | 1 | 0 | 1 | 1 | 0 | 1 |
| | 0.02 | 0 | 0 | 0 | 0 | 0 | 0 | 0 | — | 0 | 0 | 0 | 0 | 0 | 0 |
| 62 | 5.61 | 3 | 3 | 3 | 2 | 3 | 3 | 3 | — | 3 | 3 | 3 | 3 | 2 | 3 |
| | 1.12 | 3 | 2 | 3 | 1 | 3 | 3 | 3 | — | 3 | 3 | 3 | 3 | 1 | 3 |
| | 0.28 | 2 | 0 | 3 | 1 | 3 | 2 | 2 | — | 1 | 2 | 3 | 3 | 1 | 2 |
| | 0.07 | 0 | 0 | 3 | 1 | 1 | 1 | 0 | — | 0 | 1 | 1 | 1 | 0 | 1 |
| | 0.02 | 1 | 0 | 2 | 1 | 0 | 1 | 0 | — | N | 1 | 0 | 0 | 0 | 0 |
| | 0.01 | 0 | 0 | 1 | 0 | 0 | 0 | 0 | — | 0 | 1 | 0 | 0 | 0 | 0 |
| 63 | 5.61 | 3 | 3 | 3 | 3 | 3 | 3 | 3 | — | 3 | 3 | 3 | 3 | 3 | 3 |
| | 1.12 | 3 | 3 | 3 | 3 | 3 | 3 | 3 | — | 3 | 3 | 3 | 3 | 3 | 3 |
| | 0.28 | 3 | 2 | 3 | 1 | 3 | 3 | 3 | — | 3 | 3 | 3 | 3 | 1 | 3 |
| | 0.07 | 2 | 2 | 2 | 1 | 3 | 3 | 2 | — | 2 | 3 | 3 | 2 | 1 | 3 |
| | 0.02 | 2 | 0 | 0 | 1 | 2 | 2 | 0 | — | 0 | 1 | 0 | 0 | 1 | 3 |
| | 0.01 | 0 | N | 0 | 0 | 1 | 0 | 0 | — | 1 | 0 | 1 | 0 | 1 | 1 |
| 64 | 5.61 | 3 | 2 | 3 | 1 | 3 | 3 | 3 | — | 3 | 3 | 3 | 3 | 3 | 3 |
| | 1.12 | 1 | 2 | 0 | 1 | 1 | 3 | 1 | — | 0 | 1 | 1 | 2 | 0 | 0 |
| | 0.28 | 0 | 1 | 0 | 0 | 0 | 0 | 0 | — | 0 | 0 | 1 | 0 | 0 | 0 |
| | 0.07 | 0 | 0 | 0 | 0 | 0 | 0 | 0 | — | 0 | 0 | 0 | 0 | 0 | 0 |
| | 0.02 | 0 | 0 | 0 | 0 | 0 | 0 | 0 | — | 0 | 0 | 0 | 0 | 0 | 0 |
| | 0.01 | 0 | 0 | 0 | 0 | 0 | 0 | 0 | — | 0 | 0 | 0 | 0 | 0 | 0 |
| 65 | 5.61 | 3 | 3 | 3 | 3 | 3 | 3 | 3 | — | 3 | 3 | 3 | 3 | 3 | 3 |
| | 1.12 | 3 | 2 | 3 | 1 | 3 | 3 | 3 | — | 3 | 3 | 3 | 3 | 3 | 3 |
| | 0.28 | 3 | 1 | 3 | 1 | 3 | 3 | 3 | — | 3 | 3 | 3 | 3 | 3 | 3 |

TABLE B-continued

Herbicide Secondary Preemergence
(C = 100% control)

| Cmpd | Rate | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| | 0.07 | 2 | 1 | 2 | 0 | 3 | 3 | 2 | — | 3 | 2 | 2 | 2 | 2 | 3 |
| | 0.02 | 1 | 0 | 0 | 0 | 3 | 2 | 1 | — | 0 | 0 | 1 | 0 | 0 | 1 |
| | 0.00 | 0 | 0 | 0 | 0 | 1 | 0 | 0 | — | 0 | 0 | 1 | 0 | 0 | 0 |
| 66 | 5.61 | 3 | 3 | 3 | 0 | 3 | 3 | 3 | — | 3 | 3 | 3 | 3 | 3 | 3 |
| | 1.12 | 1 | 0 | 2 | 0 | 3 | 1 | 2 | — | 2 | 3 | 3 | 3 | 2 | 3 |
| | 0.28 | 0 | 1 | 0 | 0 | 1 | 0 | 2 | — | 0 | 1 | 1 | 2 | 0 | 0 |
| | 0.07 | 0 | 1 | 0 | 0 | 2 | 0 | 0 | — | 0 | 0 | 0 | 0 | 0 | 0 |
| | 0.02 | 0 | 0 | 0 | 0 | 1 | 0 | 0 | — | 0 | 0 | 0 | 0 | 0 | 0 |
| | 0.01 | 0 | 0 | 0 | 0 | N | 0 | 0 | — | 0 | 0 | 0 | 0 | 0 | 1 |
| 67 | 5.61 | 3 | 2 | 3 | 1 | 3 | 3 | 3 | — | 3 | 2 | 3 | 3 | 1 | 3 |
| | 1.12 | 2 | 1 | 3 | 0 | 3 | 3 | 2 | — | 3 | 0 | 1 | 1 | 0 | 1 |
| | 0.28 | 1 | 1 | 3 | 0 | 3 | 3 | 1 | — | 3 | 0 | 2 | 0 | 0 | 1 |
| | 0.07 | 0 | 0 | 0 | 0 | 2 | 0 | 0 | — | 0 | 0 | 0 | 0 | 0 | 0 |
| | 0.02 | 0 | 1 | 0 | 0 | 1 | 0 | 0 | — | 1 | 0 | 0 | 0 | 0 | 0 |
| | 0.01 | 0 | 1 | 0 | 0 | 0 | 0 | 1 | — | 1 | 1 | 1 | 0 | 0 | 0 |
| 68 | 5.61 | 3 | 2 | 3 | 1 | 3 | 3 | 3 | — | 3 | 3 | 3 | 3 | 3 | 3 |
| | 1.12 | 2 | 2 | 3 | 0 | 2 | 3 | 2 | — | 2 | 3 | 0 | 3 | 1 | 3 |
| | 0.28 | 0 | 0 | 1 | 0 | 1 | 3 | 0 | — | 0 | 1 | 0 | 1 | 0 | 1 |
| | 0.07 | 0 | 1 | 0 | 0 | 1 | 0 | 0 | — | 0 | 1 | 1 | 0 | 0 | 0 |
| | 0.02 | 0 | 1 | 0 | 0 | 0 | 0 | 0 | — | 0 | 0 | 0 | 0 | 0 | 0 |
| | 0.01 | 0 | 0 | 0 | 0 | 0 | 0 | 0 | — | 0 | N | 0 | 0 | 0 | 0 |
| 69 | 5.61 | 3 | 3 | 3 | 3 | 3 | 3 | 3 | — | 3 | 3 | 3 | 3 | 3 | 3 |
| | 1.12 | 3 | 3 | 3 | 1 | 3 | 3 | 3 | — | 3 | 3 | 2 | 3 | 3 | 3 |
| | 0.28 | 3 | 1 | 3 | 1 | 3 | 3 | 3 | — | 3 | 3 | 2 | 3 | 1 | 3 |
| | 0.07 | 0 | 2 | 2 | 0 | 3 | 3 | 3 | — | 3 | 2 | 0 | 2 | 0 | 2 |
| | 0.02 | 0 | 1 | 2 | 0 | 2 | 2 | 1 | — | 2 | 1 | N | 0 | 1 | 2 |
| | 0.01 | 0 | 1 | 1 | 0 | 1 | 1 | 0 | — | 0 | 1 | 1 | 0 | N | 1 |
| 70 | 5.61 | 3 | 3 | 3 | 0 | 3 | 3 | 3 | — | 3 | 3 | 3 | 3 | 3 | 3 |
| | 1.12 | 2 | 0 | 3 | 0 | 3 | 2 | 3 | — | 3 | 3 | 3 | 3 | 2 | 2 |
| | 0.28 | 1 | 0 | 3 | 0 | 3 | 1 | 1 | — | 1 | 3 | 2 | 3 | 0 | 2 |
| | 0.07 | 0 | 1 | 0 | 0 | 1 | 0 | 0 | — | 0 | 1 | 2 | 0 | 1 | 1 |
| | 0.02 | 0 | N | 0 | 0 | 0 | 1 | 1 | — | 0 | 1 | 0 | 0 | 0 | 0 |
| | 0.01 | 0 | N | 0 | 0 | 1 | 0 | 0 | — | 1 | 0 | N | 0 | 0 | 1 |
| 71 | 5.61 | 3 | 2 | 3 | 1 | 3 | 3 | 3 | — | 3 | 3 | 3 | 3 | 3 | 3 |
| | 1.12 | 2 | 0 | 3 | 0 | 3 | 3 | 2 | — | 2 | 3 | 2 | 3 | 3 | 3 |
| | 0.28 | 0 | 0 | 0 | 0 | 2 | 0 | 0 | — | 1 | 1 | 0 | 2 | 1 | 1 |
| | 0.07 | 0 | 1 | 0 | 0 | 1 | 0 | 1 | — | 1 | 1 | N | 0 | 0 | 1 |
| | 0.02 | N | 0 | 0 | 0 | 0 | 0 | 0 | — | 1 | 0 | 0 | 0 | 0 | 0 |
| 72 | 5.61 | — | — | 3 | — | 3 | — | — | — | — | 3 | — | — | — | 3 |
| | 5.61 | 3 | 3 | — | 2 | — | 3 | — | — | 3 | — | 3 | — | 3 | — |
| | 1.12 | 3 | 2 | — | 1 | — | 3 | — | — | 3 | — | 3 | — | 3 | — |
| | 1.12 | — | — | 3 | — | 3 | — | — | — | — | 3 | — | — | — | 3 |
| | 0.28 | — | — | 3 | — | 3 | — | — | — | — | 3 | — | — | — | 3 |
| | 0.28 | 3 | 0 | — | 0 | — | 2 | — | — | 3 | — | 3 | — | 3 | — |
| | 0.07 | 2 | 0 | — | 0 | — | 3 | — | — | 3 | — | 3 | — | 1 | — |
| | 0.07 | — | — | 2 | — | 3 | — | — | — | — | 3 | — | — | — | 3 |
| | 0.02 | — | — | 1 | — | 3 | — | — | — | — | 1 | — | — | — | 0 |
| | 0.02 | 0 | 0 | — | 0 | — | 0 | — | — | 0 | — | 1 | — | 0 | — |
| | 0.00 | 0 | 0 | — | 0 | — | 0 | — | — | 0 | — | 0 | — | 0 | — |
| | 0.00 | — | — | 1 | — | 1 | — | — | — | — | 0 | — | — | — | 0 |
| 73 | 5.61 | — | — | 3 | — | 3 | — | — | — | — | 3 | — | — | — | 3 |
| | 5.61 | 3 | 3 | — | 2 | — | 3 | — | — | 3 | — | 3 | — | 3 | — |
| | 1.12 | 3 | 2 | — | 2 | — | 3 | — | — | 3 | — | 3 | — | 3 | — |
| | 1.12 | — | — | 3 | — | 3 | — | — | — | — | 3 | — | — | — | 3 |
| | 0.28 | — | — | 3 | — | 3 | — | — | — | — | 2 | — | — | — | 2 |
| | 0.28 | 2 | 0 | — | 0 | — | 0 | — | — | 0 | — | 3 | — | 1 | — |
| | 0.07 | 1 | 0 | — | 0 | — | 1 | — | — | 1 | — | 2 | — | 0 | — |
| | 0.07 | — | — | 2 | — | 3 | — | — | — | — | 2 | — | — | — | 0 |
| | 0.02 | — | — | 2 | — | 0 | — | — | — | — | 0 | — | — | — | 0 |
| | 0.02 | 0 | 0 | — | 0 | — | 0 | — | — | 0 | — | 1 | — | 0 | — |
| 74 | 5.61 | 3 | 2 | 3 | 0 | 3 | 3 | 3 | — | 3 | 3 | 3 | 3 | 3 | 3 |
| | 1.12 | 3 | 2 | 3 | 2 | 3 | 3 | 2 | — | 3 | 3 | 3 | 3 | 3 | 3 |
| | 0.28 | 2 | 0 | 1 | 0 | 3 | 2 | 2 | — | 3 | 3 | 1 | 3 | 2 | 3 |
| | 0.07 | 0 | 0 | 0 | 0 | 1 | 0 | 1 | — | 1 | 3 | 0 | 3 | 1 | 0 |
| | 0.02 | 0 | 0 | N | 0 | 0 | 0 | 0 | — | 0 | 2 | 0 | 3 | 0 | 0 |
| | 0.01 | 0 | 0 | 0 | 0 | 0 | 0 | 0 | — | 0 | 1 | 0 | 0 | 0 | 0 |
| 75 | 5.61 | 3 | 2 | 1 | 1 | 3 | 3 | 2 | — | 3 | 3 | 2 | 3 | 3 | 3 |
| | 1.12 | 3 | 2 | 0 | 0 | 3 | 2 | 3 | — | 3 | 3 | 2 | 3 | 2 | 3 |
| | 0.28 | 0 | 0 | 0 | 0 | 3 | 0 | 0 | — | 1 | 3 | 1 | 3 | 2 | 1 |
| | 0.07 | 0 | 0 | N | 0 | 0 | 0 | 0 | — | 0 | 1 | 0 | 1 | 0 | 0 |
| 76 | 5.61 | 3 | 0 | 3 | 0 | 3 | 2 | 0 | — | 3 | 3 | 3 | 3 | 3 | 3 |
| | 1.12 | 3 | 0 | 1 | 0 | 2 | 0 | 1 | — | 2 | 3 | 1 | 3 | 2 | 3 |
| | 0.28 | 0 | 0 | 0 | 0 | 1 | 0 | 0 | — | 0 | 3 | 0 | 1 | 0 | 2 |
| | 0.07 | 0 | 0 | 0 | 0 | 0 | 0 | 0 | — | 0 | 0 | 0 | 0 | 0 | 0 |
| | 0.02 | 0 | 0 | 0 | 1 | 0 | 0 | 0 | — | 0 | 0 | 0 | 0 | 0 | 0 |
| | 0.01 | 0 | 0 | 0 | 0 | N | 0 | N | — | N | 0 | N | 0 | 0 | 0 |
| 77 | 5.61 | 3 | 2 | 3 | 1 | 3 | 3 | 3 | — | 3 | 3 | 3 | 3 | 3 | 3 |
| | 1.12 | 3 | 2 | 3 | 0 | 3 | 3 | 2 | — | 3 | 3 | 3 | 3 | 2 | 3 |
| | 0.28 | 2 | 2 | 3 | 0 | 3 | 0 | 0 | — | 1 | 3 | 3 | 3 | 0 | 3 |
| | 0.07 | 1 | 1 | 1 | 0 | 0 | 0 | 0 | — | 0 | 0 | 1 | 1 | 0 | 0 |

TABLE B-continued

Herbicide Secondary Preemergence
(C = 100% control)

|    |      |   |   |   |   |   |   |   |   |   |   |   |   |   |   |
|----|------|---|---|---|---|---|---|---|---|---|---|---|---|---|---|
|    | 0.02 | 1 | 1 | 0 | 0 | 2 | 0 | 0 | — | 0 | 0 | 0 | 0 | 0 | 0 |
|    | 0.01 | 2 | 1 | 0 | 0 | 0 | 0 | 0 | — | 0 | 0 | 0 | 0 | 0 | 0 |
| 78 | 5.61 | 3 | 0 | — | 0 | — | 3 | — | — | 3 | — | 3 | — | 3 | — |
|    | 5.61 | — | — | 3 | — | 3 | — | — | — | — | 3 | — | — | — | 3 |
|    | 1.12 | — | — | 3 | — | 2 | — | — | — | — | 3 | — | — | — | 3 |
|    | 1.12 | 1 | 0 | — | 0 | — | 2 | — | — | 2 | — | 2 | — | 1 | — |
|    | 0.28 | 0 | 0 | — | 0 | — | 1 | — | — | 0 | — | 1 | — | 0 | — |
|    | 0.28 | — | — | 2 | — | 2 | — | — | — | — | 2 | — | — | — | 3 |
|    | 0.07 | — | — | 2 | — | 0 | — | — | — | — | 1 | — | — | — | 1 |
|    | 0.07 | 0 | 0 | — | 0 | — | 0 | — | — | 0 | — | 0 | — | 0 | — |
|    | 0.02 | 0 | 0 | — | 0 | — | 0 | — | — | 0 | — | 0 | — | 0 | — |
|    | 0.02 | — | — | 0 | — | 0 | — | — | — | — | 0 | — | — | — | 0 |
|    | 0.01 | — | — | 0 | — | 0 | — | — | — | — | 0 | — | — | — | 0 |
|    | 0.01 | 0 | 0 | — | 0 | — | 0 | — | — | 0 | — | 0 | — | 0 | — |
| 79 | 5.61 | 3 | 2 | — | 1 | — | 3 | — | — | 3 | — | 3 | — | 3 | — |
|    | 5.61 | — | — | 3 | — | 3 | — | — | — | — | 3 | — | — | — | 3 |
|    | 1.12 | — | — | 3 | — | 3 | — | — | — | — | 3 | — | — | — | 3 |
|    | 1.12 | 2 | 1 | — | 0 | — | 3 | — | — | 2 | — | 3 | — | 2 | — |
|    | 0.28 | 0 | 0 | — | 0 | — | 0 | — | — | 1 | — | 2 | — | 0 | — |
|    | 0.28 | — | — | 2 | — | 3 | — | — | — | — | 2 | — | — | — | 2 |
|    | 0.07 | — | — | 0 | — | 2 | — | — | — | — | 1 | — | — | — | 0 |
|    | 0.07 | 0 | 0 | — | 0 | — | 0 | — | — | 0 | — | 0 | — | 0 | — |
|    | 0.02 | 0 | 0 | — | 0 | — | 0 | — | — | 0 | — | 0 | — | 1 | — |
|    | 0.02 | — | — | 0 | — | 0 | — | — | — | — | 0 | — | — | — | 0 |
|    | 0.00 | — | — | 0 | — | 0 | — | — | — | — | 0 | — | — | — | 0 |
|    | 0.00 | 0 | 0 | — | 0 | — | 0 | — | — | 0 | — | 0 | — | 0 | — |
| 80 | 5.61 | 2 | 1 | — | 0 | — | 3 | — | — | 3 | — | 2 | — | 2 | — |
|    | 5.61 | — | — | 3 | — | 3 | — | — | — | — | 3 | — | — | — | 3 |
|    | 1.12 | — | — | 3 | — | 3 | — | — | — | — | 3 | — | — | — | 3 |
|    | 1.12 | 0 | 0 | — | 1 | — | 1 | — | — | 1 | — | 2 | — | 0 | — |
|    | 0.28 | 0 | 0 | — | 0 | — | 0 | — | — | 0 | — | 0 | — | 0 | — |
|    | 0.28 | — | — | 1 | — | 3 | — | — | — | — | 2 | — | — | — | 1 |
|    | 0.07 | — | — | 0 | — | 1 | — | — | — | — | 0 | — | — | — | 0 |
|    | 0.07 | 0 | 0 | — | 0 | — | 0 | — | — | 0 | — | 0 | — | 0 | — |
|    | 0.02 | 0 | 0 | — | 0 | — | 0 | — | — | 0 | — | 0 | — | 0 | — |
|    | 0.02 | — | — | 0 | — | 0 | — | — | — | — | 0 | — | — | — | 0 |
| 81 | 5.61 | — | — | 3 | — | 3 | — | — | — | — | 3 | — | — | — | 3 |
|    | 5.61 | 3 | 3 | — | 2 | — | 3 | — | — | 3 | — | 3 | — | 3 | — |
|    | 1.12 | 3 | 3 | — | 1 | — | 3 | — | — | 3 | — | 3 | — | 3 | — |
|    | 1.12 | — | — | 3 | — | 3 | — | — | — | — | 3 | — | — | — | 3 |
|    | 0.28 | — | — | 3 | — | 3 | — | — | — | — | 3 | — | — | — | 3 |
|    | 0.28 | 2 | 1 | — | 0 | — | 3 | — | — | 3 | — | 3 | — | 1 | — |
|    | 0.07 | 0 | 0 | — | 0 | — | 0 | — | — | 2 | — | 1 | — | 0 | — |
|    | 0.07 | — | — | 3 | — | 3 | — | — | — | — | 2 | — | — | — | 2 |
|    | 0.02 | — | — | 3 | — | 2 | — | — | — | — | 2 | — | — | — | 1 |
|    | 0.02 | 0 | 0 | — | 0 | — | 0 | — | — | 0 | — | 0 | — | 0 | — |
|    | 0.00 | 0 | 0 | — | 0 | — | 0 | — | — | 0 | — | 0 | — | 0 | — |
|    | 0.00 | — | — | 1 | — | 1 | — | — | — | — | 0 | — | — | — | 0 |
| 82 | 5.61 | — | — | 3 | — | 3 | — | — | — | — | 3 | — | — | — | 3 |
|    | 5.61 | 3 | 3 | — | 2 | — | 3 | — | — | 3 | — | 3 | — | 3 | — |
|    | 1.12 | 3 | 3 | — | 0 | — | 3 | — | — | 3 | — | 3 | — | 3 | — |
|    | 1.12 | — | — | 3 | — | 3 | — | — | — | — | 3 | — | — | — | 3 |
|    | 0.28 | — | — | 3 | — | 3 | — | — | — | — | 3 | — | — | — | 3 |
|    | 0.28 | 2 | 1 | — | 0 | — | 1 | — | — | 3 | — | 2 | — | 1 | — |
|    | 0.07 | 0 | 0 | — | 0 | — | 0 | — | — | 2 | — | 1 | — | 1 | — |
|    | 0.07 | — | — | 3 | — | 3 | — | — | — | — | 3 | — | — | — | 3 |
|    | 0.02 | — | — | 2 | — | 2 | — | — | — | — | 0 | — | — | — | 1 |
|    | 0.02 | 0 | 0 | — | 0 | — | 0 | — | — | 0 | — | 0 | — | 0 | — |
|    | 0.00 | 0 | 0 | — | 0 | — | 0 | — | — | 0 | — | 0 | — | 0 | — |
|    | 0.00 | — | — | 0 | — | 0 | — | — | — | — | 0 | — | — | — | 0 |
| 83 | 5.61 | 1 | 1 | — | N | — | 1 | — | — | 2 | — | 3 | — | 2 | — |
|    | 5.61 | — | — | 3 | — | 3 | — | — | — | — | 3 | — | — | — | 3 |
|    | 1.12 | — | — | 2 | — | 3 | — | — | — | — | 2 | — | — | — | 3 |
|    | 1.12 | 0 | 0 | — | N | — | 1 | — | — | 1 | — | 3 | — | 0 | — |
|    | 0.28 | 0 | 0 | — | N | — | 0 | — | — | 0 | — | 1 | — | 1 | — |
|    | 0.28 | — | — | 1 | — | 1 | — | — | — | — | 1 | — | — | — | 1 |
|    | 0.07 | — | — | 0 | — | 0 | — | — | — | — | 0 | — | — | — | 0 |
|    | 0.07 | 0 | 0 | — | 1 | — | 0 | — | — | 0 | — | 0 | — | 0 | — |
| 84 | 5.61 | 0 | 0 | — | 2 | — | 2 | — | — | 1 | — | 3 | — | 0 | — |
|    | 5.61 | — | — | 3 | — | 3 | — | — | — | — | 2 | — | — | — | 3 |
|    | 1.12 | — | — | 1 | — | 3 | — | — | — | — | 0 | — | — | — | 1 |
|    | 1.12 | 0 | 0 | — | 0 | — | 0 | — | — | 0 | — | 1 | — | 0 | — |
|    | 0.28 | 0 | 0 | — | 0 | — | 0 | — | — | 0 | — | 0 | — | 0 | — |
|    | 0.28 | — | — | 0 | — | 0 | — | — | — | — | 0 | — | — | — | 0 |
|    | 0.07 | — | — | 0 | — | 0 | — | — | — | — | 0 | — | — | — | 0 |
|    | 0.07 | 0 | 0 | — | 0 | — | 0 | — | — | 0 | — | 0 | — | 0 | — |
|    | 0.02 | 0 | 0 | — | 0 | — | 0 | — | — | 0 | — | 0 | — | 0 | — |
|    | 0.02 | — | — | 0 | — | 0 | — | — | — | — | 0 | — | — | — | 0 |
| 85 | 5.61 | — | — | 3 | — | 3 | — | — | — | — | 0 | — | — | — | 3 |
|    | 5.61 | 1 | 0 | — | 0 | — | 3 | — | — | 1 | — | 0 | — | 2 | — |

TABLE B-continued

Herbicide Secondary Preemergence
(C = 100% control)

| # | Rate | | | | | | | | | | | | | |
|---|------|---|---|---|---|---|---|---|---|---|---|---|---|---|
| | 1.12 | 0 | 0 | — | 0 | — | 0 | — | — | 0 | — | 0 | — | 1 | — |
| | 1.12 | — | — | 0 | — | 0 | — | — | — | — | 0 | — | — | — | 0 |
| | 0.28 | — | — | 0 | — | 0 | — | — | — | — | 0 | — | — | — | 0 |
| | 0.28 | 0 | 0 | — | 0 | — | 0 | — | — | 0 | — | 0 | — | 0 | — |
| | 0.07 | 0 | 0 | — | 0 | — | 0 | — | — | 0 | — | 0 | — | 0 | — |
| | 0.07 | — | — | 1 | — | 0 | — | — | — | — | 0 | — | — | — | 0 |
| 86 | 5.61 | — | — | 3 | — | 3 | — | — | — | — | 3 | — | — | — | 3 |
| | 5.61 | 3 | 3 | — | 3 | — | 3 | — | — | 3 | — | 3 | — | 3 | — |
| | 1.12 | — | — | 3 | — | 3 | — | — | — | — | 3 | — | — | — | 3 |
| | 1.12 | 3 | 3 | — | 2 | — | 3 | — | — | 3 | — | 3 | — | 3 | — |
| | 0.28 | 3 | 1 | — | 0 | — | 3 | — | — | 3 | — | 3 | — | 3 | — |
| | 0.28 | — | — | 3 | — | 3 | — | — | — | — | 3 | — | — | — | 3 |
| | 0.07 | 0 | 0 | — | 0 | — | 0 | — | — | 2 | — | 1 | — | 0 | — |
| | 0.07 | — | — | 3 | — | 3 | — | — | — | — | 2 | — | — | — | 2 |
| | 0.02 | — | — | 1 | — | 1 | — | — | — | — | 0 | — | — | — | 0 |
| | 0.02 | 0 | 0 | — | 0 | — | 0 | — | — | 0 | — | 0 | — | 0 | — |
| | 0.00 | 0 | 0 | — | 0 | — | 0 | — | — | 0 | — | 0 | — | 0 | — |
| | 0.00 | — | — | 0 | — | 0 | — | — | — | — | 0 | — | — | — | 0 |
| 87 | 5.61 | — | — | 3 | — | 3 | — | — | — | — | 3 | — | — | — | 3 |
| | 5.61 | 3 | 2 | — | 1 | — | 3 | — | — | 3 | — | 3 | — | 3 | — |
| | 1.12 | — | — | 3 | — | 3 | — | — | — | — | 3 | — | — | — | 3 |
| | 1.12 | 1 | 0 | — | 1 | — | 3 | — | — | 3 | — | 2 | — | 2 | — |
| | 0.28 | — | — | 3 | — | 2 | — | — | — | — | 2 | — | — | — | 3 |
| | 0.28 | 0 | 0 | — | 0 | — | 3 | — | — | 3 | — | 2 | — | 2 | — |
| | 0.07 | — | — | 0 | — | 0 | — | — | — | — | 0 | — | — | — | 0 |
| | 0.07 | 0 | 0 | — | 0 | — | 0 | — | — | 1 | — | 0 | — | 0 | — |
| | 0.02 | — | — | 0 | — | 0 | — | — | — | — | 0 | — | — | — | 0 |
| | 0.02 | 0 | 0 | — | 0 | — | 0 | — | — | 0 | — | 0 | — | 0 | — |
| 88 | 10.20 | 3 | 3 | — | 2 | — | 3 | — | — | 3 | — | 3 | — | 3 | — |
| | 10.20 | — | — | 3 | — | 3 | — | — | — | — | 3 | — | — | — | 3 |
| | 5.61 | — | — | 3 | — | 3 | — | — | — | — | 3 | — | — | — | 3 |
| | 5.61 | 3 | 3 | — | 2 | — | 3 | — | — | 3 | — | 3 | — | 3 | — |
| | 1.12 | — | — | 3 | — | 3 | — | — | — | — | 3 | — | — | — | 3 |
| | 1.12 | 3 | 0 | — | 0 | — | 3 | — | — | 3 | — | 3 | — | 3 | — |
| | 0.28 | 0 | 0 | — | 0 | — | 2 | — | — | 1 | — | 3 | — | 1 | — |
| | 0.28 | — | — | 3 | — | 1 | — | — | — | — | 2 | — | — | — | 3 |
| | 0.07 | 0 | 0 | — | 0 | — | 0 | — | — | 0 | — | 1 | — | 0 | — |
| | 0.07 | — | — | 3 | — | 1 | — | — | — | — | 1 | — | — | — | 2 |
| | 0.02 | — | — | 0 | — | 0 | — | — | — | — | 0 | — | — | — | 2 |
| | 0.02 | 0 | 0 | — | 0 | — | 0 | — | — | 0 | — | 0 | — | 0 | — |
| 89 | 5.61 | — | — | 3 | — | 3 | — | — | — | — | 3 | — | — | — | 3 |
| | 5.61 | 1 | 0 | — | 0 | — | 3 | — | — | 0 | — | 1 | — | 2 | — |
| | 1.12 | 0 | 0 | — | 0 | — | 1 | — | — | 0 | — | 0 | — | 0 | — |
| | 1.12 | — | — | 3 | — | 2 | — | — | — | — | 2 | — | — | — | 2 |
| | 0.28 | — | — | 0 | — | 1 | — | — | — | — | 0 | — | — | — | 0 |
| | 0.28 | 0 | 0 | — | 0 | — | 1 | — | — | 0 | — | 0 | — | 0 | — |
| | 0.07 | 0 | 0 | — | 0 | — | 0 | — | — | 0 | — | 0 | — | 0 | — |
| | 0.07 | — | — | 0 | — | 0 | — | — | — | — | 0 | — | — | — | 0 |
| | 0.02 | 0 | 0 | — | 0 | — | 0 | — | — | 0 | — | 0 | — | 0 | — |
| | 0.02 | — | — | 0 | — | 0 | — | — | — | — | 0 | — | — | — | 0 |
| 90 | 5.61 | — | — | 3 | — | 3 | — | — | — | — | 3 | — | — | — | 3 |
| | 5.61 | 3 | 3 | — | 1 | — | 3 | — | — | 3 | — | 3 | — | 3 | — |
| | 1.12 | 1 | 2 | — | 0 | — | 3 | — | — | 3 | — | 2 | — | 2 | — |
| | 1.12 | — | — | 3 | — | 3 | — | — | — | — | 3 | — | — | — | 3 |
| | 0.28 | 0 | 0 | — | 0 | — | 2 | — | — | 1 | — | 0 | — | 1 | — |
| | 0.28 | — | — | 3 | — | 3 | — | — | — | — | 3 | — | — | — | 3 |
| | 0.07 | — | — | 3 | — | 2 | — | — | — | — | 1 | — | — | — | 2 |
| | 0.07 | 0 | 0 | — | 0 | — | 0 | — | — | 0 | — | 0 | — | 0 | — |
| | 0.02 | 0 | 0 | — | 0 | — | 0 | — | — | 0 | — | 0 | — | 0 | — |
| | 0.02 | — | — | 0 | — | 0 | — | — | — | — | 0 | — | — | — | 1 |
| | 0.00 | — | — | 0 | — | 0 | — | — | — | — | 0 | — | — | — | 0 |
| | 0.00 | 0 | 0 | — | 0 | — | 0 | — | — | 0 | — | 1 | — | 0 | — |
| 91 | 5.61 | — | — | 3 | — | 3 | — | — | — | — | 3 | — | — | — | 3 |
| | 5.61 | 3 | 3 | — | 1 | — | 3 | — | — | 3 | — | 3 | — | 3 | — |
| | 1.12 | — | — | 3 | — | 3 | — | — | — | — | 1 | — | — | — | 3 |
| | 1.12 | 1 | 0 | — | 1 | — | 3 | — | — | 3 | — | 2 | — | 2 | — |
| | 0.28 | — | — | 3 | — | 2 | — | — | — | — | 1 | — | — | — | 1 |
| | 0.28 | 0 | 0 | — | 0 | — | 3 | — | — | 1 | — | 1 | — | 0 | — |
| | 0.07 | 0 | 0 | — | 0 | — | 0 | — | — | 0 | — | 0 | — | 0 | — |
| | 0.07 | — | — | 1 | — | 0 | — | — | — | — | 0 | — | — | — | 0 |
| | 0.02 | 0 | 0 | — | 0 | — | 0 | — | — | 0 | — | 0 | — | 0 | — |
| | 0.02 | — | — | 1 | — | 1 | — | — | — | — | 0 | — | — | — | 0 |
| 92 | 5.61 | 3 | 3 | — | 2 | — | 3 | — | — | 3 | — | 3 | — | 2 | — |
| | 5.61 | — | — | 3 | — | 3 | — | — | — | — | 3 | — | — | — | 3 |
| | 1.12 | — | — | 3 | — | 3 | — | — | — | — | 3 | — | — | — | 3 |
| | 1.12 | 2 | 2 | — | 1 | — | 3 | — | — | 3 | — | 3 | — | 1 | — |
| | 0.28 | 1 | 1 | — | 0 | — | 3 | — | — | 3 | — | 1 | — | 1 | — |
| | 0.28 | — | — | 3 | — | 3 | — | — | — | — | 1 | — | — | — | 2 |
| | 0.07 | — | — | 3 | — | 3 | — | — | — | — | 1 | — | — | — | 2 |
| | 0.07 | 0 | 0 | — | 0 | — | 0 | — | — | 2 | — | 1 | — | 0 | — |

TABLE B-continued

Herbicide Secondary Preemergence
(C = 100% control)

| | Rate | | | | | | | | | | | | | | |
|---|---|---|---|---|---|---|---|---|---|---|---|---|---|---|---|
| | 0.02 | — | — | 3 | — | 2 | — | — | — | — | 1 | — | — | — | 0 |
| | 0.02 | 0 | 0 | — | 0 | — | 0 | — | — | 0 | — | 0 | — | 0 | — |
| 93 | 11.21 | — | — | 0 | — | 1 | — | — | — | — | 1 | — | — | — | 2 |
| | 11.21 | 0 | 0 | — | 0 | — | 0 | — | — | 0 | — | 0 | — | 0 | — |
| | 5.61 | — | — | 0 | — | 0 | — | — | — | — | 0 | — | — | — | 2 |
| | 5.61 | 0 | 0 | — | 0 | — | 0 | — | — | 0 | — | 0 | — | 0 | — |
| | 1.12 | — | — | 0 | — | 0 | — | — | — | — | 0 | — | — | — | 0 |
| | 1.12 | 0 | 0 | — | 0 | — | 0 | — | — | 0 | — | 0 | — | 0 | — |
| 94 | 5.61 | — | — | 3 | — | 3 | — | — | — | — | 3 | — | — | — | 3 |
| | 5.61 | 0 | 0 | — | 0 | — | 3 | — | — | 1 | — | 3 | — | 3 | — |
| | 1.12 | 0 | 0 | — | 0 | — | 0 | — | — | 0 | — | 1 | — | 0 | — |
| | 1.12 | — | — | 0 | — | 1 | — | — | — | — | 0 | — | — | — | 0 |
| | 0.28 | — | — | 0 | — | 0 | — | — | — | — | 0 | — | — | — | 0 |
| | 0.28 | 0 | 0 | — | 0 | — | 0 | — | — | 0 | — | 0 | — | 0 | — |
| | 0.07 | — | — | 0 | — | 0 | — | — | — | — | 0 | — | — | — | 0 |
| | 0.07 | 0 | 0 | — | 0 | — | 0 | — | — | 0 | — | 0 | — | 0 | — |
| 95 | 10.20 | — | — | 3 | — | 3 | — | — | — | — | 3 | — | — | — | 3 |
| | 10.20 | 3 | 3 | — | 0 | — | 3 | — | — | 3 | — | 3 | — | 3 | — |
| | 5.61 | — | — | 3 | — | 3 | — | — | — | — | 3 | — | — | — | 3 |
| | 5.61 | 3 | 2 | — | 1 | — | 3 | — | — | 3 | — | 3 | — | 3 | — |
| | 1.12 | — | — | 3 | — | 1 | — | — | — | — | 1 | — | — | — | 3 |
| | 1.12 | 0 | 0 | — | 0 | — | 1 | — | — | 3 | — | 2 | — | 1 | — |
| | 0.28 | 0 | 0 | — | 0 | — | 2 | — | — | 2 | — | 2 | — | 0 | — |
| | 0.28 | — | — | 2 | — | 1 | — | — | — | — | 0 | — | — | — | 0 |
| | 0.07 | 0 | 0 | — | 0 | — | 0 | — | — | 0 | — | 0 | — | 0 | — |
| | 0.07 | — | — | 1 | — | 0 | — | — | — | — | 0 | — | — | — | 0 |
| | 0.02 | — | — | 0 | — | 0 | — | — | — | — | 0 | — | — | — | 0 |
| | 0.02 | 0 | 0 | — | 0 | — | 0 | — | — | 0 | — | 0 | — | 0 | — |
| 96 | 10.20 | — | — | 3 | — | 1 | — | — | — | — | 1 | — | — | — | 2 |
| | 10.20 | 0 | 0 | — | 2 | — | 3 | — | — | 1 | — | 3 | — | 1 | — |
| | 5.61 | — | — | 3 | — | 0 | — | — | — | — | 0 | — | — | — | 0 |
| | 5.61 | 0 | 0 | — | 0 | — | 1 | — | — | 0 | — | 1 | — | 0 | — |
| | 1.12 | — | — | 1 | — | 1 | — | — | — | — | 0 | — | — | — | 0 |
| | 1.12 | 0 | 0 | — | 0 | — | 1 | — | — | 2 | — | 2 | — | 0 | — |
| | 0.28 | — | — | 0 | — | 0 | — | — | — | — | 0 | — | — | — | 0 |
| | 0.28 | 0 | · | — | 0 | — | 0 | — | — | 0 | — | 0 | — | 0 | — |
| | 0.07 | — | — | 1 | 0 | — | — | — | — | 0 | — | — | — | — | 0 |
| | 0.07 | 0 | 0 | — | 0 | — | 0 | — | — | 0 | — | 0 | — | 0 | — |
| | 0.02 | — | — | 0 | — | 0 | — | — | — | — | 0 | — | — | — | 0 |
| | 0.02 | 0 | 0 | — | 0 | — | 0 | — | — | 0 | — | 0 | — | 0 | — |
| 97 | 10.20 | — | — | 3 | — | 3 | — | — | — | — | 0 | — | — | — | 3 |
| | 10.20 | 0 | 0 | — | 0 | — | 2 | — | — | 2 | — | 1 | — | 1 | — |
| | 5.61 | — | — | 3 | — | 1 | — | — | — | — | 0 | — | — | — | 2 |
| | 5.61 | 0 | 0 | — | 0 | — | 1 | — | — | 1 | — | 0 | — | 0 | — |
| | 1.12 | — | — | 1 | — | 0 | — | — | — | — | 0 | — | — | — | 0 |
| | 1.12 | 0 | 0 | — | 0 | — | 0 | — | — | 0 | — | 0 | — | 0 | — |
| | 0.28 | — | — | 0 | — | 0 | — | — | — | — | 0 | — | — | — | 0 |
| | 0.28 | 0 | 0 | — | 0 | — | 0 | — | — | 0 | — | 0 | — | 0 | — |
| | 0.07 | 0 | 0 | — | 0 | — | 0 | — | — | 0 | — | 0 | — | 0 | — |
| | 0.07 | — | — | 1 | — | 0 | — | — | — | — | 0 | — | — | — | 0 |
| | 0.02 | 0 | 0 | — | 0 | — | 0 | — | — | 0 | — | 0 | — | 0 | — |
| | 0.02 | — | — | N | — | 0 | — | — | — | — | 0 | — | — | — | 0 |
| 98 | 10.20 | 3 | 3 | — | 2 | — | 3 | — | — | 3 | — | 3 | — | 3 | — |
| | 10.20 | — | — | 3 | — | 3 | — | — | — | — | 3 | — | — | — | 3 |
| | 5.61 | 3 | 3 | — | 3 | — | 3 | — | — | 3 | — | 3 | — | 3 | — |
| | 5.61 | — | — | 3 | — | 3 | — | — | — | — | 3 | — | — | — | 3 |
| | 1.12 | 3 | 2 | — | 1 | — | 3 | — | — | 3 | — | 3 | — | 3 | — |
| | 1.12 | — | — | 3 | — | 3 | — | — | — | — | 3 | — | — | — | 3 |
| | 0.28 | — | — | 3 | — | 3 | — | — | — | — | 1 | — | — | — | 3 |
| | 0.28 | 1 | 0 | — | 1 | — | 3 | — | — | 3 | — | 2 | — | 2 | — |
| | 0.07 | — | — | 3 | — | 3 | — | — | — | — | 0 | — | — | — | 2 |
| | 0.07 | 0 | 0 | — | 0 | — | 0 | — | — | 0 | — | 0 | — | 1 | — |
| | 0.02 | — | — | 3 | — | 1 | — | — | — | — | 0 | — | — | — | 1 |
| | 0.02 | 0 | 0 | — | 0 | — | 2 | — | — | 0 | — | 0 | — | 0 | — |
| 99 | 10.20 | — | — | 3 | — | 3 | — | — | — | — | 3 | — | — | — | 3 |
| | 0.00 | 1 | 1 | — | 1 | — | 13 | — | — | 3 | — | 3 | — | 3 | — |
| | 5.61 | — | — | 3 | — | 3 | — | — | — | — | 3 | — | — | — | 3 |
| | 5.61 | 2 | 0 | — | 0 | — | 3 | — | — | 3 | — | 3 | — | 3 | — |
| | 1.12 | — | — | 3 | — | 3 | — | — | — | — | 2 | — | — | — | 3 |
| | 1.12 | 0 | 0 | — | 0 | — | 3 | — | — | 3 | — | 3 | — | 1 | — |
| | 0.28 | 0 | 0 | — | 1 | — | 1 | — | — | 1 | — | 3 | — | 0 | — |
| | 0.28 | — | — | 3 | — | 2 | — | — | — | — | 2 | — | — | — | 3 |
| | 0.07 | — | — | 3 | — | 1 | — | — | — | — | 1 | — | — | — | 2 |
| | 0.07 | 0 | 0 | — | 0 | — | 3 | — | — | 1 | — | 3 | — | 0 | — |
| | 0.02 | — | — | 1 | — | 0 | — | — | — | — | 1 | — | — | — | 0 |
| | 0.02 | 0 | 0 | — | 1 | — | 2 | — | — | 1 | — | 1 | — | 0 | — |
| 100 | 5.61 | — | — | 3 | — | 3 | — | — | — | — | 3 | — | — | — | 2 |
| | 5.61 | 3 | 1 | — | 0 | — | 3 | — | — | 3 | — | 1 | — | 0 | — |
| | 1.12 | 0 | 0 | — | 0 | — | 2 | — | — | 2 | — | 0 | — | 0 | — |
| | 1.12 | — | — | 3 | — | 3 | — | — | — | — | 2 | — | — | — | 2 |

TABLE B-continued

Herbicide Secondary Preemergence
(C = 100% control)

| Cmpd | Rate | | | | | | | | | | | | | | |
|---|---|---|---|---|---|---|---|---|---|---|---|---|---|---|---|
|  | 0.28 | — | — | 3 | — | 2 | — | — | — | — | 0 | — | — | — | 0 |
|  | 0.28 | 0 | 0 | — | 0 | — | 0 | — | — | 0 | — | 0 | — | 0 | — |
|  | 0.07 | 0 | 0 | — | 0 | — | 0 | — | — | 0 | — | 0 | — | 0 | — |
|  | 0.07 | — | — | 2 | — | 0 | — | — | — | — | 0 | — | — | — | 0 |
| 101 | 1.12 | — | — | 3 | — | 3 | — | — | — | — | 3 | — | — | — | 3 |
|  | 1.12 | 3 | 3 | — | 2 | — | 3 | — | — | 3 | — | 3 | — | 3 | — |
|  | 0.28 | 3 | 3 | — | 1 | — | 3 | — | — | 3 | — | 3 | — | 3 | — |
|  | 0.28 | — | — | 3 | — | 3 | — | — | — | — | 3 | — | — | — | 3 |
|  | 0.07 | — | — | 3 | — | 3 | — | — | — | — | 3 | — | — | — | 3 |
|  | 0.07 | 3 | 2 | — | 1 | — | 3 | — | — | 3 | — | 2 | — | 2 | — |
|  | 0.02 | 1 | 1 | — | 0 | — | 1 | — | — | 3 | — | 1 | — | 0 | — |
|  | 0.02 | — | — | 3 | — | 3 | — | — | — | — | 3 | — | — | — | 2 |
|  | 0.00 | — | — | 3 | — | 2 | — | — | — | — | 0 | — | — | — | 1 |
|  | 0.00 | 0 | 0 | — | 0 | — | 0 | — | — | 2 | — | 0 | — | 0 | — |
| 102 | 1.12 | 3 | 3 | — | 2 | — | 3 | — | — | 3 | — | 3 | — | 3 | — |
|  | 1.12 | — | — | 3 | — | 3 | — | — | — | — | 3 | — | — | — | 3 |
|  | 0.28 | — | — | 3 | — | 3 | — | — | — | — | 3 | — | — | — | 3 |
|  | 0.28 | 3 | 3 | — | 1 | — | 3 | — | — | 3 | — | 3 | — | 3 | — |
|  | 0.07 | 2 | 1 | — | 0 | — | 3 | — | — | 3 | — | 3 | — | 2 | — |
|  | 0.07 | — | — | 3 | — | 3 | — | — | — | — | 3 | — | — | — | 3 |
|  | 0.02 | — | — | 2 | — | 3 | — | — | — | — | 0 | — | — | — | 1 |
|  | 0.02 | 0 | N | 0 | 0 | 0 | 1 | 1 | — | 0 | 1 | 0 | 0 | 0 | 0 |
|  | 0.02 | 0 | 0 | — | 0 | — | 1 | — | — | 2 | — | 1 | — | 0 | — |
|  | 0.00 | 0 | 0 | — | 0 | — | 0 | — | — | 1 | — | 0 | — | 0 | — |
|  | 0.00 | — | — | 2 | — | 2 | — | — | — | — | 0 | — | — | — | 1 |
| 103 | 1.12 | — | — | 3 | — | 3 | — | — | — | — | 3 | — | — | — | 3 |
|  | 1.12 | 3 | 3 | — | 3 | — | 3 | — | — | 3 | — | 3 | — | 3 | — |
|  | 0.28 | 1 | 1 | — | 1 | — | 3 | — | — | 3 | — | 1 | — | 1 | — |
|  | 0.28 | — | — | 3 | — | 3 | — | — | — | — | 3 | — | — | — | 3 |
|  | 0.07 | — | — | 3 | — | 3 | — | — | — | — | 3 | — | — | — | 3 |
|  | 0.07 | 0 | 0 | — | 0 | — | 0 | — | — | 2 | — | 0 | — | 0 | — |
|  | 0.02 | 0 | 0 | — | 0 | — | 0 | — | — | 1 | — | 0 | — | 0 | — |
|  | 0.02 | — | — | 1 | — | 3 | — | — | — | — | 1 | — | — | — | 1 |
|  | 0.00 | — | — | 0 | — | 0 | — | — | — | — | 0 | — | — | — | 1 |
|  | 0.00 | 0 | 0 | — | 0 | — | 0 | — | — | 0 | — | 0 | — | 0 | — |
|  | 0.00 | 0 | 0 | — | 0 | — | 0 | — | — | 0 | — | 0 | — | 0 | — |
|  | 0.00 | — | — | 0 | — | 0 | — | — | — | — | 0 | — | — | — | 0 |
| 104 | 5.61 | — | — | 3 | — | 3 | — | — | — | — | 3 | — | — | — | 1 |
|  | 5.61 | 0 | 0 | — | 0 | — | 1 | — | — | 1 | — | 0 | — | 1 | — |
|  | 1.12 | 0 | 0 | — | 0 | — | 0 | — | — | 0 | — | 0 | — | 0 | — |
|  | 1.12 | — | — | 2 | — | 1 | — | — | — | — | 2 | — | — | — | 1 |
|  | 0.28 | — | — | 1 | — | 1 | — | — | — | — | 0 | — | — | — | 0 |
|  | 0.28 | 0 | 0 | — | 0 | — | 0 | — | — | 0 | — | 0 | — | 0 | — |
|  | 0.07 | 0 | 0 | — | 0 | — | 0 | — | — | 0 | — | 0 | — | 0 | — |
|  | 0.07 | — | — | 0 | — | 1 | — | — | — | — | 0 | — | — | — | 0 |
|  | 0.02 | — | — | 0 | — | 0 | — | — | — | — | 0 | — | — | — | 0 |
|  | 0.02 | 0 | 0 | — | 0 | — | 0 | — | — | 0 | — | 0 | — | 0 | — |
| 105 | 11.21 | 0 | 0 | — | 0 | — | 1 | — | — | 1 | — | 0 | — | 0 | — |
|  | 11.21 | — | — | 0 | — | 0 | — | — | — | — | 1 | — | — | — | 1 |
|  | 5.61 | — | — | 2 | — | 3 | — | — | — | — | 2 | — | — | — | 2 |
|  | 5.61 | 0 | 0 | — | 0 | — | 1 | — | — | 0 | — | 0 | — | 0 | — |
|  | 1.12 | 0 | 0 | — | 0 | — | 0 | — | — | 0 | — | 0 | — | 0 | — |
|  | 1.12 | — | — | 0 | — | 0 | — | — | — | — | 0 | — | — | — | 0 |
|  | 0.28 | — | — | 0 | — | 0 | — | — | — | — | 0 | — | — | — | 1 |
|  | 0.28 | 0 | 0 | — | 0 | — | 0 | — | — | 0 | — | N | — | 0 | — |
| 106 | 1.12 | 3 | 3 | — | 2 | — | 3 | — | — | 3 | — | 3 | — | 3 | — |
|  | 1.12 | — | — | 3 | — | 3 | — | — | — | — | 3 | — | — | — | 3 |
|  | 0.28 | — | — | 3 | — | 3 | — | — | — | — | 3 | — | — | — | 3 |
|  | 0.28 | 3 | 3 | — | 0 | — | 3 | — | — | 2 | — | 3 | — | 3 | — |
|  | 0.07 | 1 | 1 | — | 0 | — | 3 | — | — | 1 | — | 3 | — | 1 | — |
|  | 0.07 | — | — | 3 | — | 3 | — | — | — | — | 3 | — | — | — | 2 |
|  | 0.02 | — | — | 3 | — | 2 | — | — | — | — | 1 | — | — | — | 1 |
|  | 0.02 | 0 | 0 | — | 0 | — | 1 | — | — | 0 | — | 2 | — | 0 | — |
|  | 0.00 | 0 | 0 | — | 0 | — | 0 | — | — | 0 | — | 0 | — | 0 | — |
|  | 0.00 | — | — | 2 | — | 0 | — | — | — | — | 0 | — | — | — | 2 |
| 107 | 1.12 | — | — | 3 | — | 3 | — | — | — | — | 3 | — | — | — | 3 |
|  | 1.12 | 3 | 3 | — | 3 | — | 3 | — | — | 3 | — | 3 | — | 3 | — |
|  | 0.28 | 3 | 3 | — | 1 | — | 3 | — | — | 3 | — | 3 | — | 3 | — |
|  | 0.28 | — | — | 3 | — | 3 | — | — | — | — | 3 | — | — | — | 3 |
|  | 0.07 | — | — | 3 | — | 3 | — | — | — | — | 3 | — | — | — | 2 |
|  | 0.07 | 2 | 1 | — | 0 | — | 3 | — | — | 3 | — | 2 | — | 2 | — |
|  | 0.02 | 1 | 1 | — | 0 | — | 2 | — | — | 3 | — | 1 | — | 1 | — |
|  | 0.02 | — | — | 3 | — | 3 | — | — | — | — | 0 | — | — | — | 0 |
|  | 0.00 | — | — | 2 | — | 0 | — | — | — | — | 0 | — | — | — | 0 |
|  | 0.00 | 0 | 1 | — | 0 | — | 2 | — | — | 0 | — | 2 | — | 0 | — |
| 108 | 11.21 | 0 | 0 | — | 0 | — | 0 | — | — | 0 | — | 0 | — | 0 | — |
|  | 11.21 | — | — | 1 | — | 0 | — | — | — | — | 0 | — | — | — | 0 |
|  | 5.61 | — | — | 0 | — | 0 | — | — | — | — | 0 | — | — | — | 0 |
|  | 5.61 | 0 | N | — | 0 | — | 0 | — | — | 0 | — | 0 | — | 0 | — |
|  | 1.12 | 0 | 0 | — | 0 | — | 0 | — | — | 0 | — | 0 | — | 0 | — |

TABLE B-continued

Herbicide Secondary Preemergence
(C = 100% control)

|     | 1.12 | — | — | 1 | — | 0 | — | — | — | — | 0 | — | — | — | 0 |
|-----|------|---|---|---|---|---|---|---|---|---|---|---|---|---|---|
| 109 | 5.61 | — | — | 3 | — | 3 | — | — | — | — | 3 | — | — | — | 3 |
|     | 5.61 | 3 | 3 | — | 2 | — | 3 | — | — | 3 | — | 3 | — | 3 | — |
|     | 1.12 | 3 | 3 | — | 0 | — | 3 | — | — | 3 | — | 3 | — | 3 | — |
|     | 1.12 | — | — | 3 | — | 3 | — | — | — | — | 2 | — | — | — | 3 |
|     | 0.28 | — | — | 3 | — | 3 | — | — | — | — | 1 | — | — | — | 2 |
|     | 0.28 | 2 | 0 | — | 0 | — | 3 | — | — | 3 | — | 3 | — | 3 | — |
|     | 0.07 | 0 | 0 | — | 0 | — | 0 | — | — | 1 | — | 0 | — | 0 | — |
|     | 0.07 | — | — | 2 | — | 2 | — | — | — | — | 0 | — | — | — | 2 |
|     | 0.02 | — | — | 0 | — | 1 | — | — | — | — | 0 | — | — | — | 0 |
|     | 0.02 | 0 | 0 | — | 0 | — | 0 | — | — | 0 | — | 0 | — | 0 | — |
|     | 0.00 | 0 | 0 | — | 0 | — | 0 | — | — | 0 | — | 0 | — | 0 | — |
|     | 0.00 | — | — | 0 | — | 0 | — | — | — | — | 0 | — | — | — | 0 |

| Ex. No. | Rate kg/ha | Prmi | Bygr | Lacg | Grft | Sube | Colq | Pesw | Cocw | Anbg | Barz | Ruth | Sejg | Wioa | Cwbs | Blgr |
|---|---|---|---|---|---|---|---|---|---|---|---|---|---|---|---|---|
| 1 | 5.61 | 3 | 3 | 3 | — | 3 | 3 | 3 | — | — | — | — | — | — | — | — |
|   | 1.12 | 3 | 3 | 3 | — | 3 | 3 | 2 | — | — | — | — | — | — | — | — |
|   | 0.28 | 2 | 1 | 3 | — | 0 | 0 | 0 | — | — | — | — | — | — | — | — |
|   | 0.06 | 0 | 1 | 0 | — | 0 | 1 | 0 | — | — | — | — | — | — | — | — |
|   | 0.01 | 0 | 0 | 0 | — | 0 | 0 | 0 | — | — | — | — | — | — | — | — |
| 2 | 5.61 | 3 | 3 | 3 | — | 3 | 3 | 3 | — | — | — | — | — | — | — | — |
|   | 1.12 | 3 | 3 | 3 | — | 2 | 3 | 3 | — | — | — | — | — | — | — | — |
|   | 0.28 | 3 | 3 | 3 | — | 1 | 0 | 1 | — | — | — | — | — | — | — | — |
|   | 0.06 | 1 | 2 | 1 | — | 0 | 0 | 0 | — | — | — | — | — | — | — | — |
|   | 0.01 | 0 | 0 | 0 | — | 0 | 0 | 0 | — | — | — | — | — | — | — | — |
| 3 | 5.61 | 3 | 3 | 3 | — | 0 | 0 | 0 | — | — | — | — | — | — | — | — |
|   | 1.12 | 0 | 0 | 0 | — | 0 | 0 | 0 | — | — | — | — | — | — | — | — |
| 4 | 5.61 | 3 | 3 | 3 | — | 3 | 3 | 3 | — | — | — | — | — | — | — | — |
|   | 1.12 | 3 | 3 | 3 | — | 3 | 3 | 2 | — | — | — | — | — | — | — | — |
|   | 0.28 | 3 | 3 | 3 | — | 1 | 0 | 2 | — | — | — | — | — | — | — | — |
|   | 0.06 | 2 | 3 | 3 | — | 0 | 0 | 0 | — | — | — | — | — | — | — | — |
|   | 0.01 | 0 | 0 | 0 | — | 0 | 0 | 0 | — | — | — | — | — | — | — | — |
| 5 | 5.61 | 3 | 3 | 3 | — | 2 | 3 | 2 | — | — | — | — | — | — | — | — |
|   | 1.12 | 3 | 3 | 3 | — | 0 | 0 | 2 | — | — | — | — | — | — | — | — |
|   | 0.28 | 1 | 1 | 2 | — | 0 | 0 | 2 | — | — | — | — | — | — | — | — |
|   | 0.06 | 0 | 0 | 0 | — | 1 | 0 | 0 | — | — | — | — | — | — | — | — |
| 6 | 5.61 | N | N | N | — | N | N | N | — | — | — | — | — | — | — | — |
|   | 5.61 | 0 | 1 | 0 | — | 0 | 0 | 0 | — | — | — | — | — | — | — | — |
|   | 1.12 | 0 | 0 | 0 | — | 0 | 0 | 0 | — | — | — | — | — | — | — | — |
|   | 1.12 | N | N | N | — | N | N | N | — | — | — | — | — | — | — | — |
|   | 0.28 | 0 | 0 | 1 | — | 0 | 0 | 0 | — | — | — | — | — | — | — | — |
|   | 0.28 | N | N | N | — | N | N | N | — | — | — | — | — | — | — | — |
| 7 | 1.12 | 2 | 3 | 3 | — | 2 | 0 | 0 | — | — | — | — | — | — | — | — |
|   | 0.28 | 0 | 0 | 1 | — | 0 | 0 | 0 | — | — | — | — | — | — | — | — |
| 8 | 5.61 | 3 | 3 | 3 | 3 | 3 | 3 | 3 | — | — | — | — | — | — | — | — |
|   | 1.12 | 3 | 3 | 3 | 3 | 3 | 3 | 3 | — | — | — | — | — | — | — | — |
|   | 0.56 | 3 | 3 | 3 | 3 | 3 | 3 | 3 | — | — | — | — | — | — | — | — |
|   | 0.28 | 3 | 3 | 3 | 3 | 3 | 3 | 3 | — | — | — | — | — | — | — | — |
|   | 0.14 | 3 | 3 | 3 | 3 | 3 | 3 | 3 | — | — | — | — | — | — | — | — |
|   | 0.07 | 3 | 3 | 3 | 3 | 1 | 0 | 3 | — | — | — | — | — | — | — | — |
|   | 0.03 | 3 | 3 | 1 | 3 | 0 | 0 | 1 | — | — | — | — | — | — | — | — |
|   | 0.02 | 2 | 2 | 0 | 3 | N | N | 1 | — | — | — | — | — | — | — | — |
|   | 0.01 | 1 | 0 | 0 | 0 | 0 | 0 | 0 | — | — | — | — | — | — | — | — |
| 10 | 5.61 | 3 | 3 | 3 | 3 | 3 | 3 | 3 | — | — | — | — | — | — | — | — |
|    | 1.12 | 3 | 3 | 3 | 3 | 1 | 3 | 3 | — | — | — | — | — | — | — | — |
|    | 0.56 | 3 | 3 | 3 | 3 | 2 | 0 | 3 | — | — | — | — | — | — | — | — |
|    | 0.28 | 3 | 3 | 3 | 3 | 0 | 0 | 2 | — | — | — | — | — | — | — | — |
|    | 0.14 | 3 | 3 | 3 | 3 | 2 | N | 3 | — | — | — | — | — | — | — | — |
|    | 0.07 | 3 | 3 | 3 | 3 | 0 | 0 | 2 | — | — | — | — | — | — | — | — |
|    | 0.03 | 1 | 0 | 2 | 1 | 0 | 0 | 0 | — | — | — | — | — | — | — | — |
|    | 0.02 | 2 | 0 | 0 | 0 | 0 | 0 | 0 | — | — | — | — | — | — | — | — |
|    | 0.01 | 0 | 0 | N | 0 | 0 | 0 | 0 | — | — | — | — | — | — | — | — |
| 11 | 5.61 | 3 | 3 | 3 | 3 | 3 | 2 | 3 | — | — | — | — | — | — | — | — |
|    | 1.12 | 3 | 3 | 3 | 3 | 3 | 1 | 1 | — | — | — | — | — | — | — | — |
|    | 0.56 | 2 | 3 | 2 | 3 | 0 | 0 | 0 | — | — | — | — | — | — | — | — |
| 12 | 5.61 | 3 | 3 | 3 | 3 | — | — | — | — | — | — | — | — | — | — | — |
|    | 1.12 | 2 | 0 | 0 | 1 | — | — | — | — | — | — | — | — | — | — | — |
|    | 0.28 | 2 | 0 | 1 | 0 | — | — | — | — | — | — | — | — | — | — | — |
|    | 0.07 | 2 | N | 1 | N | — | — | — | — | — | — | — | — | — | — | — |
|    | 0.02 | N | N | 0 | N | — | — | — | — | — | — | — | — | — | — | — |
| 13 | 5.61 | 3 | 3 | 3 | 3 | — | — | — | — | — | — | — | — | — | — | — |
|    | 1.12 | 3 | 3 | 3 | 3 | — | — | — | — | — | — | — | — | — | — | — |
|    | 0.28 | 3 | 3 | 3 | 3 | — | — | — | — | — | — | — | — | — | — | — |
|    | 0.07 | 0 | 0 | 3 | 0 | — | — | — | — | — | — | — | — | — | — | — |
|    | 0.02 | 0 | 0 | 2 | 0 | — | — | — | — | — | — | — | — | — | — | — |
|    | 0.01 | 0 | 0 | 0 | 0 | — | — | — | — | — | — | — | — | — | — | — |
| 14 | 5.61 | 3 | 3 | 3 | 3 | — | — | — | — | — | — | — | — | — | — | — |
|    | 1.12 | 3 | 3 | 3 | 3 | — | — | — | — | — | — | — | — | — | — | — |
|    | 0.28 | 3 | 3 | 3 | 3 | — | — | — | — | — | — | — | — | — | — | — |

TABLE B-continued

Herbicide Secondary Preemergence
(C = 100% control)

|    | rate | | | | | | | | | | | | | | | |
|----|------|---|---|---|---|---|---|---|---|---|---|---|---|---|---|---|
|    | 0.07 | 3 | 3 | 3 | 3 | — | — | — | — | — | — | — | — | — | — | — |
|    | 0.02 | 3 | 3 | 3 | 3 | — | — | — | — | — | — | — | — | — | — | — |
|    | 0.01 | 2 | 0 | 2 | 3 | — | — | — | — | — | — | — | — | — | — | — |
| 15 | 5.61 | 3 | 3 | 3 | 3 | — | — | — | — | — | — | — | — | — | — | — |
|    | 1.12 | 3 | 3 | 3 | 3 | — | — | — | — | — | — | — | — | — | — | — |
|    | 0.28 | 3 | 3 | 3 | 3 | — | — | — | — | — | — | — | — | — | — | — |
|    | 0.07 | 1 | 2 | 3 | 2 | — | — | — | — | — | — | — | — | — | — | — |
|    | 0.02 | 0 | 0 | 2 | 0 | — | — | — | — | — | — | — | — | — | — | — |
|    | 0.01 | 0 | 0 | 2 | 0 | — | — | — | — | — | — | — | — | — | — | — |
| 16 | 5.61 | 3 | 3 | 3 | 3 | — | — | — | — | — | — | — | — | — | — | — |
|    | 1.12 | 3 | 3 | 3 | 2 | — | — | — | — | — | — | — | — | — | — | — |
|    | 0.28 | 3 | 1 | 3 | 0 | — | — | — | — | — | — | — | — | — | — | — |
|    | 0.07 | 0 | 0 | 0 | 0 | — | — | — | — | — | — | — | — | — | — | — |
| 17 | 5.61 | 3 | 3 | 3 | 3 | — | — | — | — | — | — | — | — | — | — | — |
|    | 1.12 | 3 | 3 | 3 | 3 | — | — | — | — | — | — | — | — | — | — | — |
|    | 0.28 | 3 | 3 | 3 | 3 | — | — | — | — | — | — | — | — | — | — | — |
|    | 0.07 | 3 | 3 | 3 | 3 | — | — | — | — | — | — | — | — | — | — | — |
|    | 0.02 | 1 | 3 | 3 | 3 | — | — | — | — | — | — | — | — | — | — | — |
|    | 0.01 | 0 | 1 | 0 | 0 | — | — | — | — | — | — | — | — | — | — | — |
| 18 | 5.61 | 3 | 3 | 3 | 3 | — | — | — | — | — | — | — | — | — | — | — |
|    | 5.61 | 3 | 3 | 3 | 3 | — | — | — | — | — | — | — | — | — | — | — |
|    | 1.12 | 3 | 3 | 3 | 3 | — | — | — | — | — | — | — | — | — | — | — |
|    | 1.12 | 3 | 3 | 3 | 3 | — | — | — | — | — | — | — | — | — | — | — |
|    | 0.28 | 3 | 3 | 3 | 3 | — | — | — | — | — | — | — | — | — | — | — |
|    | 0.28 | 0 | 3 | 2 | 2 | — | — | — | — | — | — | — | — | — | — | — |
|    | 0.07 | 0 | 0 | 0 | 0 | — | — | — | — | — | — | — | — | — | — | — |
|    | 0.07 | 0 | 0 | 1 | 0 | — | — | — | — | — | — | — | — | — | — | — |
|    | 0.02 | 0 | 0 | 0 | 0 | — | — | — | — | — | — | — | — | — | — | — |
|    | 0.02 | N | N | N | N | — | — | — | — | — | — | — | — | — | — | — |
|    | 0.01 | N | N | N | N | — | — | — | — | — | — | — | — | — | — | — |
|    | 0.01 | 0 | 0 | N | 1 | — | — | — | — | — | — | — | — | — | — | — |
| 19 | 5.61 | 0 | 3 | 3 | 1 | — | — | — | — | — | — | — | — | — | — | — |
|    | 1.12 | 0 | 0 | 1 | 0 | — | — | — | — | — | — | — | — | — | — | — |
|    | 0.28 | 0 | 0 | 0 | 0 | — | — | — | — | — | — | — | — | — | — | — |
|    | 0.07 | 0 | 0 | 0 | 0 | — | — | — | — | — | — | — | — | — | — | — |
| 20 | 5.61 | 3 | 3 | 3 | 3 | — | — | — | — | — | — | — | — | — | — | — |
|    | 1.12 | 3 | 3 | 3 | 3 | — | — | — | — | — | — | — | — | — | — | — |
|    | 0.28 | 0 | 1 | 3 | 2 | — | — | — | — | — | — | — | — | — | — | — |
|    | 0.07 | 0 | 0 | 0 | 0 | — | — | — | — | — | — | — | — | — | — | — |
| 21 | 5.61 | 0 | 0 | 1 | 0 | — | — | — | — | — | — | — | — | — | — | — |
|    | 1.12 | 0 | 0 | 0 | 0 | — | — | — | — | — | — | — | — | — | — | — |
|    | 0.28 | 0 | 0 | 0 | 0 | — | — | — | — | — | — | — | — | — | — | — |
| 23 | 5.61 | 1 | 1 | 3 | 1 | — | — | — | — | — | — | — | — | — | — | — |
|    | 1.12 | 0 | 0 | 2 | 0 | — | — | — | — | — | — | — | — | — | — | — |
|    | 0.28 | 1 | 0 | 0 | 0 | — | — | — | — | — | — | — | — | — | — | — |
| 24 | 5.61 | 3 | 3 | 3 | 3 | — | — | — | — | — | — | — | — | — | — | — |
|    | 1.12 | 1 | 1 | 3 | 3 | — | — | — | — | — | — | — | — | — | — | — |
|    | 0.28 | 0 | 0 | 1 | 1 | — | — | — | — | — | — | — | — | — | — | — |
|    | 0.07 | 0 | 0 | 1 | 0 | — | — | — | — | — | — | — | — | — | — | — |
| 25 | 5.61 | 3 | 3 | 3 | 3 | — | — | — | — | — | — | — | — | — | — | — |
|    | 1.12 | 3 | 3 | 3 | 3 | — | — | — | — | — | — | — | — | — | — | — |
|    | 0.28 | 3 | 3 | 3 | 3 | — | — | — | — | — | — | — | — | — | — | — |
|    | 0.07 | 0 | 0 | 3 | 0 | — | — | — | — | — | — | — | — | — | — | — |
|    | 0.02 | 0 | 0 | 0 | 0 | — | — | — | — | — | — | — | — | — | — | — |
|    | 0.01 | 0 | 0 | 0 | 0 | — | — | — | — | — | — | — | — | — | — | — |
| 26 | 5.61 | 3 | 3 | 3 | 3 | — | — | — | — | — | — | — | — | — | — | — |
|    | 1.12 | 3 | 3 | 3 | 3 | — | — | — | — | — | — | — | — | — | — | — |
|    | 0.28 | 3 | 3 | 3 | 3 | — | — | — | — | — | — | — | — | — | — | — |
|    | 0.07 | 3 | 3 | 3 | 3 | — | — | — | — | — | — | — | — | — | — | — |
|    | 0.02 | 0 | 3 | 3 | 3 | — | — | — | — | — | — | — | — | — | — | — |
| 27 | 5.61 | 3 | 3 | 3 | 3 | — | — | — | — | — | — | — | — | — | — | — |
|    | 1.12 | 3 | 3 | 3 | 3 | — | — | — | — | — | — | — | — | — | — | — |
|    | 0.28 | 3 | 3 | 3 | 3 | — | — | — | — | — | — | — | — | — | — | — |
|    | 0.07 | 0 | 0 | 2 | 1 | — | — | — | — | — | — | — | — | — | — | — |
|    | 0.02 | 0 | 0 | 0 | 0 | — | — | — | — | — | — | — | — | — | — | — |
|    | 0.01 | 0 | 0 | 0 | 0 | — | — | — | — | — | — | — | — | — | — | — |
| 28 | 5.61 | 3 | 3 | 3 | 3 | — | — | — | — | — | — | — | — | — | — | — |
|    | 1.12 | 0 | 1 | 0 | 1 | — | — | — | — | — | — | — | — | — | — | — |
|    | 0.28 | 0 | 0 | 1 | 0 | — | — | — | — | — | — | — | — | — | — | — |
|    | 0.07 | 0 | 0 | 0 | 0 | — | — | — | — | — | — | — | — | — | — | — |
|    | 0.02 | 0 | 0 | 0 | 0 | — | — | — | — | — | — | — | — | — | — | — |
| 29 | 5.61 | 3 | 3 | 3 | 3 | — | — | — | 2 | — | — | — | — | — | — | — |
|    | 1.12 | 0 | 2 | 2 | 2 | — | — | — | 0 | — | — | — | — | — | — | — |
|    | 0.28 | 0 | 0 | 2 | 0 | — | — | — | 0 | — | — | — | — | — | — | — |
|    | 0.07 | 0 | 0 | 0 | 0 | — | — | — | 0 | — | — | — | — | — | — | — |
| 31 | 5.61 | 2 | 0 | 3 | 3 | — | — | — | 2 | — | — | — | — | — | — | — |
|    | 1.12 | 0 | 1 | 2 | 1 | — | — | — | 0 | — | — | — | — | — | — | — |
|    | 0.28 | 0 | 0 | 0 | 0 | — | — | — | 0 | — | — | — | — | — | — | — |
|    | 0.07 | 0 | 0 | 0 | 0 | — | — | — | 0 | — | — | — | — | — | — | — |
| 32 | 5.61 | 3 | 3 | 3 | 3 | — | — | — | 3 | — | — | — | — | — | — | — |

TABLE B-continued

Herbicide Secondary Preemergence
(C = 100% control)

|  | rate | | | | | | | | | | | | | | |
|---|---|---|---|---|---|---|---|---|---|---|---|---|---|---|---|
| | 1.12 | 3 | 3 | 3 | 3 | — | — | — | 3 | — | — | — | — | — | — |
| | 0.28 | 3 | 3 | 3 | 3 | — | — | — | 2 | — | — | — | — | — | — |
| | 0.07 | 2 | 3 | 3 | 3 | — | — | — | 0 | — | — | — | — | — | — |
| | 0.02 | 1 | 0 | 0 | 0 | — | — | — | 0 | — | — | — | — | — | — |
| | 0.01 | 0 | 0 | 0 | 0 | — | — | — | 0 | — | — | — | — | — | — |
| 33 | 5.61 | 3 | 3 | 3 | 3 | — | — | — | 3 | — | — | — | — | — | — |
| | 1.12 | 3 | 3 | 3 | 3 | — | — | — | 3 | — | — | — | — | — | — |
| | 0.28 | 2 | 3 | 3 | 3 | — | — | — | 3 | — | — | — | — | — | — |
| | 0.07 | 1 | 2 | 1 | 1 | — | — | — | 1 | — | — | — | — | — | — |
| 34 | 5.61 | 3 | 3 | 3 | 3 | — | — | — | 3 | — | — | — | — | — | — |
| | 1.12 | 3 | 3 | 3 | 3 | — | — | — | 3 | — | — | — | — | — | — |
| | 0.28 | 0 | 1 | 0 | 1 | — | — | — | 0 | — | — | — | — | — | — |
| | 0.07 | 0 | 0 | 1 | 0 | — | — | — | 0 | — | — | — | — | — | — |
| | 0.02 | 0 | 0 | 0 | 0 | — | — | — | 0 | — | — | — | — | — | — |
| | 0.01 | 0 | 0 | 1 | 0 | — | — | — | 0 | — | — | — | — | — | — |
| 35 | 5.61 | 3 | 3 | 3 | 3 | — | — | — | 3 | — | — | — | — | — | — |
| | 1.12 | 3 | 3 | 3 | 3 | — | — | — | 3 | — | — | — | — | — | — |
| | 0.28 | 3 | 3 | 3 | 3 | — | — | — | 3 | — | — | — | — | — | — |
| | 0.07 | 1 | 3 | 3 | 3 | — | — | — | 0 | — | — | — | — | — | — |
| | 0.02 | 1 | 1 | 3 | 1 | — | — | — | 0 | — | — | — | — | — | — |
| | 0.01 | 0 | 0 | 1 | 0 | — | — | — | 0 | — | — | — | — | — | — |
| 36 | 5.61 | 3 | 3 | 3 | 3 | — | — | — | 3 | — | — | — | — | — | — |
| | 1.12 | 3 | 3 | 3 | 3 | — | — | — | 3 | — | — | — | — | — | — |
| | 0.28 | 3 | 3 | 3 | 3 | — | — | — | 3 | — | — | — | — | — | — |
| | 0.07 | 3 | 3 | 3 | 3 | — | — | — | 1 | — | — | — | — | — | — |
| | 0.02 | 2 | 3 | 3 | 3 | — | — | — | 0 | — | — | — | — | — | — |
| | 0.01 | 1 | 2 | 1 | 2 | — | — | — | 1 | — | — | — | — | — | — |
| 37 | 1.12 | — | 3 | 3 | — | — | — | — | — | — | — | — | 3 | — | — |
| | 1.21 | — | 3 | 3 | — | — | — | — | — | — | — | — | 3 | — | — |
| | 1.21 | — | — | — | 3 | — | — | — | 3 | 3 | 0 | 0 | — | 3 | — |
| | 11.21 | — | — | — | 3 | — | — | — | 2 | 3 | 0 | 0 | — | 3 | — |
| | 10.20 | — | 3 | 3 | — | — | — | — | — | — | — | — | 3 | — | — |
| | 10.20 | — | — | — | 3 | — | — | — | 0 | 3 | 0 | 0 | — | 3 | — |
| | 5.61 | — | — | — | 3 | — | — | — | 2 | 3 | 0 | 0 | — | 3 | — |
| | 5.61 | — | — | — | 3 | — | — | — | 3 | 3 | 1 | 0 | — | 3 | — |
| | 5.61 | — | 3 | 3 | — | — | — | — | — | — | — | — | 3 | — | — |
| | 5.61 | — | 3 | 3 | — | — | — | — | — | — | — | — | 3 | — | — |
| | 5.61 | — | — | — | 3 | — | — | — | 0 | 3 | 0 | 0 | — | 3 | — |
| | 5.61 | — | — | — | 3 | — | — | — | 0 | 3 | 0 | 0 | — | 3 | — |
| | 5.61 | — | 3 | 3 | — | — | — | — | — | — | — | — | 3 | — | — |
| | 5.61 | — | 3 | 3 | — | — | — | — | — | — | — | — | 3 | — | — |
| | 1.12 | — | 3 | 3 | — | — | — | — | — | — | — | — | 3 | — | — |
| | 1.12 | — | 3 | 3 | — | — | — | — | — | — | — | — | 3 | — | — |
| | 1.12 | — | — | — | 3 | — | — | — | 0 | 3 | 0 | 0 | — | 3 | — |
| | 1.12 | — | 3 | 3 | — | — | — | — | — | — | — | — | 3 | — | — |
| | 1.12 | — | — | — | 3 | — | — | — | 3 | 3 | 0 | 0 | — | 3 | — |
| | 1.12 | — | 3 | 3 | — | — | — | — | — | — | — | — | 3 | — | — |
| | 1.12 | — | — | — | 3 | — | — | — | N | 3 | 0 | 0 | — | 3 | — |
| | 1.12 | — | — | — | 3 | — | — | — | N | 3 | 0 | 0 | — | 3 | — |
| | 0.28 | — | — | — | 3 | — | — | — | 0 | 3 | 0 | 0 | — | 3 | — |
| | 0.28 | — | — | — | 3 | — | — | — | 0 | 3 | 0 | 0 | — | 3 | — |
| | 0.28 | — | — | — | 3 | — | — | — | 0 | 3 | 0 | 0 | — | 3 | — |
| | 0.28 | — | 3 | 3 | — | — | — | — | — | — | — | — | 3 | — | — |
| | 0.28 | — | 3 | 3 | — | — | — | — | — | — | — | — | 3 | — | — |
| | 0.28 | — | — | — | 3 | — | — | — | 3 | 3 | 0 | 0 | — | 3 | — |
| | 0.28 | — | 3 | 3 | — | — | — | — | — | — | — | — | 3 | — | — |
| | 0.28 | — | 3 | 3 | — | — | — | — | — | — | — | — | 3 | — | — |
| | 0.07 | — | 3 | 3 | — | — | — | — | — | — | — | — | 3 | — | — |
| | 0.07 | — | 2 | 3 | — | — | — | — | — | — | — | — | 2 | — | — |
| | 0.07 | — | — | — | 3 | — | — | — | 0 | 3 | 0 | 0 | — | 2 | — |
| | 0.07 | — | 3 | 3 | — | — | — | — | — | — | — | — | 3 | — | — |
| | 0.07 | — | — | — | 3 | — | — | — | 1 | 3 | 0 | 0 | — | 3 | — |
| | 0.07 | — | 1 | 3 | — | — | — | — | — | — | — | — | 2 | — | — |
| | 0.07 | — | — | — | 3 | — | — | — | 0 | 3 | 0 | 0 | — | 0 | — |
| | 0.07 | — | — | — | 3 | — | — | — | 0 | 3 | 0 | 0 | — | 2 | — |
| | 0.02 | — | 0 | 1 | — | — | — | — | — | — | — | — | 0 | — | — |
| | 0.02 | — | — | — | 0 | — | — | — | 0 | 2 | 0 | 0 | — | 0 | — |
| | 0.02 | — | — | — | 0 | — | — | — | 0 | 0 | 0 | 0 | — | 0 | — |
| | 0.02 | — | 0 | 3 | — | — | — | — | — | — | — | — | 0 | — | — |
| 38 | 11.21 | — | 3 | 3 | — | — | — | — | — | — | — | — | 3 | — | — |
| | 11.21 | — | — | — | 3 | — | — | — | 2 | 3 | 0 | 1 | — | 3 | — |
| | 5.61 | — | — | — | 3 | — | — | — | 0 | 3 | 0 | 0 | — | 3 | — |
| | 5.61 | — | 3 | 3 | — | — | — | — | — | — | — | — | 3 | — | — |
| | 1.12 | — | 3 | 3 | — | — | — | — | — | — | — | — | 0 | — | — |
| | 1.12 | — | — | — | 2 | — | — | — | 0 | 3 | 0 | 0 | — | 2 | — |
| 39 | 5.61 | — | — | — | 3 | — | — | — | 3 | 3 | 1 | 0 | — | 3 | — |
| | 5.61 | — | 3 | 3 | — | — | — | — | — | — | — | — | 3 | — | — |
| | 1.12 | — | 3 | 3 | — | — | — | — | — | — | — | — | 3 | — | — |
| | 1.12 | — | — | — | 3 | — | — | — | 3 | 3 | 1 | 0 | — | 3 | — |
| | 0.28 | — | — | — | 3 | — | — | — | 3 | 3 | 1 | 0 | — | 3 | — |

TABLE B-continued

Herbicide Secondary Preemergence
(C = 100% control)

| | | | | | | | | | | | | | | | | | |
|---|---|---|---|---|---|---|---|---|---|---|---|---|---|---|---|---|---|
| | 0.28 | — | 3 | 3 | — | — | — | — | — | — | — | — | 2 | — | — | — |
| | 0.07 | — | 1 | 3 | — | — | — | — | — | — | — | — | 1 | — | — | — |
| | 0.07 | — | — | — | 3 | — | — | — | 0 | 3 | 0 | 0 | — | 2 | — | — |
| 40 | 5.61 | — | — | — | 3 | — | — | — | 3 | 3 | 2 | 0 | — | 3 | — | — |
| | 5.61 | — | 3 | 3 | — | — | — | — | — | — | — | — | 3 | — | — | — |
| | 1.12 | — | 3 | 3 | — | — | — | — | — | — | — | — | 2 | — | — | — |
| | 1.12 | — | — | — | 3 | — | — | — | 3 | 3 | 1 | 1 | — | 3 | — | — |
| | 0.28 | — | — | — | 3 | — | — | — | 3 | 3 | 0 | 0 | — | 3 | — | — |
| | 0.28 | — | 3 | 3 | — | — | — | — | — | — | — | — | 2 | — | — | — |
| | 0.07 | — | 1 | 3 | — | — | — | — | — | — | — | — | 1 | — | — | — |
| | 0.07 | — | — | — | 3 | — | — | — | 1 | 3 | 0 | 0 | — | 0 | — | — |
| 41 | 11.21 | — | 3 | 3 | — | — | — | — | — | — | — | — | 3 | — | — | — |
| | 11.21 | — | — | — | 3 | — | — | — | 3 | 3 | 2 | 0 | — | 3 | — | — |
| | 5.61 | — | — | — | 3 | — | — | — | 3 | 3 | 1 | 0 | — | 3 | — | — |
| | 5.61 | — | — | — | 3 | — | — | — | 3 | 3 | 1 | 1 | — | 3 | — | — |
| | 5.61 | — | 3 | 3 | — | — | — | — | — | — | — | — | 3 | — | — | — |
| | 5.61 | — | 3 | 3 | — | — | — | — | — | — | — | — | 3 | — | — | — |
| | 1.12 | — | 3 | 3 | — | — | — | — | — | — | — | — | 3 | — | — | — |
| | 1.12 | — | 3 | 3 | — | — | — | — | — | — | — | — | 3 | — | — | — |
| | 1.12 | — | — | — | 3 | — | — | — | 3 | 3 | 1 | 0 | — | 3 | — | — |
| | 1.12 | — | — | — | 3 | — | — | — | 3 | 3 | 0 | 0 | — | 3 | — | — |
| | 0.28 | — | — | — | 3 | — | — | — | 0 | 3 | 0 | 0 | — | 3 | — | — |
| | 0.28 | — | — | — | 3 | — | — | — | 0 | 3 | 0 | 0 | — | 3 | — | — |
| | 0.28 | — | 3 | 3 | — | — | — | — | — | — | — | — | 3 | — | — | — |
| | 0.28 | — | 3 | 3 | — | — | — | — | — | — | — | — | 3 | — | — | — |
| | 0.07 | — | 2 | 3 | — | — | — | — | — | — | — | — | 1 | — | — | — |
| | 0.07 | — | 3 | 3 | — | — | — | — | — | — | — | — | 3 | — | — | — |
| | 0.07 | — | — | — | 3 | — | — | — | 0 | 3 | 0 | 0 | — | 3 | — | — |
| | 0.07 | — | — | — | 3 | — | — | — | 0 | 3 | 0 | 0 | — | 2 | — | — |
| | 0.02 | — | — | — | 0 | — | — | — | 0 | 0 | 0 | 0 | — | 0 | — | — |
| | 0.02 | — | 0 | 3 | — | — | — | — | — | — | — | — | 1 | — | — | — |
| 42 | 11.21 | 0 | 0 | 1 | 0 | — | — | — | 0 | — | — | — | — | — | — | — |
| | 5.61 | 0 | 0 | 0 | 0 | — | — | — | 0 | — | — | — | — | — | — | — |
| | 1.12 | 0 | 0 | 0 | 0 | — | — | — | 0 | — | — | — | — | — | — | — |
| 43 | 5.61 | — | — | — | 3 | — | — | — | 3 | 3 | 3 | 3 | — | 3 | — | — |
| | 5.61 | — | 3 | 3 | — | — | — | — | — | — | — | — | 3 | — | — | — |
| | 1.12 | — | 3 | 3 | — | — | — | — | — | — | — | — | 3 | — | — | — |
| | 1.12 | — | — | — | 3 | — | — | — | 3 | 3 | 3 | 0 | — | 3 | — | — |
| | 0.28 | — | — | — | 3 | — | — | — | 3 | 3 | 0 | 0 | — | 3 | — | — |
| | 0.28 | — | 3 | 3 | — | — | — | — | — | — | — | — | 3 | — | — | — |
| | 0.07 | — | 3 | 3 | — | — | — | — | — | — | — | — | 3 | — | — | — |
| | 0.07 | — | — | — | 3 | — | — | — | N | 3 | 0 | 0 | — | 3 | — | — |
| | 0.02 | — | — | — | 3 | — | — | — | 0 | 3 | 0 | 0 | — | 3 | — | — |
| | 0.02 | — | 3 | 3 | — | — | — | — | — | — | — | — | 2 | — | — | — |
| | 0.00 | — | 0 | 0 | — | — | — | — | — | — | — | — | 0 | — | — | — |
| | 0.00 | — | — | — | 1 | — | — | — | 0 | 0 | 0 | 0 | — | 0 | — | — |
| 44 | 5.61 | — | — | — | 3 | — | — | — | 3 | 3 | 2 | 0 | — | 3 | — | — |
| | 5.61 | — | 3 | 3 | — | — | — | — | — | — | — | — | 3 | — | — | — |
| | 1.12 | — | 3 | 3 | — | — | — | — | — | — | — | — | 3 | — | — | — |
| | 1.12 | — | — | — | 3 | — | — | — | 3 | 3 | 1 | 0 | — | 3 | — | — |
| | 0.28 | — | — | — | 3 | — | — | — | 3 | 3 | 1 | 0 | — | 3 | — | — |
| | 0.28 | — | 3 | 3 | — | — | — | — | — | — | — | — | 3 | — | — | — |
| | 0.07 | — | 1 | 3 | — | — | — | — | — | — | — | — | 1 | — | — | — |
| | 0.07 | — | — | — | 3 | — | — | — | 3 | 3 | 0 | 0 | — | 3 | — | — |
| | 0.02 | — | — | — | 3 | — | — | — | 2 | 2 | 0 | 0 | — | 0 | — | — |
| | 0.02 | — | 2 | 3 | — | — | — | — | — | — | — | — | 0 | — | — | — |
| 45 | 5.61 | — | 3 | 3 | — | — | — | — | — | — | — | — | 3 | — | — | — |
| | 5.61 | — | — | — | 3 | — | — | — | 3 | 3 | 1 | 0 | — | 3 | — | — |
| | 1.12 | — | — | — | 3 | — | — | — | 3 | 3 | 0 | 0 | — | 3 | — | — |
| | 1.12 | — | 3 | 3 | — | — | — | — | — | — | — | — | 2 | — | — | — |
| | 0.28 | — | 0 | 3 | — | — | — | — | — | — | — | — | 0 | — | — | — |
| | 0.28 | — | — | — | 1 | — | — | — | 2 | 3 | 0 | 0 | — | 1 | — | — |
| | 0.07 | — | — | — | 1 | — | — | — | 0 | 0 | 0 | 0 | — | 0 | — | — |
| | 0.07 | — | 0 | 1 | — | — | — | — | — | — | — | — | 0 | — | — | — |
| 47 | 5.61 | — | 3 | 3 | — | — | — | — | — | — | — | — | 3 | — | — | — |
| | 5.61 | — | — | — | 3 | — | — | — | 3 | 3 | 3 | 3 | — | 3 | — | — |
| | 1.12 | — | — | — | 3 | — | — | — | 3 | 3 | 2 | 3 | — | 3 | — | — |
| | 1.12 | — | 3 | 3 | — | — | — | — | — | — | — | — | 3 | — | — | — |
| | 0.28 | — | 3 | 3 | — | — | — | — | — | — | — | — | 3 | — | — | — |
| | 0.28 | — | — | — | 3 | — | — | — | 3 | 3 | 2 | 0 | — | 3 | — | — |
| | 0.07 | — | — | — | 3 | — | — | — | 2 | 3 | 1 | 0 | — | 3 | — | — |
| | 0.07 | — | 3 | 3 | — | — | — | — | — | — | — | — | 3 | — | — | — |
| | 0.02 | — | 3 | 3 | — | — | — | — | — | — | — | — | 3 | — | — | — |
| | 0.02 | — | — | — | 3 | — | — | — | 3 | 3 | 0 | 0 | — | 3 | — | — |
| | 0.00 | — | — | — | 2 | — | — | — | 0 | 0 | 0 | 0 | — | 0 | — | — |
| | 0.00 | — | 0 | 1 | — | — | — | — | — | — | — | — | 0 | — | — | — |
| 49 | 5.61 | — | — | — | 3 | — | — | — | 3 | 3 | 3 | 3 | — | 3 | — | — |
| | 5.61 | — | 3 | 3 | — | — | — | — | — | — | — | — | 3 | — | — | — |
| | 1.12 | — | 3 | 3 | — | — | — | — | — | — | — | — | 3 | — | — | — |
| | 1.12 | — | — | — | 3 | — | — | — | 3 | 3 | 3 | 1 | — | 3 | — | — |

TABLE B-continued

Herbicide Secondary Preemergence
(C = 100% control)

|    |       |   |   |   |   |   |   |   |   |   |   |   |   |   |   |   |
|----|-------|---|---|---|---|---|---|---|---|---|---|---|---|---|---|---|
|    | 0.28  | — | — | — | 3 | — | — | — | 3 | 3 | 0 | 0 | — | 3 | — | — |
|    | 0.28  | — | 3 | 3 | — | — | — | — | — | — | — | — | 3 | — | — | — |
|    | 0.07  | — | 3 | 3 | — | — | — | — | — | — | — | — | 3 | — | — | — |
|    | 0.07  | — | — | — | 3 | — | — | — | 3 | 3 | 0 | 0 | — | 3 | — | — |
|    | 0.02  | — | — | — | 3 | — | — | — | 1 | 3 | 0 | 0 | — | 3 | — | — |
|    | 0.02  | — | 3 | 3 | — | — | — | — | — | — | — | — | 3 | — | — | — |
|    | 0.00  | — | 2 | 0 | — | — | — | — | — | — | — | — | 1 | — | — | — |
|    | 0.00  | — | — | — | 0 | — | — | — | 0 | 2 | 0 | 0 | — | 2 | — | — |
| 50 | 5.61  | — | — | — | 3 | — | — | — | 3 | 3 | 3 | 3 | — | 3 | — | — |
|    | 5.61  | — | 3 | 3 | — | — | — | — | — | — | — | — | 3 | — | — | — |
|    | 1.12  | — | 3 | 3 | — | — | — | — | — | — | — | — | 3 | — | — | — |
|    | 1.12  | — | — | — | 3 | — | — | — | 3 | 3 | 2 | 0 | — | 3 | — | — |
|    | 0.28  | — | — | — | 3 | — | — | — | 3 | 3 | 0 | 0 | — | 3 | — | — |
|    | 0.28  | — | 3 | 3 | — | — | — | — | — | — | — | — | 3 | — | — | — |
|    | 0.07  | — | 3 | 3 | — | — | — | — | — | — | — | — | 3 | — | — | — |
|    | 0.07  | — | — | — | 3 | — | — | — | 1 | 3 | 0 | 0 | — | 3 | — | — |
|    | 0.02  | — | — | — | 2 | — | — | — | 0 | 3 | 0 | 0 | — | 2 | — | — |
|    | 0.02  | — | 3 | 2 | — | — | — | — | — | — | — | — | 2 | — | — | — |
|    | 0.00  | — | 0 | 0 | — | — | — | — | — | — | — | — | 0 | — | — | — |
|    | 0.00  | — | — | — | 0 | — | — | — | 0 | 0 | 0 | 0 | — | 1 | — | — |
| 51 | 5.61  | — | — | — | 3 | — | — | — | 3 | 3 | 2 | 0 | — | 3 | — | — |
|    | 5.61  | — | 3 | 3 | — | — | — | — | — | — | — | — | 3 | — | — | — |
|    | 1.12  | — | 3 | 3 | — | — | — | — | — | — | — | — | 3 | — | — | — |
|    | 1.12  | — | — | — | 3 | — | — | — | 3 | 3 | 0 | 0 | — | 3 | — | — |
|    | 0.28  | — | — | — | 3 | — | — | — | 3 | 3 | 0 | 0 | — | 3 | — | — |
|    | 0.28  | — | 3 | 3 | — | — | — | — | — | — | — | — | 3 | — | — | — |
|    | 0.07  | — | 3 | 3 | — | — | — | — | — | — | — | — | 3 | — | — | — |
|    | 0.07  | — | — | — | 2 | — | — | — | 0 | 3 | 0 | 0 | — | 3 | — | — |
|    | 0.02  | — | — | — | 0 | — | — | — | 0 | 0 | 0 | 0 | — | 0 | — | — |
|    | 0.02  | — | 0 | 1 | — | — | — | — | — | — | — | — | 0 | — | — | — |
|    | 0.00  | — | 0 | 0 | — | — | — | — | — | — | — | — | 0 | — | — | — |
|    | 0.00  | — | — | — | 0 | — | — | — | 0 | 0 | 0 | 0 | — | 0 | — | — |
| 52 | 5.61  | — | — | — | 3 | — | — | — | 3 | 3 | 3 | 3 | — | 3 | — | — |
|    | 5.61  | — | 3 | 3 | — | — | — | — | — | — | — | — | 3 | — | — | — |
|    | 1.12  | — | 3 | 3 | — | — | — | — | — | — | — | — | 3 | — | — | — |
|    | 1.12  | — | — | — | 3 | — | — | — | 3 | 3 | 3 | 1 | — | 3 | — | — |
|    | 0.28  | — | — | — | 3 | — | — | — | 3 | 3 | 0 | 1 | — | 3 | — | — |
|    | 0.28  | — | 3 | 3 | — | — | — | — | — | — | — | — | 3 | — | — | — |
|    | 0.07  | — | 3 | 3 | — | — | — | — | — | — | — | — | 3 | — | — | — |
|    | 0.07  | — | — | — | 3 | — | — | — | 3 | 3 | 0 | 0 | — | 3 | — | — |
|    | 0.02  | — | — | — | 3 | — | — | — | 2 | 3 | 0 | 0 | — | 3 | — | — |
|    | 0.02  | — | 3 | 3 | — | — | — | — | — | — | — | — | 3 | — | — | — |
|    | 0.00  | — | 0 | 2 | — | — | — | — | — | — | — | — | 2 | — | — | — |
|    | 0.00  | — | — | — | 1 | — | — | — | 0 | 0 | 0 | 0 | — | 0 | — | — |
| 53 | 5.61  | 3 | 3 | 3 | 3 | — | — | — | — | — | — | — | — | — | — | — |
|    | 1.12  | 3 | 3 | 3 | 3 | — | — | — | — | — | — | — | — | — | — | — |
|    | 0.28  | 3 | 3 | 3 | 3 | — | — | — | — | — | — | — | — | — | — | — |
|    | 0.07  | 3 | 3 | 3 | 3 | — | — | — | — | — | — | — | — | — | — | — |
|    | 0.02  | 2 | 0 | 2 | 1 | — | — | — | — | — | — | — | — | — | — | — |
|    | 0.01  | N | 0 | 0 | N | — | — | — | — | — | — | — | — | — | — | — |
| 54 | 5.61  | 3 | 3 | 3 | 3 | — | — | — | — | — | — | — | — | — | — | — |
|    | 1.12  | 3 | 3 | 3 | 3 | — | — | — | — | — | — | — | — | — | — | — |
|    | 0.28  | 3 | 3 | 3 | 3 | — | — | — | — | — | — | — | — | — | — | — |
|    | 0.07  | 3 | 3 | 3 | 3 | — | — | — | — | — | — | — | — | — | — | — |
|    | 0.02  | 2 | 3 | 3 | 2 | — | — | — | — | — | — | — | — | — | — | — |
|    | 0.01  | 0 | 3 | 3 | 2 | — | — | — | — | — | — | — | — | — | — | — |
| 55 | 5.61  | 3 | 3 | 3 | 3 | — | — | — | 3 | — | — | — | — | — | — | — |
|    | 1.12  | 3 | 3 | 3 | 3 | — | — | — | 3 | — | — | — | — | — | — | — |
|    | 0.28  | 3 | 3 | 3 | 3 | — | — | — | 2 | — | — | — | — | — | — | — |
|    | 0.07  | 0 | 0 | 0 | 0 | — | — | — | 1 | — | — | — | — | — | — | — |
| 56 | 5.61  | 3 | 3 | 3 | 3 | — | — | — | 2 | — | — | — | — | — | — | — |
|    | 1.12  | 3 | 3 | 3 | 3 | — | — | — | 3 | — | — | — | — | — | — | — |
|    | 0.28  | 3 | 3 | 3 | 3 | — | — | — | 3 | — | — | — | — | — | — | — |
|    | 0.07  | 3 | 3 | 3 | 3 | — | — | — | 3 | — | — | — | — | — | — | — |
|    | 0.02  | 3 | 3 | 3 | 3 | — | — | — | 3 | — | — | — | — | — | — | — |
|    | 0.01  | 3 | 3 | 3 | 3 | — | — | — | 3 | — | — | — | — | — | — | — |
| 57 | 5.61  | 3 | 3 | 3 | 3 | — | — | — | 3 | — | — | — | — | — | — | — |
|    | 1.12  | 3 | 3 | 3 | 3 | — | — | — | 3 | — | — | — | — | — | — | — |
|    | 0.28  | 3 | 3 | 3 | 3 | — | — | — | 3 | — | — | — | — | — | — | — |
|    | 0.07  | 3 | 3 | 3 | 3 | — | — | — | 3 | — | — | — | — | — | — | — |
|    | 0.02  | 3 | 3 | 3 | 3 | — | — | — | 3 | — | — | — | — | — | — | — |
|    | 0.01  | 2 | 3 | 3 | 3 | — | — | — | 1 | — | — | — | — | — | — | — |
| 58 | 11.21 | 2 | 3 | 3 | 2 | — | — | — | 3 | — | — | — | — | — | — | — |
|    | 5.61  | 2 | 3 | 3 | 2 | — | — | — | 3 | — | — | — | — | — | — | — |
|    | 1.12  | 0 | 3 | 3 | N | — | — | — | 1 | — | — | — | — | — | — | — |
| 59 | 5.61  | 3 | 3 | 3 | 3 | — | — | — | 3 | — | — | — | — | — | — | — |
|    | 1.12  | 3 | 3 | 3 | 3 | — | — | — | 3 | — | — | — | — | — | — | — |
|    | 0.28  | 3 | 3 | 3 | 3 | — | — | — | 3 | — | — | — | — | — | — | — |
|    | 0.07  | 3 | 3 | 3 | 3 | — | — | — | 3 | — | — | — | — | — | — | — |
|    | 0.02  | 2 | 3 | 3 | 3 | — | — | — | 3 | — | — | — | — | — | — | — |

TABLE B-continued

Herbicide Secondary Preemergence
(C = 100% control)

| | | | | | | | | | | | | | | | | |
|---|---|---|---|---|---|---|---|---|---|---|---|---|---|---|---|---|
| | 0.00 | 0 | 0 | 2 | 0 | — | — | — | 1 | — | — | — | — | — | — | — |
| 60 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 3 | 3 | 3 | 3 | — | — | — | 3 | — | — | — | — | — | — | — |
| | 0.07 | 1 | 3 | 3 | 3 | — | — | — | 3 | — | — | — | — | — | — | — |
| | 0.02 | 0 | 1 | 3 | 3 | — | — | — | 1 | — | — | — | — | — | — | — |
| | 0.00 | 0 | 0 | 1 | 0 | — | — | — | 0 | — | — | — | — | — | — | — |
| 61 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 3 | 3 | 3 | 3 | — | — | — | 3 | — | — | — | — | — | — | — |
| | 0.07 | 2 | 3 | 3 | 3 | — | — | — | 3 | — | — | — | — | — | — | — |
| | 0.02 | 1 | 0 | 2 | 0 | — | — | — | 1 | — | — | — | — | — | — | — |
| 62 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 3 | 3 | 3 | 3 | — | — | — | 3 | — | — | — | — | — | — | — |
| | 0.07 | 1 | 2 | 3 | 3 | — | — | — | 2 | — | — | — | — | — | — | — |
| | 0.02 | 0 | 0 | 3 | 0 | — | — | — | 0 | — | — | — | — | — | — | — |
| | 0.01 | 0 | 0 | 0 | 0 | — | — | — | 0 | — | — | — | — | — | — | — |
| 63 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 3 | 3 | 3 | 3 | — | — | — | 3 | — | — | — | — | — | — | — |
| | 0.07 | 3 | 3 | 3 | 3 | — | — | — | 3 | — | — | — | — | — | — | — |
| | 0.02 | 2 | 0 | 3 | 1 | — | — | — | 2 | — | — | — | — | — | — | — |
| | 0.01 | 0 | 0 | 3 | 0 | — | — | — | 1 | — | — | — | — | — | — | — |
| 64 | 5.61 | 3 | 3 | 3 | 3 | — | — | — | 3 | — | — | — | — | — | — | — |
| | 1.12 | 3 | 3 | 1 | 3 | — | — | — | 1 | — | — | — | — | — | — | — |
| | 0.28 | 0 | 0 | 1 | 0 | — | — | — | 1 | — | — | — | — | — | — | — |
| | 0.07 | 0 | 0 | 0 | 0 | — | — | — | 0 | — | — | — | — | — | — | — |
| | 0.02 | 0 | 0 | 1 | 0 | — | — | — | 0 | — | — | — | — | — | — | — |
| | 0.01 | 0 | 0 | N | 0 | — | — | — | 0 | — | — | — | — | — | — | — |
| 65 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 3 | 3 | 3 | 3 | — | — | — | 3 | — | — | — | — | — | — | — |
| | 0.07 | 3 | 3 | 3 | 3 | — | — | — | 2 | — | — | — | — | — | — | — |
| | 0.02 | 3 | 3 | 3 | 2 | — | — | — | 0 | — | — | — | — | — | — | — |
| | 0.00 | 1 | 2 | 3 | 2 | — | — | — | 0 | — | — | — | — | — | — | — |
| 66 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 2 | 3 | 3 | 3 | — | — | — | 2 | — | — | — | — | — | — | — |
| | 0.07 | 0 | 0 | 3 | 0 | — | — | — | 0 | — | — | — | — | — | — | — |
| | 0.02 | 0 | 0 | 3 | 0 | — | — | — | 0 | — | — | — | — | — | — | — |
| | 0.01 | N | 0 | 1 | 0 | — | — | — | 0 | — | — | — | — | — | — | — |
| 67 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 3 | 2 | 3 | 3 | — | — | — | 3 | — | — | — | — | — | — | — |
| | 0.07 | 3 | 0 | 3 | 0 | — | — | — | 2 | — | — | — | — | — | — | — |
| | 0.02 | 0 | 0 | 0 | 0 | — | — | — | 1 | — | — | — | — | — | — | — |
| | 0.01 | 0 | 0 | 0 | 0 | — | — | — | 0 | — | — | — | — | — | — | — |
| 68 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 1 | 3 | 3 | 3 | — | — | — | 3 | — | — | — | — | — | — | — |
| | 0.07 | 0 | 2 | 2 | 0 | — | — | — | 2 | — | — | — | — | — | — | — |
| | 0.02 | 0 | 0 | 1 | 0 | — | — | — | 1 | — | — | — | — | — | — | — |
| | 0.01 | 0 | 0 | 0 | 0 | — | — | — | 1 | — | — | — | — | — | — | — |
| 69 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 3 | 3 | 3 | 3 | — | — | — | 3 | — | — | — | — | — | — | — |
| | 0.07 | 3 | 3 | 3 | 3 | — | — | — | 3 | — | — | — | — | — | — | — |
| | 0.02 | 3 | 3 | 3 | 2 | — | — | — | 3 | — | — | — | — | — | — | — |
| | 0.01 | 1 | 2 | 3 | 1 | — | — | — | 0 | — | — | — | — | — | — | — |
| 70 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 3 | 3 | 3 | 3 | — | — | — | 3 | — | — | — | — | — | — | — |
| | 0.07 | 3 | 2 | 3 | 1 | — | — | — | 1 | — | — | — | — | — | — | — |
| | 0.02 | 0 | 1 | 2 | 0 | — | — | — | 1 | — | — | — | — | — | — | — |
| | 0.01 | 1 | 0 | 1 | 0 | — | — | — | N | — | — | — | — | — | — | — |
| 71 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 3 | 3 | 3 | 3 | — | — | — | 3 | — | — | — | — | — | — | — |
| | 0.07 | 2 | 0 | 3 | 1 | — | — | — | 2 | — | — | — | — | — | — | — |
| | 0.02 | 0 | 0 | 2 | 0 | — | — | — | 1 | — | — | — | — | — | — | — |
| 72 | 5.61 | — | — | — | 3 | — | — | — | 3 | 3 | 3 | 3 | — | 3 | — | — |
| | 5.61 | — | 3 | 3 | — | — | — | — | — | — | — | — | 3 | — | — | — |
| | 1.12 | — | 3 | 3 | — | — | — | — | — | — | — | — | 3 | — | — | — |
| | 1.12 | — | — | — | 3 | — | — | — | 3 | 3 | 2 | 2 | — | 3 | — | — |
| | 0.28 | — | — | — | 3 | — | — | — | 3 | 3 | 1 | 0 | — | 3 | — | — |
| | 0.28 | — | 3 | 3 | — | — | — | — | — | — | — | — | 3 | — | — | — |
| | 0.07 | — | 3 | 3 | — | — | — | — | — | — | — | — | 3 | — | — | — |
| | 0.07 | — | — | — | 3 | — | — | — | 3 | 3 | 1 | 0 | — | 3 | — | — |
| | 0.02 | — | — | — | 3 | — | — | — | 3 | 3 | 0 | 0 | — | 3 | — | — |

TABLE B-continued

Herbicide Secondary Preemergence
(C = 100% control)

| | | | | | | | | | | | | | | | | |
|---|---|---|---|---|---|---|---|---|---|---|---|---|---|---|---|---|
| | 0.02 | — | 3 | 3 | — | — | — | — | — | — | — | — | 3 | — | — | — |
| | 0.00 | — | 3 | 3 | — | — | — | — | — | — | — | — | 2 | — | — | — |
| | 0.00 | — | — | — | 3 | — | — | — | 0 | 3 | 0 | 0 | — | 2 | — | — |
| 73 | 5.61 | — | — | — | 3 | — | — | — | 3 | 3 | 3 | 3 | — | 3 | — | — |
| | 5.61 | — | 3 | 3 | — | — | — | — | — | — | — | — | 3 | — | — | — |
| | 1.12 | — | 3 | 3 | — | — | — | — | — | — | — | — | 3 | — | — | — |
| | 1.12 | — | — | — | 3 | — | — | — | 3 | 3 | 1 | 2 | — | 3 | — | — |
| | 0.28 | — | — | — | 3 | — | — | — | 3 | 3 | 1 | 1 | — | 3 | — | — |
| | 0.28 | — | 3 | 3 | — | — | — | — | — | — | — | — | 3 | — | — | — |
| | 0.07 | — | 3 | 3 | — | — | — | — | — | — | — | — | 3 | — | — | — |
| | 0.07 | — | — | — | 3 | — | — | — | 3 | 3 | 1 | 0 | — | 3 | — | — |
| | 0.02 | — | — | — | 3 | — | — | — | 3 | 3 | 0 | 0 | — | 2 | — | — |
| | 0.02 | — | 3 | 3 | — | — | — | — | — | — | — | — | 3 | — | — | — |
| 74 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 3 | 3 | 3 | 3 | — | — | — | 3 | — | — | — | — | — | — | — |
| | 0.07 | 0 | 3 | 3 | 3 | — | — | — | 0 | — | — | — | — | — | — | — |
| | 0.02 | 0 | 3 | 2 | 3 | — | — | — | 0 | — | — | — | — | — | — | — |
| | 0.01 | 0 | 2 | 2 | 2 | — | — | — | 0 | — | — | — | — | — | — | — |
| 75 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 0 | 3 | 3 | 3 | — | — | — | 3 | — | — | — | — | — | — | — |
| | 0.07 | 0 | 1 | 3 | 2 | — | — | — | 0 | — | — | — | — | — | — | — |
| 76 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 2 | 3 | 3 | 3 | — | — | — | 0 | — | — | — | — | — | — | — |
| | 0.07 | 0 | 2 | 3 | 0 | — | — | — | 0 | — | — | — | — | — | — | — |
| | 0.02 | 0 | 0 | 3 | 0 | — | — | — | 0 | — | — | — | — | — | — | — |
| | 0.01 | 0 | 0 | 0 | 0 | — | — | — | N | — | — | — | — | — | — | — |
| 77 | 5.61 | 3 | 3 | 3 | 3 | — | — | — | 3 | — | — | — | — | — | — | — |
| | 1.12 | 3 | 3 | 3 | 3 | — | — | — | 3 | — | — | — | — | — | — | — |
| | 0.28 | 3 | 3 | 3 | 3 | — | — | — | 3 | — | — | — | — | — | — | — |
| | 0.07 | 3 | 3 | 3 | 2 | — | — | — | 0 | — | — | — | — | — | — | — |
| | 0.02 | 0 | 0 | 3 | 0 | — | — | — | 0 | — | — | — | — | — | — | — |
| | 0.01 | 1 | 1 | 3 | 1 | — | — | — | 0 | — | — | — | — | — | — | — |
| 78 | 5.61 | — | 3 | 3 | — | — | — | — | — | — | — | — | 3 | — | — | — |
| | 5.61 | — | — | — | 3 | — | — | — | 3 | 3 | 2 | 3 | — | 3 | — | — |
| | 1.12 | — | — | — | 3 | — | — | — | 3 | 3 | 0 | 1 | — | 3 | — | — |
| | 1.12 | — | 3 | 3 | — | — | — | — | — | — | — | — | 3 | — | — | — |
| | 0.28 | — | 3 | 3 | — | — | — | — | — | — | — | — | 3 | — | — | — |
| | 0.28 | — | — | — | 3 | — | — | — | 3 | 3 | 0 | 2 | — | 3 | — | — |
| | 0.07 | — | — | — | 2 | — | — | — | 0 | 2 | 0 | 0 | — | 0 | — | — |
| | 0.07 | — | 2 | 3 | — | — | — | — | — | — | — | — | 1 | — | — | — |
| | 0.02 | — | 0 | 1 | — | — | — | — | — | — | — | — | 1 | — | — | — |
| | 0.02 | — | — | — | 2 | — | — | — | 0 | 0 | 0 | 0 | — | 0 | — | — |
| | 0.01 | — | — | — | 0 | — | — | — | 0 | 0 | 0 | 0 | — | 0 | — | — |
| | 0.01 | — | 0 | 0 | — | — | — | — | — | — | — | — | 0 | — | — | — |
| 79 | 5.61 | — | 3 | 3 | — | — | — | — | — | — | — | — | 3 | — | — | — |
| | 5.61 | — | — | — | 3 | — | — | — | 3 | 3 | 2 | 3 | — | 3 | — | — |
| | 1.12 | — | — | — | 3 | — | — | — | 3 | 3 | 1 | 0 | — | 3 | — | — |
| | 1.12 | — | 3 | 3 | — | — | — | — | — | — | — | — | 3 | — | — | — |
| | 0.28 | — | 3 | 3 | — | — | — | — | — | — | — | — | 3 | — | — | — |
| | 0.28 | — | — | — | 3 | — | — | — | 3 | 3 | 0 | 1 | — | 2 | — | — |
| | 0.07 | — | — | — | 3 | — | — | — | 3 | 3 | 0 | 0 | — | 2 | — | — |
| | 0.07 | — | 3 | 3 | — | — | — | — | — | — | — | — | 1 | — | — | — |
| | 0.02 | — | 0 | 3 | — | — | — | — | — | — | — | — | 1 | — | — | — |
| | 0.02 | — | — | — | 1 | — | — | — | 1 | 3 | 0 | 0 | — | 0 | — | — |
| | 0.00 | — | — | — | 0 | — | — | — | 0 | 0 | 0 | 0 | — | 0 | — | — |
| | 0.00 | — | 0 | 0 | — | — | — | — | — | — | — | — | 0 | — | — | — |
| 80 | 5.61 | — | 3 | 3 | — | — | — | — | — | — | — | — | 3 | — | — | — |
| | 5.61 | — | — | — | 3 | — | — | — | 3 | 3 | 2 | 2 | — | 3 | — | — |
| | 1.12 | — | — | — | 3 | — | — | — | 3 | 3 | 1 | 2 | — | 3 | — | — |
| | 1.12 | — | 3 | 3 | — | — | — | — | — | — | — | — | 3 | — | — | — |
| | 0.28 | — | 2 | 3 | — | — | — | — | — | — | — | — | 2 | — | — | — |
| | 0.28 | — | — | — | 3 | — | — | — | 3 | 3 | 0 | 2 | — | 3 | — | — |
| | 0.07 | — | — | — | 1 | — | — | — | 3 | 3 | 0 | 0 | — | 2 | — | — |
| | 0.07 | — | 0 | 3 | — | — | — | — | — | — | — | — | 1 | — | — | — |
| | 0.02 | — | 0 | 0 | — | — | — | — | — | — | — | — | 0 | — | — | — |
| | 0.02 | — | — | — | 0 | — | — | — | 3 | 0 | 0 | 0 | — | 0 | — | — |
| 81 | 5.61 | — | — | — | 3 | — | — | — | 3 | 3 | 3 | 3 | — | 3 | — | — |
| | 5.61 | — | 3 | 3 | — | — | — | — | — | — | — | — | 3 | — | — | — |
| | 1.12 | — | 3 | 3 | — | — | — | — | — | — | — | — | 3 | — | — | — |
| | 1.12 | — | — | — | 3 | — | — | — | 3 | 3 | 2 | 3 | — | 3 | — | — |
| | 0.28 | — | — | — | 3 | — | — | — | 3 | 3 | 0 | 3 | — | 3 | — | — |
| | 0.28 | — | 3 | 3 | — | — | — | — | — | — | — | — | 3 | — | — | — |
| | 0.07 | — | 3 | 3 | — | — | — | — | — | — | — | — | 3 | — | — | — |
| | 0.07 | — | — | — | 3 | — | — | — | 3 | 3 | 0 | 1 | — | 3 | — | — |
| | 0.02 | — | — | — | 3 | — | — | — | 3 | 3 | 2 | 0 | — | 0 | — | — |
| | 0.02 | — | 3 | 3 | — | — | — | — | — | — | — | — | 2 | — | — | — |
| | 0.00 | — | 0 | 3 | — | — | — | — | — | — | — | — | 0 | — | — | — |

TABLE B-continued

Herbicide Secondary Preemergence
(C = 100% control)

| | | | | | | | | | | | | | | | |
|---|---|---|---|---|---|---|---|---|---|---|---|---|---|---|---|
| | 0.00 | — | — | — | 0 | — | — | — | 3 | 3 | 0 | 0 | — | 2 | — | — |
| 82 | 5.61 | — | — | — | 3 | — | — | — | 3 | 3 | 3 | 3 | — | 3 | — | — |
| | 5.61 | — | 3 | 3 | — | — | — | — | — | — | — | — | 3 | — | — | — |
| | 1.12 | — | 3 | 3 | — | — | — | — | — | — | — | — | 3 | — | — | — |
| | 1.12 | — | — | — | 3 | — | — | — | 3 | 3 | 2 | 3 | — | 3 | — | — |
| | 0.28 | — | — | — | 3 | — | — | — | 3 | 3 | 0 | 2 | — | 3 | — | — |
| | 0.28 | — | 3 | 3 | — | — | — | — | — | — | — | — | 3 | — | — | — |
| | 0.07 | — | 3 | 3 | — | — | — | — | — | — | — | — | 3 | — | — | — |
| | 0.07 | — | — | — | 3 | — | — | — | 3 | 3 | 0 | 0 | — | 3 | — | — |
| | 0.02 | — | — | — | 3 | — | — | — | 3 | 3 | 0 | 0 | — | 1 | — | — |
| | 0.02 | — | 0 | 3 | — | — | — | — | — | — | — | — | 2 | — | — | — |
| | 0.00 | — | 0 | 2 | — | — | — | — | — | — | — | — | 0 | — | — | — |
| | 0.00 | — | — | — | 0 | — | — | — | 2 | 3 | 0 | 0 | — | 0 | — | — |
| 83 | 5.61 | — | 3 | 3 | — | — | — | — | — | — | — | — | 3 | — | — | — |
| | 5.61 | — | — | — | 3 | — | — | — | 3 | 3 | 1 | 2 | — | 3 | — | — |
| | 1.12 | — | — | — | 3 | — | — | — | 3 | 3 | 0 | 2 | — | 3 | — | — |
| | 1.12 | — | 3 | 3 | — | — | — | — | — | — | — | — | 3 | — | — | — |
| | 0.28 | — | 3 | 3 | — | — | — | — | — | — | — | — | 2 | — | — | — |
| | 0.28 | — | — | — | 3 | — | — | — | 0 | 3 | 0 | 0 | — | 3 | — | — |
| | 0.07 | — | — | — | 3 | — | — | — | 0 | 3 | 0 | 0 | — | 0 | — | — |
| | 0.07 | — | 0 | 3 | — | — | — | — | — | — | — | — | 0 | — | — | — |
| 84 | 5.61 | — | 3 | 3 | — | — | — | — | — | — | — | — | 3 | — | — | — |
| | 5.61 | — | — | — | 3 | — | — | — | 3 | 3 | 0 | 0 | — | 3 | — | — |
| | 1.12 | — | — | — | 0 | — | — | — | 0 | 3 | 0 | 0 | — | 0 | — | — |
| | 1.12 | — | 3 | 2 | — | — | — | — | — | — | — | — | 1 | — | — | — |
| | 0.28 | — | 0 | 0 | — | — | — | — | — | — | — | — | 0 | — | — | — |
| | 0.28 | — | — | — | 0 | — | — | — | 0 | 0 | 0 | 0 | — | 0 | — | — |
| | 0.07 | — | — | — | 0 | — | — | — | 0 | 0 | 0 | 0 | — | 0 | — | — |
| | 0.07 | — | 0 | 0 | — | — | — | — | — | — | — | — | 0 | — | — | — |
| | 0.02 | — | 0 | 0 | — | — | — | — | — | — | — | — | 0 | — | — | — |
| | 0.02 | — | — | — | 0 | — | — | — | 0 | 0 | 0 | 0 | — | 0 | — | — |
| 85 | 5.61 | — | — | — | 3 | — | — | — | 3 | 3 | 0 | 0 | — | 3 | — | — |
| | 5.61 | — | 3 | 3 | — | — | — | — | — | — | — | — | 3 | — | — | — |
| | 1.12 | — | 0 | 1 | — | — | — | — | — | — | — | — | 0 | — | — | — |
| | 1.12 | — | — | — | 0 | — | — | — | 0 | 0 | 0 | 0 | — | 2 | — | — |
| | 0.28 | — | — | — | 0 | — | — | — | 0 | 0 | 0 | 0 | — | 0 | — | — |
| | 0.28 | — | 0 | 0 | — | — | — | — | — | — | — | — | 0 | — | — | — |
| | 0.07 | — | 0 | 0 | — | — | — | — | — | — | — | — | 0 | — | — | — |
| | 0.07 | — | — | — | 0 | — | — | — | 0 | 0 | 0 | 0 | — | 0 | — | — |
| 86 | 5.61 | — | — | — | 3 | — | — | — | 3 | 3 | 3 | 3 | — | 3 | — | — |
| | 5.61 | — | 3 | 3 | — | — | — | — | — | — | — | — | 3 | — | — | — |
| | 1.12 | — | — | — | 3 | — | — | — | 3 | 3 | 1 | 2 | — | 3 | — | — |
| | 1.12 | — | 3 | 3 | — | — | — | — | — | — | — | — | 3 | — | — | — |
| | 0.28 | — | 3 | 3 | — | — | — | — | — | — | — | — | 3 | — | — | — |
| | 0.28 | — | — | — | 3 | — | — | — | 3 | 3 | 0 | 0 | — | 3 | — | — |
| | 0.07 | — | 3 | 3 | — | — | — | — | — | — | — | — | 3 | — | — | — |
| | 0.07 | — | — | — | 3 | — | — | — | 3 | 3 | 0 | 0 | — | 3 | — | — |
| | 0.02 | — | — | — | 3 | — | — | — | 3 | 3 | 0 | 0 | — | 0 | — | — |
| | 0.02 | — | 2 | 3 | — | — | — | — | — | — | — | — | 3 | — | — | — |
| | 0.00 | — | 0 | 2 | — | — | — | — | — | — | — | — | 0 | — | — | — |
| | 0.00 | — | — | — | 0 | — | — | — | 0 | 2 | 0 | 0 | — | 0 | — | — |
| 87 | 5.61 | — | — | — | 3 | — | — | — | 3 | 3 | 2 | 3 | — | 3 | — | — |
| | 5.61 | — | 3 | 3 | — | — | — | — | — | — | — | — | 3 | — | — | — |
| | 1.12 | — | — | — | 3 | — | — | — | 3 | 3 | 0 | 2 | — | 3 | — | — |
| | 1.12 | — | 3 | 3 | — | — | — | — | — | — | — | — | 3 | — | — | — |
| | 0.28 | — | — | — | 3 | — | — | — | 3 | 3 | 0 | 0 | — | 3 | — | — |
| | 0.28 | — | 3 | 3 | — | — | — | — | — | — | — | — | 3 | — | — | — |
| | 0.07 | — | — | — | 3 | — | — | — | 1 | 3 | 0 | 0 | — | 0 | — | — |
| | 0.07 | — | 3 | 3 | — | — | — | — | — | — | — | — | 3 | — | — | — |
| | 0.02 | — | — | — | 0 | — | — | — | 0 | 0 | 0 | 0 | — | 0 | — | — |
| | 0.02 | — | 0 | 2 | — | — | — | — | — | — | — | — | 0 | — | — | — |
| 88 | 10.20 | — | 3 | 3 | — | — | — | — | — | — | — | — | 3 | — | — | — |
| | 10.20 | — | — | — | 3 | — | — | — | 3 | 3 | 3 | 3 | — | 3 | — | — |
| | 5.61 | — | — | — | 3 | — | — | — | 3 | 3 | 3 | 3 | — | 3 | — | — |
| | 5.61 | — | 3 | 3 | — | — | — | — | — | — | — | — | 3 | — | — | — |
| | 1.12 | — | — | — | 3 | — | — | — | 3 | 3 | 3 | 3 | — | 3 | — | — |
| | 1.12 | — | 3 | 3 | — | — | — | — | — | — | — | — | 3 | — | — | — |
| | 0.28 | — | 3 | 3 | — | — | — | — | — | — | — | — | 3 | — | — | — |
| | 0.28 | — | — | — | 3 | — | — | — | 3 | 3 | 2 | 3 | — | 3 | — | — |
| | 0.07 | — | 3 | 3 | — | — | — | — | — | — | — | — | 3 | — | — | — |
| | 0.07 | — | — | — | 3 | — | — | — | 3 | 3 | 1 | 2 | — | 3 | — | — |
| | 0.02 | — | — | — | 1 | — | — | — | 0 | 3 | 0 | N | — | 2 | — | — |
| | 0.02 | — | 0 | 2 | — | — | — | — | — | — | — | — | 2 | — | — | — |
| 89 | 5.61 | — | — | — | 3 | — | — | — | 3 | 3 | 0 | 2 | — | 3 | — | — |
| | 5.61 | — | 3 | 3 | — | — | — | — | — | — | — | — | 2 | — | — | — |
| | 1.12 | — | 3 | 2 | — | — | — | — | — | — | — | — | 3 | — | — | — |
| | 1.12 | — | — | — | 3 | — | — | — | 3 | 3 | 0 | 1 | — | 3 | — | — |
| | 0.28 | — | — | — | 1 | — | — | — | 0 | 3 | 0 | 0 | — | 0 | — | — |
| | 0.28 | — | 0 | 0 | — | — | — | — | — | — | — | — | 0 | — | — | — |
| | 0.07 | — | 0 | 0 | — | — | — | — | — | — | — | — | 0 | — | — | — |

TABLE B-continued

Herbicide Secondary Preemergence
(C = 100% control)

| # | Rate | | | | | | | | | | | | | | | |
|---|------|---|---|---|---|---|---|---|---|---|---|---|---|---|---|---|
|  | 0.07 | — | — | — | 0 | — | — | — | 0 | 0 | 0 | 0 | — | 0 | — | — |
|  | 0.02 | — | 0 | 0 | — | — | — | — | — | — | — | — | 0 | — | — | — |
|  | 0.02 | — | — | — | 0 | — | — | — | 0 | 0 | 0 | 0 | — | 0 | — | — |
| 90 | 5.61 | — | — | — | 3 | — | — | — | 3 | 3 | 2 | 2 | — | 3 | — | — |
|  | 5.61 | — | 3 | 3 | — | — | — | — | — | — | — | — | 3 | — | — | — |
|  | 1.12 | — | 3 | 3 | — | — | — | — | — | — | — | — | 3 | — | — | — |
|  | 1.12 | — | — | — | 3 | — | — | — | 3 | 3 | 1 | 3 | — | 3 | — | — |
|  | 0.28 | — | 3 | 3 | — | — | — | — | — | — | — | — | 3 | — | — | — |
|  | 0.28 | — | — | — | 3 | — | — | — | 3 | 3 | 0 | 0 | — | 3 | — | — |
|  | 0.07 | — | — | — | 3 | — | — | — | 3 | 3 | 0 | 0 | — | 3 | — | — |
|  | 0.07 | — | 3 | 3 | — | — | — | — | — | — | — | — | 2 | — | — | — |
|  | 0.02 | — | 0 | 3 | — | — | — | — | — | — | — | — | 0 | — | — | — |
|  | 0.02 | — | — | — | 1 | — | — | — | 0 | 3 | 0 | 0 | — | 3 | — | — |
|  | 0.00 | — | — | — | 0 | — | — | — | 0 | 0 | 0 | 0 | — | 0 | — | — |
|  | 0.00 | — | 0 | 0 | — | — | — | — | — | — | — | — | 1 | — | — | — |
| 91 | 5.61 | — | — | — | 3 | — | — | — | 3 | 3 | 1 | 3 | — | 3 | — | — |
|  | 5.61 | — | 3 | 3 | — | — | — | — | — | — | — | — | 3 | — | — | — |
|  | 1.12 | — | — | — | 3 | — | — | — | 3 | 3 | 0 | 3 | — | 3 | — | — |
|  | 1.12 | — | 3 | 3 | — | — | — | — | — | — | — | — | 3 | — | — | — |
|  | 0.28 | — | — | — | 3 | — | — | — | 2 | 3 | 0 | 2 | — | 2 | — | — |
|  | 0.28 | — | 3 | 3 | — | — | — | — | — | — | — | — | 3 | — | — | — |
|  | 0.07 | — | 2 | 3 | — | — | — | — | — | — | — | — | 1 | — | — | — |
|  | 0.07 | — | — | — | 3 | — | — | — | 0 | 3 | 0 | 0 | — | 0 | — | — |
|  | 0.02 | — | 0 | 0 | — | — | — | — | — | — | — | — | 1 | — | — | — |
|  | 0.02 | — | — | — | 0 | — | — | — | 0 | 0 | 0 | 0 | — | 0 | — | — |
| 92 | 5.61 | — | 3 | 3 | — | — | — | — | — | — | — | — | 3 | — | — | — |
|  | 5.61 | — | — | — | 3 | — | — | — | 3 | 3 | 2 | 3 | — | 3 | — | — |
|  | 1.12 | — | — | — | 3 | — | — | — | 3 | 3 | 1 | 2 | — | 3 | — | — |
|  | 1.12 | — | 3 | 3 | — | — | — | — | — | — | — | — | 3 | — | — | — |
|  | 0.28 | — | 3 | 3 | — | — | — | — | — | — | — | — | 3 | — | — | — |
|  | 0.28 | — | — | — | 3 | — | — | — | 3 | 3 | 1 | N | — | 3 | — | — |
|  | 0.07 | — | — | — | 3 | — | — | — | 3 | 3 | 0 | 2 | — | 2 | — | — |
|  | 0.07 | — | 3 | 3 | — | — | — | — | — | — | — | — | 3 | — | — | — |
|  | 0.02 | — | — | — | 3 | — | — | — | 2 | 3 | 0 | 1 | — | 1 | — | — |
|  | 0.02 | — | 0 | 3 | — | — | — | — | — | — | — | — | 2 | — | — | — |
| 93 | 11.21 | — | — | — | 2 | — | — | — | 1 | 3 | 0 | 1 | — | 0 | — | — |
|  | 11.21 | — | 0 | 2 | — | — | — | — | — | — | — | — | 0 | — | — | — |
|  | 5.61 | — | — | — | 0 | — | — | — | 0 | 3 | 0 | 0 | — | 0 | — | — |
|  | 5.61 | — | 0 | 1 | — | — | — | — | — | — | — | — | 0 | — | — | — |
|  | 1.12 | — | — | — | 0 | — | — | — | 0 | 0 | 0 | 0 | — | 0 | — | — |
|  | 1.12 | — | 0 | 0 | — | — | — | — | — | — | — | — | 0 | — | — | — |
| 94 | 5.61 | — | — | — | 3 | — | — | — | 3 | 3 | 1 | 1 | — | 3 | — | — |
|  | 5.61 | — | 3 | 3 | — | — | — | — | — | — | — | — | 3 | — | — | — |
|  | 1.12 | — | 3 | 3 | — | — | — | — | — | — | — | — | 3 | — | — | — |
|  | 1.12 | — | — | — | 3 | — | — | — | 0 | 3 | 0 | N | — | 2 | — | — |
|  | 0.28 | — | — | — | 0 | — | — | — | 0 | 0 | 0 | 0 | — | 0 | — | — |
|  | 0.28 | — | 0 | 0 | — | — | — | — | — | — | — | — | 0 | — | — | — |
|  | 0.07 | — | — | — | 0 | — | — | — | 0 | 0 | 0 | 0 | — | 0 | — | — |
|  | 0.07 | — | 0 | 0 | — | — | — | — | — | — | — | — | 0 | — | — | — |
| 95 | 10.20 | — | — | — | 3 | — | — | — | 3 | 3 | 2 | 3 | — | 3 | — | — |
|  | 10.20 | — | 3 | 3 | — | — | — | — | — | — | — | — | 3 | — | — | — |
|  | 5.61 | — | — | — | 3 | — | — | — | 3 | 3 | 3 | 3 | — | 3 | — | — |
|  | 5.61 | — | 3 | 3 | — | — | — | — | — | — | — | — | 3 | — | — | — |
|  | 1.12 | — | — | — | 3 | — | — | — | 3 | 3 | 0 | 3 | — | 3 | — | — |
|  | 1.12 | — | 3 | 3 | — | — | — | — | — | — | — | — | 3 | — | — | — |
|  | 0.28 | — | 3 | 3 | — | — | — | — | — | — | — | — | 3 | — | — | — |
|  | 0.28 | — | — | — | 3 | — | — | — | 2 | 3 | 0 | 2 | — | 3 | — | — |
|  | 0.07 | — | 0 | 1 | — | — | — | — | — | — | — | — | 2 | — | — | — |
|  | 0.07 | — | — | — | 3 | — | — | — | 1 | 3 | 0 | 0 | — | 2 | — | — |
|  | 0.02 | — | — | — | 0 | — | — | — | 1 | 0 | 0 | 0 | — | 0 | — | — |
|  | 0.02 | — | 0 | 0 | — | — | — | — | — | — | — | — | 0 | — | — | — |
| 96 | 10.20 | — | — | — | 3 | — | — | — | 3 | 3 | 1 | 2 | — | 3 | — | — |
|  | 10.20 | — | 3 | 3 | — | — | — | — | — | — | — | — | 3 | — | — | — |
|  | 5.61 | — | — | — | 3 | — | — | — | 3 | 3 | 0 | 0 | — | 2 | — | — |
|  | 5.61 | — | 3 | 3 | — | — | — | — | — | — | — | — | 3 | — | — | — |
|  | 1.12 | — | — | — | 2 | — | — | — | 1 | 3 | 0 | 0 | — | 0 | — | — |
|  | 1.12 | — | 1 | 3 | — | — | — | — | — | — | — | — | 1 | — | — | — |
|  | 0.28 | — | — | — | 0 | — | — | — | 0 | 0 | 0 | 0 | — | 0 | — | — |
|  | 0.28 | — | 1 | 2 | — | — | — | — | — | — | — | — | 0 | — | — | — |
|  | 0.07 | — | — | — | 0 | — | — | — | 0 | 0 | 0 | 0 | — | 0 | — | — |
|  | 0.07 | — | 1 | 2 | — | — | — | — | — | — | — | — | — | — | — | — |
|  | 0.02 | — | — | — | 0 | — | — | — | 0 | 0 | 0 | 0 | — | 0 | — | — |
|  | 0.02 | — | 0 | 0 | — | — | — | — | — | — | — | — | 0 | — | — | — |
| 97 | 10.20 | — | — | — | 3 | — | — | — | 3 | 3 | 0 | 0 | — | 2 | — | — |
|  | 10.20 | — | 3 | 3 | — | — | — | — | — | — | — | — | 3 | — | — | — |
|  | 5.61 | — | — | — | 3 | — | — | — | 0 | 3 | 0 | 0 | — | 1 | — | — |
|  | 5.61 | — | 2 | 3 | — | — | — | — | — | — | — | — | 1 | — | — | — |
|  | 1.12 | — | — | — | 3 | — | — | — | 0 | 1 | 0 | 0 | — | 0 | — | — |
|  | 1.12 | — | 0 | 3 | — | — | — | — | — | — | — | — | 1 | — | — | — |
|  | 0.28 | — | — | — | 1 | — | — | — | 0 | 1 | 0 | 0 | — | 0 | — | — |

TABLE B-continued

Herbicide Secondary Preemergence
(C = 100% control)

| # | rate | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
|  | 0.28 | — | 0 | 1 | — | — | — | — | — | — | — | 0 | — | — | — |
|  | 0.07 | — | 0 | 0 | — | — | — | — | — | — | — | 0 | — | — | — |
|  | 0.07 | — | — | — | 0 | — | — | — | 0 | 0 | 0 | 0 | — | 0 | — | — |
|  | 0.02 | — | 0 | 0 | — | — | — | — | — | — | — | 0 | — | — | — |
|  | 0.02 | — | — | — | 0 | — | — | — | 0 | 0 | 0 | 0 | — | 0 | — | — |
| 98 | 10.20 | — | 3 | 3 | — | — | — | — | — | — | — | — | 3 | — | — | — |
|  | 10.20 | — | — | — | 3 | — | — | — | 3 | 3 | 0 | 3 | — | 3 | — | — |
|  | 5.61 | — | 3 | 3 | — | — | — | — | — | — | — | — | 3 | — | — | — |
|  | 5.61 | — | — | — | 3 | — | — | — | 3 | 3 | 1 | 3 | — | 3 | — | — |
|  | 1.12 | — | 3 | 3 | — | — | — | — | — | — | — | — | 3 | — | — | — |
|  | 1.12 | — | — | — | 3 | — | — | — | 3 | 3 | 0 | 1 | — | 3 | — | — |
|  | 0.28 | — | — | — | 3 | — | — | — | 3 | 3 | 0 | 0 | — | 3 | — | — |
|  | 0.28 | — | 3 | 3 | — | — | — | — | — | — | — | — | 3 | — | — | — |
|  | 0.07 | — | — | — | 3 | — | — | — | 3 | 3 | 0 | 0 | — | 3 | — | — |
|  | 0.07 | — | 3 | 3 | — | — | — | — | — | — | — | 3 | — | — | — | — |
|  | 0.02 | — | — | — | 3 | — | — | — | 0 | 3 | 0 | 0 | — | 1 | — | — |
|  | 0.02 | — | 1 | 3 | — | — | — | — | — | — | — | 2 | — | — | — |
| 99 | 10.20 | — | — | — | 3 | — | — | — | 3 | 3 | 1 | 1 | — | 3 | — | — |
|  | 10.20 | — | 3 | 3 | — | — | — | — | — | — | — | — | 3 | — | — | — |
|  | 5.61 | — | — | — | 3 | — | — | — | 3 | 3 | 2 | 1 | — | 3 | — | — |
|  | 5.61 | — | 3 | 3 | — | — | — | — | — | — | — | — | 3 | — | — | — |
|  | 1.12 | — | — | — | 3 | — | — | — | 3 | 3 | 0 | 0 | — | 3 | — | — |
|  | 1.12 | — | 3 | 3 | — | — | — | — | — | — | — | — | 3 | — | — | — |
|  | 0.28 | — | 3 | 3 | — | — | — | — | — | — | — | — | 3 | — | — | — |
|  | 0.28 | — | — | — | 3 | — | — | — | 3 | 3 | 0 | 0 | — | 3 | — | — |
|  | 0.07 | — | — | — | 3 | — | — | — | 1 | 3 | 0 | 0 | — | 2 | — | — |
|  | 0.07 | — | 3 | 3 | — | — | — | — | — | — | — | — | 3 | — | — | — |
|  | 0.02 | — | — | — | 3 | — | — | — | 0 | 3 | 0 | 0 | — | 0 | — | — |
|  | 0.02 | — | 2 | 3 | — | — | — | — | — | — | — | 3 | — | — | — |
| 100 | 5.61 | — | — | — | 3 | — | — | — | 3 | — | — | 2 | — | 3 | 3 | 3 |
|  | 5.61 | — | 3 | — | — | — | — | — | — | — | — | 3 | — | — | — |
|  | 1.12 | — | 3 | — | — | — | — | — | — | — | — | 2 | — | — | — |
|  | 1.12 | — | — | — | 3 | — | — | — | 3 | — | — | 1 | — | 3 | 3 | 3 |
|  | 0.28 | — | — | — | 1 | — | — | — | 3 | — | — | 1 | — | 1 | 0 | 1 |
|  | 0.28 | — | 0 | — | — | — | — | — | — | — | — | 1 | — | — | — |
|  | 0.07 | — | 0 | — | — | — | — | — | — | — | — | 0 | — | — | — |
|  | 0.07 | — | — | — | 0 | — | — | — | 0 | — | — | 0 | — | 0 | 1 | 0 |
| 101 | 1.12 | — | — | — | 3 | — | — | — | 3 | — | — | 3 | — | 3 | 3 | 3 |
|  | 1.12 | — | 3 | — | — | — | — | — | — | — | — | 3 | — | — | — |
|  | 0.28 | — | 3 | — | — | — | — | — | — | — | — | 3 | — | — | — |
|  | 0.28 | — | — | — | 3 | — | — | — | 3 | — | — | 3 | — | 3 | 3 | 3 |
|  | 0.07 | — | — | — | 3 | — | — | — | 3 | — | — | 2 | — | 3 | 3 | 1 |
|  | 0.07 | — | 3 | — | — | — | — | — | — | — | — | 3 | — | — | — |
|  | 0.02 | — | 3 | — | — | — | — | — | — | — | — | 3 | — | — | — |
|  | 0.02 | — | — | — | 3 | — | — | — | 3 | — | — | 1 | — | 3 | 3 | 3 |
|  | 0.00 | — | — | — | 3 | — | — | — | 3 | — | — | 0 | — | 2 | 1 | 3 |
|  | 0.00 | — | 3 | — | — | — | — | — | — | — | — | 3 | — | — | — |
| 102 | 1.12 | — | 3 | — | — | — | — | — | — | — | — | 3 | — | — | — |
|  | 1.12 | — | — | — | 3 | — | — | — | 3 | — | — | 2 | — | 3 | 3 | 3 |
|  | 0.28 | — | — | — | 3 | — | — | — | 3 | — | — | 2 | — | 3 | 3 | 3 |
|  | 0.28 | — | 3 | — | — | — | — | — | — | — | — | 3 | — | — | — |
|  | 0.07 | — | 3 | — | — | — | — | — | — | — | — | 3 | — | — | — |
|  | 0.07 | — | — | — | 3 | — | — | — | 3 | — | — | 2 | — | 3 | 3 | 3 |
|  | 0.02 | — | — | — | 3 | — | — | — | 3 | — | — | 1 | — | 3 | 2 | 3 |
|  | 0.02 | — | 3 | — | — | — | — | — | — | — | — | 3 | — | — | — |
|  | 0.00 | — | 3 | — | — | — | — | — | — | — | — | 3 | — | — | — |
|  | 0.00 | — | — | — | 3 | — | — | — | 3 | — | — | 1 | — | 3 | 0 | 1 |
| 103 | 1.12 | — | — | — | 3 | — | — | — | 3 | — | — | 3 | — | 3 | 3 | 3 |
|  | 1.12 | — | 3 | 3 | — | — | — | — | — | — | — | 3 | — | — | — |
|  | 0.28 | — | 3 | 3 | — | — | — | — | — | — | — | 3 | — | — | — |
|  | 0.28 | — | — | — | 3 | — | — | — | 3 | — | — | 3 | — | 3 | 3 | 3 |
|  | 0.07 | — | — | — | 3 | — | — | — | 3 | — | — | 3 | — | 3 | 3 | 3 |
|  | 0.07 | — | 3 | 3 | — | — | — | — | — | — | — | 3 | — | — | — |
|  | 0.02 | — | 2 | 3 | — | — | — | — | — | — | — | 3 | — | — | — |
|  | 0.02 | — | — | — | 3 | — | — | — | 3 | — | — | 2 | — | 2 | 3 | 3 |
|  | 0.00 | — | — | — | 2 | — | — | — | 1 | — | — | 1 | — | 0 | 2 | 3 |
|  | 0.00 | — | 0 | 0 | — | — | — | — | — | — | — | 0 | — | — | — |
|  | 0.00 | — | 0 | 0 | — | — | — | — | — | — | — | 0 | — | — | — |
|  | 0.00 | — | — | — | 0 | — | — | — | 0 | — | — | 1 | — | 0 | 1 | 1 |
| 104 | 5.61 | — | — | — | 3 | — | — | — | 3 | 3 | 1 | 0 | — | 3 | — | — |
|  | 5.61 | — | 3 | 3 | — | — | — | — | — | — | — | — | 3 | — | — | — |
|  | 1.12 | — | 3 | 3 | — | — | — | — | — | — | — | — | 3 | — | — | — |
|  | 1.12 | — | — | — | 3 | — | — | — | 0 | 3 | 0 | 0 | — | 2 | — | — |
|  | 0.28 | — | — | — | 3 | — | — | — | 0 | 2 | 0 | 0 | — | 0 | — | — |
|  | 0.28 | — | 0 | 3 | — | — | — | — | — | — | — | 2 | — | — | — |
|  | 0.07 | — | 0 | 0 | — | — | — | — | — | — | — | 0 | — | — | — |
|  | 0.07 | — | — | — | 1 | — | — | — | 0 | 0 | 0 | 0 | — | 0 | — | — |
|  | 0.02 | — | — | — | 0 | — | — | — | 0 | 0 | 0 | 0 | — | 0 | — | — |
|  | 0.02 | — | 0 | 0 | — | — | — | — | — | — | — | 0 | — | — | — |
| 105 | 11.21 | — | 3 | 3 | — | — | — | — | — | — | — | — | 3 | — | — | — |

TABLE B-continued

Herbicide Secondary Preemergence  
(C = 100% control)

| Ex. No. | Rate | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
|  | 11.21 | — | — | — | 3 | — | — | — | 3 | — | — | 1 | — | 2 | 3 | 3 |
|  | 5.61 | — | — | — | 3 | — | — | — | 3 | — | — | 1 | — | 3 | 3 | 3 |
|  | 5.61 | — | 3 | 3 | — | — | — | — | — | — | — | — | 3 | — | — | — |
|  | 1.12 | — | 0 | 1 | — | — | — | — | — | — | — | — | 0 | — | — | — |
|  | 1.12 | — | — | — | 3 | — | — | — | 0 | — | — | 0 | — | 0 | 1 | 1 |
|  | 0.28 | — | — | — | 0 | — | — | — | 3 | — | — | 0 | — | 0 | 2 | 3 |
|  | 0.28 | — | 0 | 0 | — | — | — | — | — | — | — | — | 0 | — | — | — |
| 106 | 1.12 | — | 3 | — | — | — | — | — | — | — | — | — | 3 | — | — | — |
|  | 1.12 | — | — | — | 3 | — | — | — | 3 | — | — | 3 | — | 3 | 3 | 3 |
|  | 0.28 | — | — | — | 3 | — | — | — | 3 | — | — | 2 | — | 3 | 3 | 3 |
|  | 0.28 | — | 3 | — | — | — | — | — | — | — | — | — | 3 | — | — | — |
|  | 0.07 | — | 3 | — | — | — | — | — | — | — | — | — | 3 | — | — | — |
|  | 0.07 | — | — | — | 3 | — | — | — | 3 | — | — | 2 | — | 3 | 3 | 3 |
|  | 0.02 | — | — | — | 3 | — | — | — | 3 | — | — | 1 | — | 2 | 2 | 3 |
|  | 0.02 | — | 3 | — | — | — | — | — | — | — | — | — | 3 | — | — | — |
|  | 0.00 | — | 0 | — | — | — | — | — | — | — | — | — | 1 | — | — | — |
|  | 0.00 | — | — | — | 3 | — | — | — | 3 | — | — | 0 | — | 1 | 0 | 3 |
| 107 | 1.12 | — | — | — | 3 | — | — | — | 3 | — | — | 3 | — | 3 | 3 | 3 |
|  | 1.12 | — | 3 | — | — | — | — | — | — | — | — | — | 3 | — | — | — |
|  | 0.28 | — | 3 | — | — | — | — | — | — | — | — | — | 3 | — | — | — |
|  | 0.28 | — | — | — | 3 | — | — | — | 3 | — | — | 3 | — | 3 | 3 | 3 |
|  | 0.07 | — | — | — | 3 | — | — | — | 3 | — | — | 2 | — | 3 | 3 | 3 |
|  | 0.07 | — | 3 | — | — | — | — | — | — | — | — | — | 3 | — | — | — |
|  | 0.02 | — | 3 | — | — | — | — | — | — | — | — | — | 3 | — | — | — |
|  | 0.02 | — | — | — | 3 | — | — | — | 3 | — | — | 1 | — | 2 | 3 | 3 |
|  | 0.00 | — | — | — | 3 | — | — | — | 2 | — | — | 1 | — | 0 | 0 | 3 |
|  | 0.00 | — | 1 | — | — | — | — | — | — | — | — | — | 2 | — | — | — |
| 108 | 11.21 | — | 0 | — | — | — | — | — | — | — | — | — | 0 | — | — | — |
|  | 11.21 | — | — | — | 0 | — | — | — | 1 | — | — | 0 | — | 1 | 0 | 1 |
|  | 5.61 | — | — | — | 0 | — | — | — | 1 | — | — | 0 | — | 0 | 0 | 0 |
|  | 5.61 | — | 0 | — | — | — | — | — | — | — | — | — | 0 | — | — | — |
|  | 1.12 | — | 0 | — | — | — | — | — | — | — | — | — | 0 | — | — | — |
|  | 1.12 | — | — | — | 0 | — | — | — | 1 | — | — | 0 | — | 0 | 0 | 0 |
| 109 | 5.61 | — | — | — | 3 | — | — | — | 3 | — | — | 3 | — | 3 | 3 | 3 |
|  | 5.61 | — | 3 | — | — | — | — | — | — | — | — | — | 3 | — | — | — |
|  | 1.12 | — | 3 | — | — | — | — | — | — | — | — | — | 3 | — | — | — |
|  | 1.12 | — | — | — | 3 | — | — | — | 3 | — | — | 2 | — | 3 | 3 | 3 |
|  | 0.28 | — | — | — | 3 | — | — | — | 3 | — | — | 2 | — | 3 | 3 | 3 |
|  | 0.28 | — | 3 | — | — | — | — | — | — | — | — | — | 3 | — | — | — |
|  | 0.07 | — | 3 | — | — | — | — | — | — | — | — | — | 1 | — | — | — |
|  | 0.07 | — | — | — | 3 | — | — | — | 3 | — | — | 1 | — | 2 | 3 | 3 |
|  | 0.02 | — | — | — | 3 | — | — | — | 2 | — | — | 0 | — | 0 | 0 | 2 |
|  | 0.02 | — | 0 | — | — | — | — | — | — | — | — | — | 1 | — | — | — |
|  | 0.00 | — | 0 | — | — | — | — | — | — | — | — | — | 0 | — | — | — |
|  | 0.00 | — | — | — | 0 | — | — | — | 0 | — | — | 0 | — | 0 | 0 | 0 |

POST-EMERGENT HERBICIDE ACTIVITY ON PLANTS

Although, as has been stated above, the compounds of this invention exhibit predominantly pre-emergence activity in greenhouse testing, nevertheless many of these compounds are active post-emergent herbicides. The post-emergent activity is best seen on younger plants treated at the 1½ to 2 leaf stage. In the tests which follow, larger and more developed plants were used.

The post-emergence herbicidal activity of compounds of this invention was demonstrated by greenhouse testing, and the results are shown in the following Table C. The post-emergent herbicidal activity data in Table C are based on the percent plant control of each tested plant species.

Top soil was placed in pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (two to three weeks), each pan (except the control pans) was moved to a spraying chamber and sprayed by means of an atomizer. The spray solution or suspension contained about 0.4% by volume of an emulsifying agent and a sufficient amount of the candidate chemical to give an application rate of the active ingredient of 11.2 kg/ha while applying a total amount of solution or suspension equivalent to 1870 L/ha. The pans were returned to the greenhouse and watered as before and the injury to the plants as compared to those in control pans was observed at approximately 10–14 days (usually 11 days).

TABLE C

Herbicide Primary Postemergence  
(C = 100% control)

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 1 | 11.2100 | 0 | — | — | 0 | 0 | 0 | 0 | 0 | — | — | — | 0 | 0 | 0 | 0 |
| 2 | 11.2100 | 0 | — | — | 0 | 1 | 1 | 0 | 0 | — | — | — | 0 | 0 | 0 | 0 |

TABLE C-continued

Herbicide Primary Postemergence
(C = 100% control)

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 3 | 11.2100 | 0 | — | — | 0 | 0 | 0 | 0 | 0 | — | — | — | 0 | 0 | 0 | N |
| 4 | 11.2100 | 0 | — | — | 0 | 0 | 0 | 0 | 0 | — | — | — | 0 | 0 | 0 | 0 |
| 5 | 11.2100 | 0 | — | — | 0 | 0 | 1 | 0 | 1 | — | — | — | 0 | 0 | 0 | 0 |
| 6 | 11.2100 | 0 | — | — | 0 | 0 | 0 | 0 | 0 | — | — | — | 0 | 0 | 0 | 0 |
| 7 | 11.2100 | 0 | — | — | 0 | 0 | 0 | 0 | 0 | — | — | 0 | 2 | 0 | 0 | 0 |
| 8 | 11.2100 | 0 | — | — | 0 | 0 | 0 | 0 | 0 | — | — | 0 | 0 | 0 | 0 | 0 |
| 9 | 11.2100 | 0 | — | — | 0 | 0 | 0 | 0 | 0 | — | — | 0 | 0 | 0 | 0 | 0 |
| 10 | 11.2100 | 0 | — | — | 0 | 1 | 0 | 0 | 0 | — | — | 0 | 0 | 0 | 0 | 0 |
| 11 | 11.2100 | 0 | — | — | 0 | 1 | 0 | 0 | 0 | — | — | 0 | 0 | 0 | 0 | 0 |
| 12 | 11.2100 | 0 | 0 | 0 | 0 | 1 | 1 | 0 | 1 | 1 | 2 | — | — | — | — | — |
| 13 | 11.2100 | 0 | 0 | 2 | 0 | 2 | 2 | 1 | 1 | 2 | 2 | — | — | — | — | — |
| 14 | 11.2100 | 0 | 0 | 2 | 0 | 2 | 2 | 0 | 2 | N | 2 | — | — | — | — | — |
| 15 | 11.2100 | 0 | 0 | 2 | 0 | 2 | 1 | 0 | 2 | N | 2 | — | — | — | — | — |
| 16 | 11.2100 | 0 | 0 | 2 | 0 | 0 | 0 | 0 | 0 | 0 | 0 | — | — | — | — | — |
| 17 | 11.2100 | 0 | 0 | 2 | 0 | 2 | 2 | 2 | 2 | 2 | 2 | — | — | — | — | — |
| 18 | 11.2100 | 0 | 0 | 2 | 0 | 1 | 0 | 2 | 0 | 2 | 2 | — | — | — | — | — |
| 19 | 11.2100 | 0 | 0 | 2 | 0 | 0 | 2 | 0 | 2 | 2 | 2 | — | — | — | — | — |
| 20 | 11.2100 | 0 | 0 | 0 | 0 | 1 | 1 | 1 | 2 | 2 | 1 | — | — | — | — | — |
| 21 | 11.2100 | 0 | 0 | 1 | 0 | 0 | 1 | 1 | 1 | 2 | 0 | — | — | — | — | — |
| 22 | 11.2100 | 0 | 0 | 1 | 0 | 0 | 0 | 0 | 1 | 1 | 0 | — | — | — | — | — |
| 23 | 11.2100 | 0 | 0 | 0 | 0 | 0 | 0 | 0 | 0 | 0 | 0 | — | — | — | — | — |
| 24 | 11.2100 | 0 | 0 | 2 | 0 | 0 | 0 | 0 | 0 | 0 | 0 | — | — | — | — | — |
| 25 | 11.2100 | 0 | 0 | 1 | 0 | 1 | 1 | 0 | 1 | 1 | 0 | — | — | — | — | — |
| 26 | 11.2100 | 0 | 0 | 0 | 0 | 0 | 1 | 0 | 1 | 1 | 1 | — | — | — | — | — |
| 27 | 11.2100 | 0 | 0 | 0 | 0 | 0 | 1 | 2 | 2 | 2 | 1 | — | — | — | — | — |
| 28 | 11.2100 | 0 | 0 | 1 | 0 | 0 | 0 | 0 | 0 | 0 | 0 | — | — | — | — | — |
| 29 | 11.2100 | 0 | 0 | 0 | 0 | 0 | 0 | 0 | 0 | 0 | 0 | — | — | — | — | — |
| 30 | 11.2100 | 0 | 0 | 0 | 0 | 0 | 0 | 0 | 0 | 0 | 0 | — | — | — | — | — |
| 31 | 11.2100 | 0 | 0 | 0 | 0 | 0 | 0 | 0 | 0 | 0 | 0 | — | — | — | — | — |
| 32 | 11.2100 | 0 | 1 | 2 | 0 | 1 | 1 | 0 | 1 | N | 2 | — | — | — | — | — |
| 33 | 11.2100 | 0 | 0 | 2 | 0 | 2 | 2 | 0 | 3 | 1 | 2 | — | — | — | — | — |
| 34 | 11.2100 | 0 | 0 | 2 | 0 | 0 | 2 | 1 | 1 | 1 | 2 | — | — | — | — | — |
| 35 | 11.2100 | 0 | 0 | 2 | 0 | 1 | 2 | 1 | 1 | 2 | 2 | — | — | — | — | — |
| 36 | 11.2100 | 1 | 0 | 2 | 0 | 2 | 1 | 1 | 1 | 2 | 2 | — | — | — | — | — |
| 37 | 11.2100 | 0 | 0 | 0 | 0 | 0 | 0 | 0 | 0 | 0 | 0 | — | — | — | — | — |
| 38 | 11.2100 | 0 | 0 | 0 | 0 | 0 | 0 | 0 | 0 | 0 | 0 | — | — | — | — | — |
| 39 | 11.2100 | 0 | 0 | 0 | 0 | 0 | 0 | 0 | 0 | 0 | 0 | — | — | — | — | — |
| 40 | 11.2100 | 0 | 0 | 0 | 0 | 0 | 0 | 1 | 0 | 0 | 0 | — | — | — | — | — |
| 41 | 11.2100 | 0 | 0 | 0 | 0 | 0 | 1 | 1 | 0 | 0 | 0 | — | — | — | — | — |
| 42 | 11.2100 | 0 | 0 | 0 | 0 | 0 | 0 | 0 | 0 | 0 | 0 | — | — | — | — | — |
| 43 | 11.2100 | 0 | 0 | 0 | 0 | 0 | 0 | 0 | 0 | 0 | 0 | — | — | — | — | — |
| 44 | 11.2100 | 0 | 0 | 0 | 0 | 0 | 0 | 0 | 0 | 1 | 0 | — | — | — | — | — |
| 45 | 11.2100 | 0 | 0 | 0 | 0 | 0 | 0 | 0 | 0 | 0 | 0 | — | — | — | — | — |
| 46 | 11.2100 | 0 | 0 | 0 | 0 | 0 | 0 | 0 | 0 | 0 | 0 | — | — | — | — | — |
| 47 | 11.2100 | 0 | 0 | 0 | 0 | 0 | 0 | 0 | 0 | 0 | 0 | — | — | — | — | — |
| 49 | 11.2100 | 0 | 0 | 0 | 0 | 0 | 0 | 0 | 0 | 0 | 0 | — | — | — | — | — |
| 50 | 11.2100 | 0 | 0 | 0 | 0 | 0 | 0 | 0 | 0 | 0 | 0 | — | — | — | — | — |
| 51 | 11.2100 | 0 | 0 | 0 | 0 | 0 | 0 | 0 | 0 | N | 0 | — | — | — | — | — |
| 52 | 11.2100 | 0 | 0 | 1 | 0 | 0 | 1 | 1 | 0 | 0 | 0 | — | — | — | — | — |
| 53 | 11.2100 | 0 | 0 | 70 | 0 | 30 | 50 | 60 | 60 | 50 | 70 | — | — | — | — | — |
| 54 | 11.2100 | 0 | 0 | 70 | 0 | 70 | 50 | 30 | 60 | 40 | 70 | — | — | — | — | — |
| 55 | 11.2100 | 0 | 0 | 0 | 0 | 0 | 0 | 0 | 0 | 0 | 0 | — | — | — | — | — |
| 56 | 11.2100 | 0 | 0 | 20 | 0 | 20 | 30 | 30 | 10 | 0 | 20 | — | — | — | — | — |
| 57 | 11.2100 | 0 | 0 | 20 | 0 | 10 | 10 | 10 | 10 | 10 | 20 | — | — | — | — | — |
| 58 | 11.2100 | 0 | 0 | 10 | 0 | 0 | 0 | 0 | 0 | 10 | 0 | — | — | — | — | — |
| 59 | 11.2100 | 0 | 0 | 0 | 0 | 0 | 10 | 10 | 0 | 10 | 10 | — | — | — | — | — |
| 60 | 11.2100 | 0 | 0 | 0 | 0 | 0 | 20 | 20 | 10 | 30 | 30 | — | — | — | — | — |
| 61 | 11.2100 | 0 | 0 | 0 | 0 | 20 | 0 | 10 | 0 | 10 | 10 | — | — | — | — | — |
| 62 | 11.2100 | 0 | 0 | 20 | 20 | 20 | 30 | 20 | 50 | N | N | — | — | — | — | — |
| 63 | 11.2100 | 0 | 30 | 50 | 20 | 50 | 50 | 30 | 60 | N | N | — | — | — | — | — |
| 64 | 11.2100 | 0 | 60 | 60 | 20 | 60 | 80 | 40 | 50 | 50 | 60 | — | — | — | — | — |
| 65 | 11.2100 | 0 | 40 | 60 | 0 | 80 | 40 | 50 | 40 | 50 | 60 | — | — | — | — | — |
| 66 | 11.2100 | 0 | 10 | 40 | 20 | 60 | 40 | 50 | 60 | 60 | 50 | — | — | — | — | — |
| 67 | 11.2100 | 0 | 20 | 0 | 0 | 10 | 50 | 40 | 40 | 50 | 50 | — | — | — | — | — |
| 68 | 11.2100 | 0 | 0 | 20 | 0 | 0 | 30 | 40 | 20 | 20 | 30 | — | — | — | — | — |
| 69 | 11.2100 | 0 | 20 | 40 | 0 | 50 | 30 | 40 | 30 | 20 | 40 | — | — | — | — | — |
| 70 | 11.2100 | 0 | 0 | 10 | 0 | 0 | 30 | 20 | 0 | 10 | 10 | — | — | — | — | — |
| 71 | 11.2100 | 0 | 0 | 20 | 0 | 20 | 50 | 50 | 30 | 20 | 50 | — | — | — | — | — |
| 72 | 11.2100 | 0 | 0 | 10 | 0 | 10 | 10 | 20 | 10 | 20 | 30 | — | — | — | — | — |
| 73 | 11.2100 | 0 | 0 | 0 | 0 | 0 | 20 | 30 | 20 | 30 | 30 | — | — | — | — | — |
| 74 | 11.2100 | 0 | 20 | 50 | 10 | 30 | 40 | 30 | 30 | 40 | 40 | — | — | — | — | — |
| 75 | 11.2100 | 0 | 0 | 30 | 0 | 30 | 30 | 30 | 30 | N | 30 | — | — | — | — | — |
| 76 | 11.2100 | 0 | 0 | 30 | 0 | 0 | 30 | 30 | 30 | 20 | 30 | — | — | — | — | — |
| 77 | 11.2100 | 0 | 20 | 30 | 0 | 30 | 20 | 30 | 20 | 20 | 40 | — | — | — | — | — |
| 78 | 11.2100 | 0 | 10 | 0 | 0 | 10 | 30 | 30 | 30 | 20 | 30 | — | — | — | — | — |
| 79 | 11.2100 | 0 | 20 | 0 | 0 | 0 | 20 | 30 | 10 | 10 | 30 | — | — | — | — | — |
| 80 | 11.2100 | 0 | 10 | 30 | 0 | 0 | 10 | 30 | 0 | 0 | 0 | — | — | — | — | — |
| 81 | 11.2100 | 0 | 0 | 30 | 0 | 30 | 10 | 30 | 0 | 30 | 10 | — | — | — | — | — |

TABLE C-continued

Herbicide Primary Postemergence
(C = 100% control)

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 82 | 11.2100 | 0 | 10 | 30 | 0 | 20 | 10 | 30 | 0 | 20 | 0 | — | — | — | — | — |
| 83 | 11.2100 | 0 | 0 | 0 | 0 | 0 | 30 | 10 | 20 | 20 | 10 | — | — | — | — | — |
| 84 | 11.2100 | 0 | 0 | 0 | 0 | 0 | 20 | 20 | 0 | 30 | 0 | — | — | — | — | — |
| 85 | 11.2100 | 0 | 0 | 0 | 0 | 0 | 10 | 0 | 0 | 0 | 0 | — | — | — | — | — |
| 86 | 11.2100 | 0 | 10 | 20 | 0 | 20 | 40 | 20 | 0 | 20 | 10 | — | — | — | — | — |
| 87 | 11.2100 | 0 | 20 | 40 | 20 | 10 | 60 | 40 | 50 | 50 | 40 | — | — | — | — | — |
| 88 | 11.2100 | 40 | 90 | 90 | 10 | 90 | 30 | 40 | 70 | 90 | 50 | — | — | — | — | — |
|  | 11.2100 | 40 | 30 | 60 | 10 | 60 | 50 | 30 | 80 | 60 | 60 | — | — | — | — | — |
| 89 | 11.2100 | 0 | 20 | 60 | 0 | 60 | 0 | 20 | 30 | 80 | 0 | — | — | — | — | — |
|  | 11.2100 | 0 | 0 | 50 | 10 | 20 | 20 | 60 | 20 | 80 | 20 | — | — | — | — | — |
| 90 | 11.2100 | 0 | 0 | 10 | 0 | 0 | 30 | 30 | 10 | 30 | N | — | — | — | — | — |
| 91 | 11.2100 | 0 | 0 | 40 | 0 | 10 | 50 | 40 | 40 | 60 | 60 | — | — | — | — | — |
| 92 | 11.2100 | 0 | 0 | 60 | 10 | 30 | 60 | 40 | 40 | 60 | 50 | — | — | — | — | — |
| 93 | 11.2100 | 0 | 0 | 0 | 0 | 0 | 0 | 0 | 0 | 10 | 0 | — | — | — | — | — |
| 94 | 11.2100 | 0 | 50 | N | N | 10 | 50 | N | 40 | N | N | — | — | — | — | — |
|  | 11.2100 | 0 | 0 | 60 | 0 | 0 | 50 | 30 | 30 | 20 | 40 | — | — | — | — | — |
| 95 | 11.2100 | 0 | 20 | 50 | 20 | 40 | 40 | 30 | 0 | 40 | 30 | — | — | — | — | — |
| 96 | 11.2100 | 0 | 0 | 30 | 10 | 0 | 50 | 40 | 0 | 30 | 0 | — | — | — | — | — |
| 97 | 11.2100 | 0 | 0 | 50 | 20 | 10 | 40 | 50 | 0 | 20 | 10 | — | — | — | — | — |
| 98 | 11.2100 | 0 | 0 | 70 | 20 | 60 | 60 | 50 | 20 | 50 | 30 | — | — | — | — | — |
| 99 | 11.2100 | 0 | 20 | 50 | 20 | 50 | 50 | 40 | 10 | 30 | 10 | — | — | — | — | — |
| 100 | 11.2100 | 0 | 0 | 0 | 0 | 0 | 0 | 20 | 0 | 20 | 10 | — | — | — | — | — |
| 101 | 11.2100 | 10 | 0 | 10 | 0 | 30 | 10 | 20 | 10 | 20 | 30 | — | — | — | — | — |
| 102 | 11.2100 | 0 | 0 | 20 | 0 | 30 | 20 | 30 | 10 | 30 | 20 | — | — | — | — | — |
| 103 | 11.2100 | 30 | 10 | 50 | 0 | 50 | 40 | 50 | 30 | 20 | 40 | — | — | — | — | — |
| 104 | 11.2100 | 0 | 30 | 50 | 0 | 20 | 30 | 30 | 20 | 40 | 30 | — | — | — | — | — |
| 105 | 11.2100 | 0 | 0 | 0 | 0 | 0 | 0 | 10 | 0 | 0 | 0 | — | — | — | — | — |
| 106 | 11.2100 | 0 | 0 | 0 | 0 | 0 | 10 | 20 | 10 | 30 | 30 | — | — | — | — | — |
| 107 | 11.2100 | 0 | 0 | 0 | 0 | 10 | 10 | 30 | 10 | 20 | 20 | — | — | — | — | — |
| 108 | 11.2100 | 0 | 0 | 0 | 0 | 0 | 0 | 0 | 0 | 0 | 0 | — | — | — | — | — |
| 109 | 11.2100 | 0 | 0 | 0 | 0 | 0 | 10 | 20 | 10 | 20 | 20 | — | — | — | — | — |
| 110 | 11.2100 | 0 | 0 | 0 | 0 | 0 | 0 | 20 | 10 | 0 | 0 | — | — | — | — | — |

Compounds of this invention were also tested for herbicidal activity on weed plants in the presence of certain crop plants according to the following procedure:

Topsoil (silt loam) is sieved through a screen having 1.27 cm openings. In some of the tests the soil was mixed with fertilizer (1225 g/cu. m of 12/5/9 containing isobutylidene diurea), while in other tests the fertilizer was omitted. This mixture is steam sterilized and then placed in aluminum pans 6.985 cm deep having ten holes in the bottom each 0.635 cm in diameter. The soil mixture is compacted to a depth of 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with 1.27 cm of a mixture of 50% topsoil and 50% of a mixture of Canadian sphagnum peat moss, vermiculite and a wetting agent. The pans are then placed on a capillary mat on a greenhouse bench and subirrigated as needed. After the plants reach the desired stage (9 to 14 days, 1 to 3 true leaf stage), each pan (except the control pans) is removed to a spraying chamber and sprayed by means of an atomizer, operating at a spray pressure of 170.3 kPa (10 psig) at the application rates noted in Table D. In the spray solution is an amount of an emulsifying agent mixture (35% butylamine salt of dodecylbenzenesulfonic acid and 65% tall oil condensed with ethylene oxide in the ratio of 11 mols of ethylene oxide/mol of tall oil) to give a spray solution or suspension. The spray solution or suspension contains a sufficient amount of the candidate chemical in order to give application rates of the active ingredient corresponding to those shown in Table D below while applying a total amount of solution or suspension equivalent to 1870 L/Ha (200 gallons/acre). The pans are returned to the greenhouse and watered as before and the injury to the plants as compared to the control pans is observed at approximately 10-14 days (usually 11 days).

In the following Table D the legends used to identify the plant species are the same as those above.

TABLE D

Herbicide Secondary Postemergence

| Ex. No. | Rate kg/ha | Sobe | Cotz | Rape | Cobu | Wihw | Mogl | Hese | Jiwe | Vele | Whez | Rice | Grso | Corn | Dobr | Prmi | Bygr | Lacg | Grft | Cocw | Anbg | Barz | Ruth | Seig | Wina |
|---|---|---|---|---|---|---|---|---|---|---|---|---|---|---|---|---|---|---|---|---|---|---|---|---|---|
| 14 | 5.6050 | 3 | 1 | 3 | 2 | 2 | 3 | 3 | 2 | 2 | 0 | 0 | 2 | 3 | 0 | 2 | 2 | 3 | 2 | — | — | — | — | — | — |
|  | 1.1210 | 1 | 0 | 0 | 0 | 0 | 0 | 3 | 2 | 2 | 0 | 0 | 2 | 3 | 0 | 0 | 2 | 3 | 2 | — | — | — | — | — | — |
|  | 0.2803 | 0 | 0 | 0 | 0 | 0 | 2 | 2 | 0 | 2 | 0 | 0 | 2 | 2 | 0 | 0 | 2 | 3 | 2 | — | — | — | — | — | — |
|  | 0.0701 | 0 | 0 | 0 | 0 | 0 | 0 | 0 | 0 | 2 | 0 | 0 | 2 | 2 | 0 | 0 | 2 | 3 | 2 | — | — | — | — | — | — |
| 17 | 5.6050 | 3 | 2 | 0 | 2 | 2 | 2 | 3 | 2 | 2 | 0 | 0 | 2 | 3 | 0 | 0 | 2 | 3 | 2 | — | — | — | — | — | — |
|  | 1.1210 | 1 | 0 | 1 | 0 | 0 | 0 | 2 | 1 | 2 | 0 | 0 | 2 | 3 | 0 | 0 | 2 | 3 | 2 | — | — | — | — | — | — |
|  | 0.2803 | 0 | 0 | 2 | 0 | 2 | 2 | 2 | 0 | 2 | 0 | 0 | 2 | 2 | 0 | 0 | 2 | 2 | 0 | — | — | — | — | — | — |
|  | 0.0701 | 0 | 0 | 0 | 0 | 0 | 0 | 2 | 0 | 2 | 0 | 0 | 2 | 0 | 0 | 0 | 2 | 2 | 0 | — | — | — | — | — | — |
| 33 | 11.2100 | 2 | 2 | 3 | 2 | 2 | 2 | 2 | — | 2 | 0 | 0 | 2 | 2 | 0 | 0 | 2 | 3 | 2 | — | — | — | — | — | — |
|  | 5.6050 | 2 | 2 | 2 | 2 | 0 | 2 | 2 | — | 2 | 0 | 0 | 2 | 2 | 0 | 0 | 2 | 3 | 2 | — | — | — | — | — | — |
|  | 1.1210 | 2 | 1 | 2 | 2 | 0 | 1 | 2 | — | 2 | 0 | 0 | 2 | 2 | 0 | 0 | 1 | 2 | 0 | — | — | — | — | — | — |
|  | 0.2803 | 2 | 1 | 2 | 2 | 0 | 1 | 1 | — | 1 | 0 | 0 | 0 | 1 | 0 | 0 | 0 | 0 | 0 | — | — | — | — | — | — |
| 34 | 11.2100 | 1 | 1 | 1 | 1 | 0 | 1 | 0 | — | 0 | 0 | 0 | 0 | 0 | 0 | 0 | 0 | 0 | 0 | — | — | — | — | — | — |
|  | 5.6050 | 1 | 0 | 2 | 0 | 0 | 0 | 3 | — | 3 | 0 | 0 | 0 | 0 | 0 | 0 | 0 | 0 | 0 | — | — | — | — | — | — |
|  | 1.1210 | 0 | 0 | 1 | 0 | 0 | 0 | 0 | — | 2 | 0 | 0 | 0 | 0 | 0 | 0 | 0 | 0 | 0 | — | — | — | — | — | — |
|  | 0.2803 | 3 | 0 | 3 | 3 | 2 | 3 | 3 | — | 3 | 0 | 0 | 0 | 0 | 0 | 0 | 0 | 0 | 0 | — | — | — | — | — | — |
| 36 | 5.6050 | 3 | 1 | 3 | 2 | 2 | 2 | 3 | — | 2 | 0 | 0 | 0 | 0 | 0 | 0 | 0 | 2 | 2 | — | — | — | — | — | — |
|  | 1.1210 | 1 | 0 | 1 | 1 | 0 | 0 | 3 | — | 3 | 0 | 0 | 0 | 0 | 0 | 0 | 0 | 2 | 0 | — | — | — | — | — | — |
|  | 0.2803 | 0 | 0 | 0 | 0 | 0 | 0 | 3 | — | 3 | 0 | 0 | 0 | 0 | 0 | 0 | 0 | 2 | 0 | — | — | — | — | — | — |
| 55 | 5.6050 | 75 | 60 | 85 | 75 | 0 | 75 | 90 | 80 | 85 | 10 | 30 | 50 | 50 | 20 | 30 | 50 | 85 | 40 | 75 | 20 | 40 | 20 | 60 | 10 |
|  | 1.1210 | 70 | 40 | 85 | 70 | 60 | 60 | 80 | 75 | 75 | 5 | 5 | 0 | 50 | 5 | 0 | 0 | 75 | 50 | 65 | 0 | 25 | 15 | 0 | 0 |
|  | 0.2803 | 50 | 30 | 50 | 20 | 25 | 20 | 70 | 65 | 50 | 0 | 10 | 30 | 70 | 5 | 0 | 25 | 70 | 25 | 60 | 0 | 0 | 0 | 0 | 0 |
|  | 0.0701 | 20 | 20 | 40 | 20 | 25 | 65 | 30 | 65 | 20 | 0 | 0 | 30 | 30 | 0 | 0 | 0 | 75 | 35 | 35 | 0 | 0 | 0 | 0 | 0 |
| 56 | 5.6050 | 70 | 50 | 85 | 65 | 60 | 65 | 60 | — | 50 | 10 | 30 | 30 | 65 | 5 | 0 | 40 | 50 | 0 | 60 | 0 | 0 | 0 | 0 | 0 |
|  | 1.1210 | 60 | 35 | 80 | 60 | 40 | 60 | 50 | — | 70 | 5 | 5 | 25 | 40 | 0 | 0 | 30 | 40 | 0 | 30 | 0 | 0 | 0 | 0 | 0 |
|  | 0.2803 | 65 | 25 | 75 | 60 | 25 | 60 | 80 | — | 75 | 10 | 10 | 25 | 30 | 0 | 20 | 10 | 35 | 25 | 60 | 0 | 0 | 0 | 0 | 0 |
|  | 0.0701 | 50 | 10 | 80 | 35 | 25 | 50 | 60 | — | 35 | 5 | 0 | 5 | 10 | 0 | 0 | 75 | 30 | 0 | 20 | 0 | 0 | 0 | 0 | 0 |
| 64 | 5.6050 | 60 | 35 | 80 | 60 | 30 | 60 | 80 | — | 80 | 0 | 0 | 35 | 65 | 0 | 0 | 40 | 70 | 0 | 60 | 0 | 0 | 0 | 0 | 0 |
|  | 1.1210 | 50 | 20 | 75 | 50 | 25 | 50 | 60 | — | 40 | 0 | 0 | 30 | 40 | 20 | 0 | 30 | 90 | 40 | 20 | 0 | 0 | 0 | 0 | 0 |
| 65 | 11.2100 | 80 | 60 | 80 | 80 | 40 | 70 | 80 | — | 80 | 10 | 15 | N | 80 | 0 | 20 | 10 | 80 | 10 | 80 | 0 | 0 | 0 | 0 | 0 |
|  | 5.6050 | 80 | 70 | 80 | 75 | 25 | 75 | 75 | — | 60 | 0 | 0 | 30 | 20 | 20 | 0 | 75 | 80 | 50 | 70 | 0 | 0 | 0 | 0 | 0 |
|  | 1.1210 | 75 | 65 | 80 | 75 | 25 | 40 | 50 | — | 50 | 0 | 0 | 35 | 35 | 0 | 0 | 35 | 80 | 10 | 30 | 0 | 0 | 0 | 0 | 0 |
|  | 0.2803 | 50 | 50 | 80 | 60 | 0 | 80 | 80 | — | 75 | 10 | 5 | 25 | 20 | 0 | 0 | 5 | 80 | 5 | 0 | 0 | 0 | 0 | 0 | 0 |
| 66 | 5.6050 | 80 | 50 | 80 | 80 | 40 | 80 | 80 | — | 70 | 0 | 0 | 0 | 35 | 0 | 0 | 5 | 70 | 0 | 20 | 0 | 0 | 0 | 0 | 0 |
|  | 1.1210 | 65 | 50 | 75 | 40 | 25 | 70 | 80 | — | 40 | 0 | 5 | 25 | 50 | 0 | 0 | 0 | 80 | 0 | 10 | 0 | 0 | 0 | 0 | 0 |
|  | 0.2803 | 20 | 25 | 70 | 75 | 25 | 70 | 70 | — | 40 | 0 | 0 | 35 | 20 | 0 | 0 | 0 | 0 | 0 | 0 | 0 | 0 | 0 | 0 | 0 |
|  | 0.0701 | 40 | 10 | 25 | 25 | — | 60 | — | — | — | — | 5 | 25 | 25 | — | — | 50 | 80 | — | 15 | 20 | 40 | 20 | 60 | 10 |
| 88 | 5.6050 | — | — | — | — | 50 | — | — | — | — | 15 | — | — | 50 | 20 | — | — | — | — | 60 | 0 | 0 | 0 | 0 | 0 |
|  | 1.1210 | 5 | — | 55 | — | 45 | — | — | — | 30 | 0 | 5 | — | 5 | 10 | — | — | 30 | — | 55 | 0 | 10 | 15 | 5 | 0 |
|  | 0.2803 | 0 | 50 | 30 | 30 | 30 | 60 | — | — | 0 | 0 | 0 | 0 | 0 | 0 | — | 0 | 0 | 0 | 15 | 0 | 0 | 0 | 0 | 0 |
|  | 0.2803 | 0 | 25 | 20 | 10 | 10 | 30 | — | — | 0 | 0 | 0 | 0 | 50 | 0 | — | 0 | 0 | 0 | 10 | 0 | 10 | 0 | 0 | 0 |
|  | 0.0701 | 0 | 25 | 20 | 10 | 10 | 20 | — | — | 0 | 0 | 0 | 0 | 5 | 0 | — | 0 | 0 | 0 | 10 | 0 | 0 | 0 | 0 | 0 |
|  | 0.0701 | 5 | 35 | 25 | 40 | 50 | 50 | — | — | 25 | 10 | 0 | 0 | 50 | 15 | — | 0 | 5 | 15 | 15 | 0 | 10 | 15 | 5 | 0 |
| 89 | 11.2100 | 0 | 25 | 25 | 35 | 35 | 50 | — | — | 0 | 0 | 20 | 0 | 70 | 0 | — | 0 | 0 | 20 | 20 | 0 | 0 | 0 | 0 | 0 |
|  | 5.6050 | 0 | 25 | 10 | — | 20 | — | — | — | — | — | — | — | — | — | — | — | — | — | — | — | — | — | — | — |
|  | 1.1210 | — | — | — | — | — | — | — | — | — | — | — | — | — | — | — | — | — | — | — | — | — | — | — | — |

TABLE D-continued

Herbicide Secondary Postemergence

| Ex. No. | Rate kg/ha | Sobe | Cotz | Rape | Cobu | Wibw | Mogl | Hese | Jiwe | Vele | Whez | Rice | Girso | Corn | Dobr | Prmi | Bygr | Lacg | Girft | Coew | Anhg | Barz | Ruth | Sejg | Wioa |
|---|---|---|---|---|---|---|---|---|---|---|---|---|---|---|---|---|---|---|---|---|---|---|---|---|---|
| | 1.1210 | 0 | 30 | 0 | 20 | — | 40 | — | — | 0 | — | 0 | 30 | 0 | — | — | 0 | 0 | 0 | — | — | — | 0 | 0 | — |
| | 0.2803 | — | — | — | — | 10 | — | — | — | — | — | — | — | — | — | — | — | — | — | 0 | — | — | — | — | 0 |
| | 0.2803 | 0 | 20 | 20 | 5 | — | 5 | — | — | 0 | — | 0 | 5 | 0 | — | — | 0 | 0 | 20 | 35 | 0 | 0 | 40 | 0 | 0 |
| 92 | 5.6050 | 50 | 50 | 70 | 70 | 70 | 75 | — | — | 80 | — | 0 | 25 | 0 | — | — | 0 | 90 | 20 | 40 | 0 | 0 | N | 0 | 0 |
| | 1.1210 | 20 | 60 | 60 | 70 | 60 | 80 | — | — | 80 | — | 0 | 25 | 0 | — | — | 0 | 80 | 10 | 20 | 0 | 0 | 10 | 0 | 0 |
| | 0.2803 | 35 | 25 | 50 | 60 | 20 | 60 | — | — | 75 | — | 20 | 0 | 0 | — | — | 0 | 90 | 0 | 0 | 0 | 0 | 0 | 0 | 0 |
| | 0.0701 | — | — | 25 | — | 0 | — | — | — | — | — | — | — | — | — | — | — | — | — | — | — | — | — | — | — |
| | 0.0701 | 10 | 25 | — | 35 | — | 30 | — | — | 50 | — | 10 | 10 | 0 | — | — | 0 | 80 | 0 | 0 | — | — | — | 10 | — |

As can be seen from the data above, some of the compounds appear to be quite safe on certain crops and can thus be used for selective control of weeds in these crops.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1–15 parts) of wetting agent, from about 0.25 to 25 parts (preferably 10–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include N,-N-dimethylformamide, dimethylsulfoxide, N-methyl-pyrrolidone, hydrocarbons, and water-immiscible ethers, esters, or ketones. However, other high strength liquid Concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising at least one active ingredient adhered to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like, such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-d:α',1'-c)-pyrazidiinium salt
5-Bromo-3-isopropyl-6-methyluracil 1,1'-dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate Ureas N-(4-chlorophenoxy) phenyl-N,N-dimethylurea
N,N-dimethyl-N'-(3-chloro-4-methylphenyl) urea
3-(3,4-Dichlorophenyl)-1,1-dimethylurea 1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl)
 aminocarbonyl]-benzenesulfonamide
Methyl 2-(((((4,6-dimethyl-2-pyrimidinyl)amino)carbonyl)amino)sulfonyl) benzoate
Ethyl 2-[methyl 2-(((((4,6-dimethyl-2-pyrimidinyl)amino)carbonyl)amino)sulfonyl)]benzoate
Methyl-2((4,6-dimethoxy pyrimidin-2-yl)aminocarbonyl)amino sulfonyl methyl) benzoate
Methyl 2-(((((4-methoxy-6-methyl-1,3,5-triazin-2-yl)amino)carbonyl)amino)sulfonyl) benzoate Carbamates/Thiolcarbamates 2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate Acetamides/Acetanilides/Anilines/Amides 2-Chloro-N,N-diallylacetamide
N,N-dimethyl-2,2-diphenylacetamide
N-(2,4-dimethyl-5-[[(trifluoromethyl)sulfonyl] amino]-phenyl]acetamide N-Isopropyl-2-chloroacetanilide
2,6'-Diethyl-N-methoxymethyl-2-chloroacetanilide
2'-Methyl-6'-ethyl-N-(2-methoxypropyl-2-yl)-2-chloroacetanilide
α,α,α-Trifluoro-2,6-dinitro-N,N-dipropyl-p-toluidine
N-(1,1-dimethylpropynyl)-3,5-dichlorobenzamide Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol N-(phosphonomethyl) glycine and its salts.
Butyl 2-[4-[(5-(trifluoromethyl)-2-pyridinyl)oxy]-phenoxy]propanoate Ethers 2,4-Dichlorophenyl-4-nitrophenyl ether
2-Chloro-α,α,α-trifluoro-p-tolyl-3-ethoxy-4-nitrodiphenyl ether
5-(2-chloro-4-trifluoromethylphenoxy)-N-methyl sulfonyl
2-nitrobenzamide
1'-(Carboethoxy) ethyl 5-[2-chloro-4-(trifluoro methyl)-phenoxy]-2-nitrobenzoate Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo (2.2.1) heptane, 1-methyl-4-(1-methyl ethyl)-2-(2-methylphenylmethoxy)-,exo- Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| I. Emulsifiable Concentrates | | Weight Percent |
|---|---|---|
| A. | Compound of Example No. 1 | 11.0 |
| | Free acid of complex organic phosphate or aromatic or aliphatic hydrophobe base (e.g., GAFAC RE-610, registered trademark of GAF Corp.) | 5.59 |
| | Polyoxyethylene/polyoxypropylene block copolymer with butanol (e.g., Tergitol XH, registered trademark of Union Carbide Corp.) | 1.11 |
| | Phenol | 5.34 |
| | Monochlorobenzene | 76.96 |
| | | 100.00 |
| B. | Compound of Example No. 10 | 25.00 |
| | Free acid of complex organic phosphate of aromatic or aliphatic hydrophobe base (e.g., GAFAC RE-610) | 5.00 |
| | Polyoxyethylene/polyoxypropylene block copolymer with butanol (e.g., Tergitol XH) | 1.60 |
| | Phenol | 4.75 |
| | Monochlorobenzene | 63.65 |
| | | 100.00 |

| II. Flowables | | Weight Percent |
|---|---|---|
| A. | Compound of Example No. 19 | 25.00 |
| | Methyl cellulose | 0.3 |
| | Silica Aerogel | 1.5 |
| | Sodium lignosulfonate | 3.5 |
| | Sodium N-methyl-N-oleyl taurate | 2.0 |
| | Water | 67.7 |
| | | 100.00 |
| B. | Compound of Example No. 12 | 45.0 |
| | Methyl cellulose | .3 |
| | Silica aerogel | 1.5 |
| | Sodium lignosulfonate | 3.5 |
| | Sodium N-methyl-N-oleyl taurate | 2.0 |
| | Water | 47.7 |
| | | 100.00 |

| III. Wettable Powders | | Weight Percent |
|---|---|---|
| A. | Compound of Example No. 2 | 25.0 |
| | Sodium lignosulfonate | 3.0 |
| | Sodium N-methyl-N-oleyl-taurate | 1.0 |
| | Amorphous silica (synthetic) | 71.0 |
| | | 100.00 |
| B. | Compound of Example 16 | 80.00 |
| | Sodium dioctyl sulfosuccinate | 1.25 |
| | Calcium lignosulfonate | 2.75 |
| | Amorphous silica (synthetic) | 16.00 |
| | | 100.00 |
| C. | Compound of Example No. 3 | 10.0 |
| | Sodium lignosulfonate | 3.0 |
| | Sodium N-methyl-N-oleyl-taurate | 1.0 |
| | Kaolinite clay | 86.0 |
| | | 100.00 |

| IV. Dusts | | Weight Percent |
|---|---|---|
| A. | Compound of Example No. 8 | 2.0 |
| | Attapulgite | 98.0 |
| | | 100.00 |
| B. | Compound of Example No. 5 | 60.0 |
| | Montmorillonite | 40.0 |
| | | 100.00 |
| C. | Compound of Example No. 5 | 30.0 |
| | Ethylene glycol | 1.0 |
| | Bentonite | 69.0 |
| | | 100.00 |
| D. | Compound of Example No. 11 | 1.0 |
| | Diatomaceous earth | 99.0 |
| | | 100.00 |

| V. Granules | | Weight Percent |
|---|---|---|
| A. | Compound of Example No. 10 | 15.0 |
| | Granular attapulgite (20/40 mesh) | 85.0 |
| | | 100.00 |
| B. | Compound of Example No. 4 | 30.0 |
| | Diatomaceous earth (20/40) | 70.0 |
| | | 100.00 |
| C. | Compound of Example No. 8 | 1.0 |
| | Ethylene glycol | 5.0 |
| | Methylene blue | 0.1 |
| | Pyrophyllite | 93.9 |
| | | 100.00 |
| D. | Compound of Example No. 6 | 5.0 |
| | Pyrophyllite (20/40) | 95.0 |
| | | 100.00 |

When operating in accordance with the present invention, effective amounts of the compounds of this invention are applied to the soil containing the seeds, or vegetative propagules or may be incorporated into soil media i any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1961). Thus, the term refers to any substance or medium in which vegetation may take root and grow, and includes not only earth but also compost, manure, muck, humus, sand, and the like, adapted to support plant growth.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skills in the art to which the invention pertains.

What is claimed is:

1. A compound represented by the formula

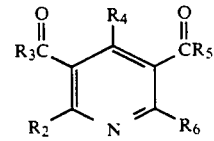

wherein:
$R_2$ and $R_6$ are independently lower alkyl, fluorinated methyl, chlorofluorinated methyl, or chlorinated methyl, provided that one of $R_2$ and $R_6$ is fluorinated methyl or chlorofluorinated methyl;

$R_3$ is alkoxy or alkylthio;

$R_4$ is hydrogen, alkyl, cycloalkyl, or cycloalkylalkyl; and $R_5$ is thiazolyl or 4,5-(dihydro)thiazolyl, each optionally substituted with one or more radicals selected from halo, amino, aminocarbonyl, cyano, alkoxy, alkyl, alkoxyalkyl, alkoxycarbonyl, alkylamino, and dialkylamino.

2. The compound of claim 1 wherein $R_4$ is 2-methylpropyl.

3. The compound of claim 2 wherein one of $R_2$ and $R_6$ is trifluoromethyl and the other is difluoromethyl.

4. The compound of claim 3 wherein $R_3$ is methoxy.

5. The compound of claim 4 wherein $R_5$ is 2-thiazolyl.

6. A method of controlling undesirable vegetation comprising applying thereto an effective amount of a compound represented by the formula

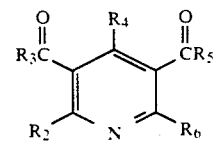

wherein:
$R_2$ and $R_6$ are independently lower alkyl, fluorinated methyl, chlorofluorinated methyl, or chlorinated methyl, provided that one of $R_2$ and $R_6$ is fluorinated methyl or chlorofluorinated methyl;

$R_3$ is alkoxy or alkylthio;

$R_4$ is hydrogen, alkyl, cycloalkyl, or cycloalkylalkyl; and $R_5$ is thiazolyl or 4,5-(dihydro)thiazolyl, each optionally substituted with one or more radicals selected from halo, amino, aminocarbonyl, cyano, alkoxy, alkyl, alkoxyalkyl, alkoxycarbonyl, alkylamino, and dialkylamino.

7. The method of claim 6 wherein $R_4$ is 2-methylpropyl.

8. The method of claim 7 wherein one of $R_2$ and $R_6$ is trifluoromethyl and the other is difluoromethyl.

9. The method of claim 8 wherein $R_3$ is methoxy.

10. The method of claim 9 wherein $R_5$ is 2-thiazolyl.

11. A herbicidal composition comprising having as an active ingredient a herbicidal compound represented by the formula

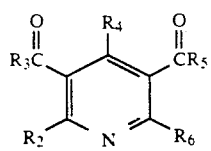

wherein:

$R_2$ and $R_6$ are independently lower alkyl, fluorinated methyl, chlorofluorinated methyl, or chlorinated methyl, provided that one of $R_2$ and $R_6$ is fluorinated methyl or chlorofluorinated methyl;

$R_3$ is alkoxy or alkylthio;

$R_4$ is hydrogen, alkyl, cycloalkyl or cycloalkylalkyl; and $R_5$ is thiazolyl or 4,5-(dihydro)thiazolyl, each optionally substituted with one or more radicals selected from halo, amino, aminocarbonyl, cyano, alkoxy, alkyl, alkoxyalkyl, alkoxycarbonyl, alkylamino, and dialkylamino.

12. The composition of claim 11 wherein $R_4$ is 2-methylpropyl.

13. The composition of claim 11 wherein one of $R_2$ and $R_6$ is trifluoromethyl and the other is difluoromethyl.

14. The composition of claim 11 wherein $R_3$ methoxy.

15. The composition of claim 14 wherein $R_5$ is 2-thiazolyl.

* * * * *